(12) United States Patent
Duchateau et al.

(10) Patent No.: US 11,685,935 B2
(45) Date of Patent: Jun. 27, 2023

(54) COMPACT SCAFFOLD OF CAS9 IN THE TYPE II CRISPR SYSTEM

(71) Applicant: CELLECTIS, Paris (FR)

(72) Inventors: Philippe Duchateau, Draveil (FR); Claudia Bertonati, Paris (FR)

(73) Assignee: CELLECTIS, Paris (FR)

( * ) Notice: Subject to any disclaimer, the term of this patent is extended or adjusted under 35 U.S.C. 154(b) by 356 days.

(21) Appl. No.: 14/892,707

(22) PCT Filed: May 28, 2014

(86) PCT No.: PCT/EP2014/061181
§ 371 (c)(1),
(2) Date: Nov. 20, 2015

(87) PCT Pub. No.: WO2014/191521
PCT Pub. Date: Dec. 4, 2014

(65) Prior Publication Data
US 2016/0102324 A1   Apr. 14, 2016

(30) Foreign Application Priority Data

May 29, 2013  (DK) .............................. PA201370297
Dec. 13, 2013  (DK) .............................. PA201370771

(51) Int. Cl.
| | | |
|---|---|---|
| C12N 15/90 | (2006.01) | |
| C12N 9/22 | (2006.01) | |
| C12N 15/10 | (2006.01) | |
| C12N 15/63 | (2006.01) | |

(52) U.S. Cl.
CPC ............. *C12N 15/907* (2013.01); *C12N 9/22* (2013.01); *C12N 15/902* (2013.01); *C12N 15/1082* (2013.01); *C12N 15/63* (2013.01); *C12Y 301/00* (2013.01); *C12Y 301/26004* (2013.01)

(58) Field of Classification Search
None
See application file for complete search history.

(56) References Cited

U.S. PATENT DOCUMENTS

2014/0068797 A1* 3/2014 Doudna ............... C12N 15/102
800/18

FOREIGN PATENT DOCUMENTS

WO   2013/176772 A1   11/2013

OTHER PUBLICATIONS

Chou et al. Natural Science, 2009; 1:63-92 (Year: 2009).*
Shekhawat et al. Current Opinion in Chemical Biology 2011, 15:789-797 (Year: 2011).*
Freiburg Team: "Truncation of dCas9", Sep. 17, 2013 (Sep. 17, 2013), Retrieved from the Internet: URL:http://2013.igem.org/Team:Freiburg/Project/truncation [retrieved on Jan. 28, 2014].
EBI accession No. UNIPROT:H1D477, Mar. 21, 2012 (Mar. 21, 2012).
EBI accession No. UNIPROT:F5U5Q4, Jul. 27, 2011 (Jul. 27, 2011).
EBI accession No. UNIPROT:D8IJI3, Oct. 5, 2010 (Oct. 5, 2010).
R. Sapranauskas et al: "The *Streptococcus thermophilus* CRISPR/Cas system provides immunity in *Escherichia coli* (Supplementary data)", Nucleic Acids Research, vol. 39, No. 21, Aug. 3, 2011 (Aug. 3, 2011), pp. 9275-9282.
I. Fonfaraetal: "Phylogeny of Cas9 determines functional exchangeability of dual-RNA and Cas9 among orthologous type II CRISPR-Cas systems", Nucleic Acids Research, Nov. 22, 2013 (Nov. 22, 2013).
EBI accession No. UNIPROT:H1D478, Mar. 21, 2012 (Mar. 21, 2012).
EBI accession No. UNIPROT:K1NA00, Nov. 28, 2012 (Nov. 28, 2012).
M. Jinek et al: "Structures of Cas9 Endonucleases Reveal RNA-Mediated Conformational Activation", Science, vol. 343, No. 6176, Mar. 14, 2014 (Mar. 14, 2014), pp. 1247997-1247997.
Nishimasu Hiroshi et al: "Crystal Structure of Cas9 in Complex with Guide RNA and Target DNA", Cell, Cell Press, US, vol. 156, No. 5, Feb. 13, 2014 (Feb. 13, 2014), pp. 935-949.
Prashantmali et al: "Cas9 as a versatile tool for engineering biology", Nature Methods, Nature Publishing Group, GB, vol. 10, No. 10, Sep. 27, 2013 (Sep. 27, 2013), pp. 957-963.
Wright et al., Rational design of a split-Cas9 enzyme complex, Proc. Natl. Acad. Sci. USA vol. 112, No. 10, 2984-2989, Mar. 10, 2015.
Truong et al., Development of an intein-mediated split-Cas9 system for gene therapy, Nucleic Acids Research, vol. 43, No. 13, 2015.
Jinek et al., Structures of Cas9 Endonucleases Reveal RNA-Mediated Conformational Activation, Science vol. 343, 1215, Mar. 14, 2014.
Nishimasu et al., Crystal Structure of Cas9 in Complex with Guide RNA and Target DNA, Cell 156, 935-949, Feb. 27, 2014.
Seeley et al., Mutations in the *Eseherichia coli* UvrB ATPase motif compromise excision repair capacity, Proc. Natl. Acad. Sci. USA vol. 86, pp. 6577-6581, Sep. 1989.

* cited by examiner

*Primary Examiner* — James D Schultz
(74) *Attorney, Agent, or Firm* — Arrigo, Lee, Guttman & Mouta-Bellum LLP

(57) ABSTRACT

The present invention is in the field of CRISPR-Cas system for genome targeting. The present invention relates to new engineered Cas9 scaffolds and uses thereof. More particularly, the present invention relates to methods for genome targeting, cell engineering and therapeutic application. The present invention also relates to vectors, compositions and kits in which the new Cas9 scaffolds of the present invention are used.

28 Claims, 6 Drawing Sheets

Specification includes a Sequence Listing.

COMPACT SCAFFOLD OF CAS9 IN THE TYPE II CRISPR SYSTEM

REFERENCE TO RELATED APPLICATIONS

This application is a U.S. National Stage of International application PCT/EP2014/061181, filed May 28, 2014, which claims the benefit of Danish Applications PA201370297 filed May 29, 2013, and PA201370771 filed Dec. 13, 2013.

FIELD OF THE INVENTION

The present invention is in the field of CRISPR-Cas system for genome targeting. The present invention relates to new engineered Cas9 scaffolds and uses thereof. More particularly, the present invention relates to methods for genome targeting, cell engineering and therapeutic application. The present invention also relates to vectors, compositions and kits in which the new Cas9 scaffolds of the present invention are used.

BACKGROUND OF THE INVENTION

Site-specific nucleases are powerful reagents for specifically and efficiently targeting and modifying a DNA sequence within a complex genome. There are numerous applications of genome engineering by site-specific nucleases extending from basic research to bioindustrial applications and human therapeutics. Re-engineering a DNA-binding protein for this purpose has been mainly limited to the design and production of proteins such as the naturally occurring LADLIDADG homing endonucleases (LHE), artificial zinc finger proteins (ZFP), and Transcription Activator-Like Effectors nucleases (TALE-nucleases).

Recently, a new genome engineering tool has been developed based on the RNA-guided Cas9 nuclease (Gasiunas, Barrangou et al. 2012; Jinek, Chylinski et al. 2012) from the type II prokaryotic CRISPR (Clustered Regularly Interspaced Short palindromic Repeats) adaptive immune system. The CRISPR Associated (Cas) system was first discovered in bacteria and functions as a defense against foreign DNA, either viral or plasmid. So far three distinct bacterial CRISPR systems have been identified, termed type I, II and III. The Type II system is the basis for the current genome engineering technology available and is often simply referred to as CRISPR. The type II CRISPR/Cas loci are composed of an operon of genes encoding the proteins Cas9, Cas1, Cas2 and/or Csn2, a CRISPR array consisting of a leader sequence followed by identical repeats interspersed with unique genome-targeting spacers and a sequence encoding the trans-activating tracrRNA.

CRISPR-mediated adaptative immunity proceeds in three distinct stages: acquisition of foreign DNA, CRISPR RNA (crRNA) biogenesis and target interference (see for review (Sorek, Lawrence et al. 2013)). First, the CRISPR/Cas machinery appears to target specific sequence for integration into the CRISPR locus. Sequences in foreign DNA selected for integration are called spacers and these sequences are often flanked by a short sequence motif, referred as the proto-spacer adjacent motif (PAM). crRNA biogenesis in type II systems is unique in that it requires a trans-activating crRNA (tracRNA). CRISPR locus is initially transcribed as long precursor crRNA (pre-crRNA) from a promoter sequence in the leader. Cas9 acts as a molecular anchor facilitating the base pairing of tracRNA with pre-cRNA for subsequent recognition and cleavage of pre-cRNA repeats by the host RNase III (Deltcheva, Chylinski et al. 2011).

Following the processing events, tracrRNA remains paired to the crRNA and bound to the Cas9 protein. In this ternary complex, the dual tracrRNA:crRNA structure acts as guide RNA that directs the endonuclease Cas9 to the cognate target DNA. Target recognition by the Cas9-tracrRNA:crRNA complex is initiated by scanning the invading DNA molecule for homology between the protospacer sequence in the target DNA and the spacer-derived sequence in the crRNA. In addition to the DNA protospacer-crRNA spacer complementarity, DNA targeting requires the presence of a short motif adjacent to the protospacer (protospacer adjacent motif—PAM). Following pairing between the dual-RNA and the protospacer sequence, Cas9 subsequently introduces a blunt double strand break 3 bases upstream of the PAM motif (Garneau, Dupuis et al. 2010).

Cas9 is a large endonuclease capable of recognizing any potential target of 12 to 20 nucleotides and a specific PAM motif currently restricted to 2 nucleotides (NGG; (Mali, Yang et al. 2013)). The potential target is enough for ensuring unique cleavage site in prokaryotic genomes on a statistical basis, but is critical for larger genomes, like in eukaryotic cells, where potential target sequences may be found several times. There is therefore a need to develop strategies for improving specificity and reducing potential off-site using type II CRISPR system. Moreover, the large size of the natural Cas 9 (>1200 amino acids) is a disadvantage in gene delivery for genome engineering CRISPR system.

In order to improve gene delivery of Cas9 into cells, the present inventors have designed new Cas9 scaffolds including RuvC motif as defined by (D-[I/L]-G-X-X-S-X-G-W-A) (SEQ ID NO: 1) and/or HNH motif as defined by (Y-X-X-D-H-X-X-P-X-S-X-X-X-D-X-S) (SEQ ID NO: 2), wherein X represents any one of 20 natural amino acids and [I/L] represents isoleucine or leucine. These compact scaffolds were obtained by searching for the presence of the above putative motifs in genome databases and identifying those present on separate ORFS. The inventors made the presumption that if such motifs were found on separate subunit proteins, shorter proteins could be identified and fused together to obtain shorter functional fusion proteins.

By pursuing this strategy, the inventors have been able to determine the boundaries of the RuvC and HNH domains and to design new shorter Cas9 derived from the *S. pyogenes* or homologues thereof. Their Cas9 homologues analysis further allowed the identification of previously uncharacterized Cas9 residues involved in the binding of the guide RNA and the PAM motif. By engineering these domains, the inventors increase the number of target nucleotides specifically recognized by type II CRISPR system to avoid off-site target.

SUMMARY OF THE INVENTION

The present invention provides with new RuvC and HNH sequence motifs to be combined with each other to result into more compact and/or more specific recombinant Cas9 scaffolds (i.e. artificial fusion proteins of less than 1100 amino acids). Cas9 protein can be divided into two separate split Cas9 RuvC and HNH domains which can process target nucleic acid sequence together or separately with guideRNA. These scaffolds are used in methods for gene targeting, in particular as specific nucleases for gene editing. Expression vectors encoding these new scaffolds and the cells transformed and engineered with these vectors are also the subject-matter of the invention.

DISCLOSURE OF THE INVENTION

Figure 1:
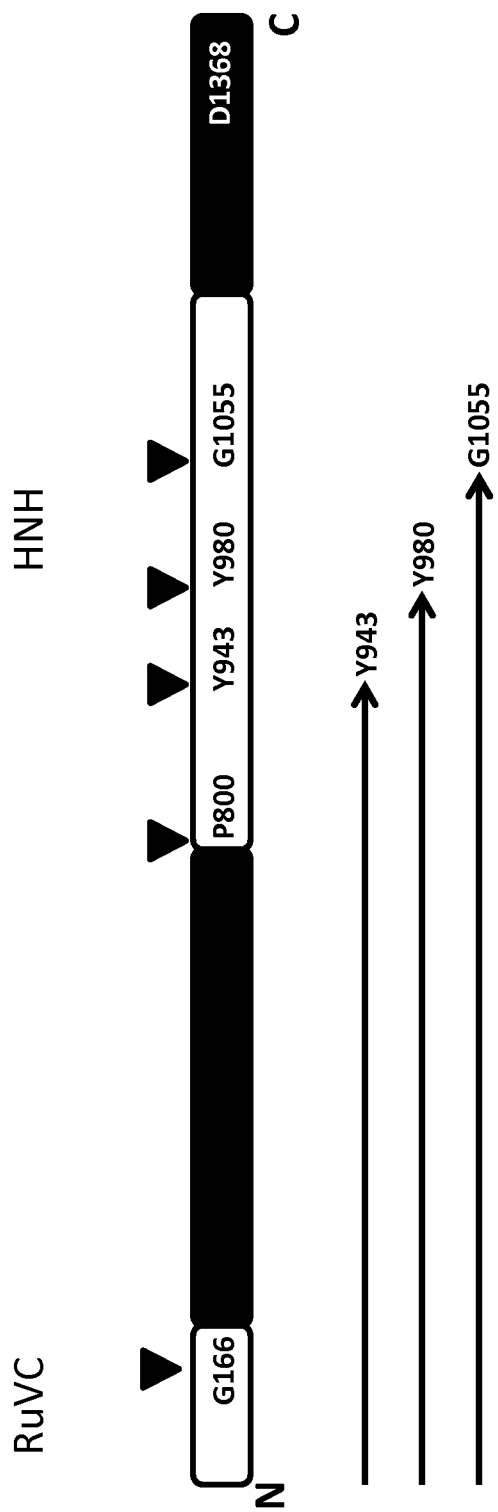
FIG. 1. The original sequence of *S. pyogenes* Cas9 and the proposed truncation Y943, Y980, G1055.

Unless specifically defined herein, all technical and scientific terms used have the same meaning as commonly understood by a skilled artisan in the fields of gene therapy, biochemistry, genetics, molecular biology and immunology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

New Cas 9 Variants

Cas9, also named Csn1 (COG3513) is a large protein that participates in both crRNA biogenesis and in the destruction of invading DNA. Cas9 has been described in different bacterial species such as *S. thermophilus* (Sapranauskas NAR 2011), *Listeria innocua* (jinek Science 2012) and *S. pyogenes* (Deltcheva, Chylinski et al. 2011). The large Cas9 protein (>1200 amino acids) contains two predicted nuclease domains, namely HNH (McrA-like) nuclease domain that is located in the middle of the protein and a split RuvC-like nuclease domain (RNase H fold) (Haft, Selengut et al. 2005; Makarova, Grishin et al. 2006). The insertion of the HNH nuclease domain into the RNAse H fold suggests that the two nuclease activities are closely coupled. Recently, it has been demonstrated that HNH domain is responsible for nicking of one strand of the target double-stranded DNA and the RuvC-like RNase H fold domain is involved in cleavage of the other strand of the double-stranded DNA target (Jinek, Chylinski et al. 2012). Together, these two domains each nick a strand of the target DNA within the proto-spacer in the immediate vicinity of the PAM, which results in blunt cleavage of the invasive DNA (Jinek, Chylinski et al. 2012). According to the present invention, a compact Cas9 variant is an endonuclease comprising less than 1100, preferably less than 1000, more preferably less than 900 amino acids, again more preferably less than 800 amino acids encoding RuvC and HNH domains.

By "Cas 9 variant" is meant an engineering endonuclease or a homologue of Cas9 which is capable of binding dual crRNA:tracRNA (or a single guide RNA) which acts as a guide RNA that directs the Cas9 to the nucleic acid target. In particular embodiment, Cas9 variants can induce a cleavage in the nucleic acid target sequence which can correspond to either a double-stranded break or a single-stranded break. Cas9 variant can be a Cas9 endonuclease that does not naturally exist in nature and that is obtained by genetic engineering or by random mutagenesis. Cas9 variants according to the invention can for example be obtained by mutations i.e. deletions from, or insertions or substitutions of at least one residue in the amino acid sequence of a *S. pyogenes* Cas9 endonuclease (SEQ ID NO: 3). In the frame aspects of the present invention, such Cas9 variants remain functional, i.e. they retain the capacity of binding dual crRNA:tracRNA (or a single guide RNA). Cas9 variant can also be homologues of *S. pyogenes* Cas9 which can comprise deletions from, or insertions or substitutions of, at least one residue within the amino acid sequence of *S. pyogenes* Cas9 (SEQ ID NO: 3). Any combination of deletion, insertion, and substitution may also be made to arrive at the final construct, provided that the final construct possesses the desired activity, in particular the capacity of binding dual crRNa:tracRNA (or a single guide RNA) or nucleic acid target sequence.

RuvC/RNaseH motif includes proteins that show wide spectra of nucleolytic functions, acting both on RNA and DNA (RNaseH, RuvC, DNA transposases and retroviral integrases and PIWI domain of Argonaut proteins). In the present invention the RuvC catalytic domain of the Cas9 protein can be characterized by the sequence motif: D-[I/L]-G-X-X-S-X-G-W-A, wherein X represents any one of the natural 20 amino acids and [I/L] represents isoleucine or leucine (SEQ ID NO: 1). In other terms, the present invention relates to Cas9 variant which comprises at least D-[I/L]-G-X-X-S-X-G-W-A sequence, wherein X represents any one of the natural 20 amino acids and [I/L] represents isoleucine or leucine (SEQ ID NO: 1).

The characterization of the RuvC motif mentioned above allows to extract different homologues of Cas9 RuvC domain. The comparison of smaller RuvC homologues domains (SEQ ID NO: 5 to SEQ ID NO: 12, and SEQ ID NO: 51) with *S. pyogenes* Cas9 allows to determine the boundaries of the ruvC domain in *S. pyogenes* Cas9 (SEQ ID NO: 4). Thus, in a particular embodiment, the Cas9 variant comprises a RuvC domain which comprises the amino acid sequence selected from the group consisting of: SEQ ID NO: 4 to SEQ ID NO: 12 and SEQ ID NO: 51. The multiple sequence alignment of Cas9 homologues allow to determine the optimal breaking position (G247) for the *S. pyogenes* Cas9 sequence. Thus, the RuvC domain can correspond to the amino acid sequence comprising residues from position 1 to position 247 (SEQ ID NO: 52) or aligned positions using CLUSTALW method on homologues of Cas family members.

HNH motif is characteristic of many nucleases that act on double-stranded DNA including colicins, restriction enzymes and homing endonucleases. The domain HNH (SMART ID: SM00507, SCOP nomenclature:HNH family) is associated with a range of DNA binding proteins, performing a variety of binding and cutting functions (Gorbalenya 1994; Shub, Goodrich-Blair et al. 1994). Several of the proteins are hypothetical or putative proteins of no well-defined function. The ones with known function are involved in a range of cellular processes including bacterial toxicity, homing functions in groups I and II introns and inteins, recombination, developmentally controlled DNA rearrangement, phage packaging, and restriction endonuclease activity (Dalgaard, Klar et al. 1997). These proteins are found in viruses, archaebacteria, eubacteria, and eukaryotes. Interestingly, as with the LAGLI-DADG and the GIY-YIG motifs, the HNH motif is often associated with endonuclease domains of self-propagating elements like inteins, Group I, and Group II introns (Gorbalenya 1994; Dalgaard, Klar et al. 1997). The HNH domain can be characterized by the presence of a conserved Asp/His residue flanked by conserved His (amino-terminal) and His/Asp/Glu (carboxy-terminal) residues at some distance. A substantial number of these proteins can also have a CXZC motif on either side of the central Asp/His residue. Structurally, the HNH motif appears as a central hairpin of twisted β-strands, which are flanked on each side by an a helix (Kleanthous, Kuhlmann et al. 1999). In the present invention, the HNH motif can be characterized by the sequence motif: Y-X-X-D-H-X-X-P-X-S-X-X-X-D-X-S, wherein X represents any one of the natural 20 amino acids (SEQ ID NO: 2). The present invention relates to a Cas9 variant which comprises at least Y-X-X-D-H-X-X-P-X-S-X-X-X-D-X-S sequence wherein X represents any one of the natural 20 amino acids (SEQ ID NO: 2).

The minimal region of the HNH domain and the different homologues of HNH domain characterized in this study can be used to engineer a Cas9 variant. Thus, the present invention relates to a Cas9 variant which comprises a HNH domain comprising amino acid sequences selected from SEQ ID NO: 13 to SEQ ID NO: 22. The multiple sequence alignment of Cas9 homologues allow to determine the optimal breaking position (G247) for the *S. pyogenes* Cas9 sequence. Thus, the HNH domain can correspond to the amino acid sequence comprising residues from position 248 to position 1368 (SEQ ID NO: 53) or aligned positions using CLUSTALW method on homologues of Cas family members.

The alignment of *S. pyogenes* Cas9 and homologues members suggests that C-terminal region of Cas9 are dispensable. Thus, C-terminal domain of Cas9 is truncated after the HNH motif Y-X-X-D-H-X-X-P-X-S-X-X-X-D-X-S, preferably between 1 to 1000 amino acid residues after the HNH motif, more preferably between 1 to 500, more preferably between 1 to 250 amino acids after the HNH motif. More particularly, Cas9 variant comprises a HNH domain comprising the amino acid sequence selected from the group consisting of: SEQ ID NO: 23 to 25.

In another approach, the inventors identified four natural Cas9 homologues with shorter sequence and determined shorter version of *S. pyogenes* Cas9. Thus, the present invention also relates to Cas 9 which comprises amino acid sequences selected from the group consisting of SEQ ID NO: 26 to SEQ ID NO: 33.

In a particular embodiment, the Cas9 of the present invention comprises Y-X-X-D-H-X-X-P-X-S-X-X-X-D-X-S sequence and D-[I/L]-G-X-X-S-X-G-W-A wherein X represents any one of the natural 20 amino acids. More particularly, the Cas9 comprises a RuvC domain comprising an amino acid sequence selected from the group consisting of: SEQ ID NO: 4 to SEQ ID NO: 12 and SEQ ID NO: 51, and a HNH domain comprising an amino acid sequence selected from the group consisting of: SEQ ID NO: 13 to SEQ ID NO: 25.

In a more particular embodiment, said RuvC domain and HNH domain as described above is separated by a peptide domain. This peptide domain can be as non limiting example a non-specific linker ((GS)n) as well as small domains (i.e. Immonuglobulin domain, TPR, pumilo, RRM fold). In a particular embodiment, said peptide domain comprises an amino acid sequence selected from the group consisting of SEQ ID NO: 49 and SEQ ID NO: 50.

The above characterization of the RuvC and HNH domains prompted the inventors to engineer Cas9 protein to create split Cas9 protein. Cas9 protein has been divided into two separate RuvC and HNH domains. Surprisingly, the inventors showed that these two split Cas9 could process together or separately the nucleic acid target (see example 4). This observation allows developing a new Cas9 system using split Cas9 proteins. Each Cas9 domains as described above can be prepared and used separately. Thus, this split system displays several advantages for vectorization, allowing to deliver shorter protein than the entire Cas9, protein purification and protein engineering, particularly to engineer region responsible of PAM recognition, DNA binding.

By "Split Cas9" is meant here a reduced or truncated form of a Cas9 protein or Cas9 variant, which comprises either a RuvC or HNH domain, but not both of these domains. Such "Split Cas9" can be used independently with guide RNA or in a complementary fashion, like for instance, one Split Cas9 providing a RuvC domain and another providing the HNH domain. Different split Cas9 may be used together having either RuvC and/or NHN domains. Split Cas9 are preferably less than 1000 amino acids long, more preferably less than 800, even more preferably less than 500 amino acids long.

RuvC domain generally comprises at least an amino acid sequence D-[I/L]-G-X-X-S-X-G-W-A, wherein X represents any one of the natural 20 amino acids and [I/L] represents isoleucine or leucine (SEQ ID NO: 1). HNH domain generally comprises at least an amino acid sequence Y-X-X-D-H-X-X-P-X-S-X-X-X-D-X-S sequence, wherein X represents any one of the natural 20 amino acids (SEQ ID NO: 2).

In a preferred embodiment said split cas9 protein comprises a RuvC domain comprising an amino acid sequence selected from the group consisting of: SEQ ID NO: 4 to SEQ ID NO: 12 and SEQ ID NO: 51 and 53, and a HNH domain comprising an amino acid sequence selected from the group consisting of: SEQ ID NO: 13 to SEQ ID NO: 25 and 52, preferably a RuvC domain comprising an amino acid sequence SEQ ID NO: 52 and an HNH domain comprising an amino acid sequence SEQ ID NO: 53. In a preferred embodiment, said HNH domain comprises a first amino acid Leucine mutated in Valine in SEQ ID NO: 53 to have a better kozak consensus sequence.

Each Cas9 split domain can be derived from different Cas9 homologues, or can be derived from the same Cas9. Each split domain can be fused to at least one active domain in the N-terminal and/or C-terminal end, said active domain can be selected from the group consisting of: nuclease (e.g. endonuclease or exonuclease), polymerase, kinase, phosphatase, methylase, demethylase, acetylase, desacetylase, topoisomerase, integrase, transposase, ligase, helicase, recombinase, transcriptional activator (e.g. VP64, VP16), transcriptional inhibitor (e. g; KRAB), DNA end processing enzyme (e.g. Trex2, Tdt), reporter molecule (e.g. fluorescent proteins, LacZ, luciferase).

In a particular embodiment, said split domains can be fused to an energy acceptor and the complementary split domain to an energy donor such that the emission spectrum of the fluorescent molecule energy donor overlaps with the absorption spectrum of the energy acceptor the energy. When split Cas9 domains binds DNA together and when energy donor and acceptor are closed to each other, FRET (Fluorescence resonance energy transfer) occurs and results in reduction of the intensity of donor emission, as energy from the donor in its excited state is transferred to the acceptor.

In another particular embodiment, said Cas9 split domains are separated by a linker capable of inactivating the resulting protein. Addition of a specific small molecule changing the conformational structure of the split domains induces their activity. In another particular embodiment, said linker can comprise a protease cleavage site (e.g. HIV1 protease cleavage site). In the presence of a specific protease, the linker is cleaved and the resulting isolated RuvC and HNH domains can bind the target nucleic acid. Thus, the use of said RuvC and HNH domain linked together is particularly suitable to induce Cas9 activation at the desired time In another aspect of the invention, to modulate Cas9 specificity, the inventors identified the residues involved in the binding of PAM motif and crRNA. Thus, the invention encompasses a Cas9 variant or split Cas9 domain which comprises at least one mutated amino acid residue in the nucleic acid binding region of *S. pyogenes* Cas9, preferably in amino acid sequence selected from the group consisting of SEQ ID NO: 34 to SEQ ID NO: 48.

Cas9 homologues domains identified in the present invention can also be engineered. The DNA/RNA binding region of Cas9 homologues can be determined by the multiple alignment sequences of example 1 and 2 (grey highlighted sequences in Tables 1, 3 and 5). Thus, the invention relates to a Cas9 variant, or split Cas9 domain which comprises at least one mutated amino acid residue in the nucleic acid binding region as described above. Said split Cas9 domains can be derived from different Cas9 homologues or variant according to the present invention.

In a particular aspect, this Cas9 variant can be able to bind a smaller or larger PAM motif which comprises combinations of any one of 20 natural amino acids (non natural PAM motif). Preferably, the Cas9 variant or split Cas9 domain according to the invention is capable of specifically recognizing a PAM motif which comprises at least 3, preferably 4, more preferably 5 nucleotides. The capacity of Cas9 to bind a PAM motif within the genomic DNA, in absence of crRNA (or guide RNA) can present a toxic effect when Cas9 is overexpressed in the cell. Thus, to avoid this potential toxic effect, the inventors sought to engineer Cas9 variant or split Cas9 domain which are not capable of binding a PAM motif. The Cas9 variant or split Cas9 domain according to the present invention comprises at least one amino acid residue in the PAM binding region, preferably in the region from residue T38 to E57 and/or from T146 to L169 of the SEQ ID NO: 3 or aligned positions using CLUSTALW method on homologues of Cas family members.

In another aspect, the Cas9 variant or split Cas9 domain may also be able to induce the binding of a smaller or larger complementary sequence of guide RNA on the nucleic acid target sequence.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application. The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO: 3 to SEQ ID NO: 53.

Recently, it has been demonstrated that HNH domain is responsible for nicking of one strand of the target double-stranded DNA and the RuvC-like RNaseH fold domain is involved in cleavage of the other strand of the double-stranded DNA target (Jinek, Chylinski et al. 2012). Together, these two domains each nick a strand of the target DNA within the proto-spacer in the immediate vicinity of the PAM, which results in blunt cleavage of the invasive DNA (Jinek, Chylinski et al. 2012). In particular embodiment, Cas9 variant lacks one nickase activity. In particular, Cas9 variant or split Cas9 comprises inactivating mutation(s) in the catalytic residues of either the HNH or RuvC-like domains. This resulting Cas9 or split Cas9 is known to function as a nickase and induce a single-strand break in the target nucleic acid sequence. As non limiting example, the catalytic residues of the Cas9, protein or split Cas9 domain can be the D10, D31, H840, H868, N882 and N891 of SEQ ID NO: 3 or aligned positions using CLUSTALW method on homologues of Cas family members. The residues comprised in HNH or RuvC motifs can be those described in the above paragraph. Any one of these residues can be replaced by any other amino acids, preferably by alanine residue. Mutation in the catalytic residues means either substitution by another amino acids, or deletion or addition of amino acids that induce the inactivation of at least one of the catalytic domain of cas9 (Sapranauskas, Gasiunas et al. 2011; Jinek, Chylinski et al. 2012). In a particular embodiment, the Cas9 variant comprises only one of the two RuvC and HNH catalytic domains. In a particular embodiment, isolated RuvC and/or HNH domain can comprise inactivation mutation in the catalytic residues as described above.

In another aspect of the present invention, Cas9 lacks endonucleolytic activity. The resulting Cas9 is co-expressed with guide RNA designed to comprises a complementary sequence to a target nucleic acid sequence. Expression of Cas9 lacking endonucleolytic activity yields to specific silencing of the gene of interest. This system is named CRISPR interference (CRISPRi) (Qi, Larson et al. 2013). By silencing, it is meant that the gene of interest is not expressed in a functional protein form. The silencing may occur at the transcriptional or the translational step. According to the present invention, the silencing may occur by directly blocking transcription, more particularly by blocking transcription elongation or by targeting key cis-acting motifs within any promoter, sterically blocking the association of their cognate trans-acting transcription factors. The Cas9 lacking endonucleolytic activity comprises both non-functional HNH and RuvC domains. In particular, the Cas9 polypeptide comprises inactivating mutations in the catalytic residues of both the RuvC-like and HNH domains. For example, the catalytic residues required for cleavage Cas9 activity can be the D10, D31, H840, H865, H868, N882 and N891 of SEQ ID NO: 3 or aligned positions using CLUSTALW method on homologues of Cas Family members. The residues comprised in HNH or RuvC motifs can be those described in the above paragraph. Any of these residues can be replaced by any one of the other amino acids, preferably by alanine residue. Mutation in the catalytic residues means either substitution by another amino acids, or deletion or addition of amino acids that induce the inactivation of at least one of the catalytic domain of cas9.

The invention also concerns the polynucleotides, in particular DNA or RNA encoding the polypeptides and proteins previously described. These polynucleotides may be included in vectors, more particularly plasmids or virus, in view of being expressed in prokaryotic or eukaryotic cells.

The present invention contemplates modification of the Cas9, split Cas9 polynucleotide sequence such that the codon usage is optimized for the organism in which it is being introduced. Thus, for example Cas9 polynucleotide sequence derived from the *pyogenes* or *S. Thermophilus* codon optimized for use in human is set forth in (Cong, Ran et al. 2013; Mali, Yang et al. 2013).

In particular embodiments, the Cas9, split Cas9 polynucleotides according to the present invention can comprise at least one subcellular localization motif. A subcellular localization motif refers to a sequence that facilitates transporting or confining a protein to a defined subcellular location that includes at least one of the nucleus, cytoplasm, plasma membrane, endoplasmic reticulum, golgi apparatus, endosomes, peroxisomes and mitochondria. Subcellular localization motifs are well-known in the art. A subcellular localization motif requires a specific orientation, e.g., N- and/or C-terminal to the protein. As a non-limiting example, the nuclear localization signal (NLS) of the simian virus 40 large T-antigen can be oriented at the N and/or C-terminus. NLS is an amino acid sequence which acts to target the protein to the cell nucleus through Nuclear Pore Complex and to direct a newly synthesized protein into the nucleus via its recognition by cytosolic nuclear transport receptors. Typically, a NLS consists of one or more short sequences of positively charged amino acids such as lysines or arginines.

In particular embodiments, the polynucleotide encoding a cas9 variant or a split Cas9 according to the present invention is placed under the control of a promoter. Suitable promoters include tissue specific and/or inducible promoters. Tissue specific promoters control gene expression in a tissue-dependent manner and according to the developmental stage of the cell. The transgenes driven by these type of promoters will only be expressed in tissues where the transgene product is desired, leaving the rest of the tissues unmodified by transgene expression. Tissue-specific promoters may be induced by endogenous or exogenous factors, so they can be classified as inducible promoters as well. An inducible promoter is a promoter which initiates transcription only when it is exposed to some particular (typically external) stimulus. Particularly preferred for the present invention are: a light-regulated promoter, nitrate reductase promoter, eukaryotic metallothionine promoter, which is induced by increased levels of heavy metals, prokaryotic lacZ promoter which is induced in response to isopropyl-β-D-thiogalacto-pyranoside (IPTG), steroid-responsive promoter, tetracycline-dependent promoter and eukaryotic heat shock promoter which is induced by increased temperature.

Method of Genome Targeting

In another aspect, the present invention relates to a method for use of said polypeptides and/or polynucleotides according to the invention for various applications ranging from targeted nucleic acid cleavage to targeted gene regulation. In genome engineering experiments, the efficiency of Cas9/CRISPR system as referred to in the present patent application, e.g. their ability to induce a desired event (Homologous gene targeting, targeted mutagenesis, sequence removal or excision) at a locus, depends on several parameters, including the specific activity of the nuclease, probably the accessibility of the target, and the efficacy and outcome of the repair pathway(s) resulting in the desired event (homologous repair for gene targeting, NHEJ pathways for targeted mutagenesis).

The present invention relates to a method for gene targeting using the cas9 described above. The present invention relates to a method comprising one or several of the following steps:
  (a) selecting a target nucleic acid sequence, optionally comprising a PAM motif in the cell;
  (b) providing a guideRNA comprising a sequence complementary to the target nucleic acid sequence;
  (c) introducing into the cell the guide RNA and said Cas9, such that Cas9 processes the target nucleic acid sequence in the cell.

In a particular embodiment, the method comprises:
  (a) selecting a target nucleic acid sequence, optionally comprising a PAM motif in the cell;
  (b) providing a crRNA comprising a sequence complementary to the target nucleic acid sequence;
  (c) Providing a TracrRNA comprising a sequence complementary to a portion of the crRNA and a Cas9 as described above;
  (d) introducing into the cell the crRNA, said TracrRNA and said Cas9, such that Cas9-tracrRNA:crRNA complex process the target nucleic acid sequence in the cell.

In another particular embodiment, said method comprises:
  (a) selecting a target nucleic acid sequence, optionally comprising a PAM motif in the cell;
  (b) providing a guide RNA comprising a sequence complementary to the target nucleic acid sequence;
  (c) providing at least one split Cas9 domain as described above;
  (d) introducing into the cell said split Cas9 domain, such that said split Cas9 domain processes the target nucleic acid sequence in the cell.

Said Cas9 split domains (RuvC and HNH domains) can be simultaneously or sequentially introduced into the cell such that said split Cas9 domain(s) process the target nucleic acid sequence. The Cas9 split system is particularly suitable for an inducible method of genome targeting. In a preferred embodiment, to avoid the potential toxic effect of the Cas9 overexpression within the cell, a non-functional split Cas9 domain is introduced into the cell, preferably by stably transforming said cell with a transgene encoding said split domain. Then, the complementary split part of Cas9 is introduced into the cell, such that the two split parts reassemble into the cell to reconstitute a functional Cas9 protein at the desired time. Said split Cas9 can derive from the same Cas9 protein or can derive from different Cas9 variants, particularly RuvC and HNH domains as described above.

In another particular embodiment, the method of gene targeting using the split cas9 protein can further comprise adding antibodies or small molecules which bind to the interface between the two split Cas9 protein and thus avoid split Cas9 reassembling to reconstitute a functional Cas9 protein. To induce Cas9 activation, the antibodies or small molecules have to be removed by a washing step.

In another aspect of the invention, only one split Cas9 domain is introduced into said cell. Indeed, surprisingly the inventors showed that the split Cas9 domain comprising the RuvC motif as described above is capable of cleaving a target nucleic acid sequence independently of split domain comprising the HNH motif. The guideRNA does not need the presence of the HNH domain to bind to the target nucleic acid sequence and is sufficiently stable to be bound by the RuvC split domain.

In a preferred embodiment, said split Cas9 domain alone is capable of nicking said target nucleic acid sequence.

This Cas9 split system is particularly suitable for an inducible method of genome targeting. In a preferred embodiment, to avoid the potential toxic effect of the Cas9 overexpression within the cell, a HNH split Cas9 domain can be introduced into the cell, preferably by stably transforming said cell with a transgene encoding said split domain. Then, the complementary split part of Cas9 (RuvC domain) is introduced into the cell, such that the two split parts reassemble into the cell to reconstitute a functional Cas9 protein at the desired time.

The term "process" as used herein means that sequence is considered modified simply by the binding of the Cas9. Depending of the Cas9 used, different processed event can be induced within the target nucleic acid sequence. As non limiting example, Cas9 can induce cleavage, nickase events or can yield to specific silencing of the gene of interest. Any target nucleic acid sequence can be processed by the present methods. The target nucleic acid sequence (or DNA target) can be present in a chromosome, an episome, an organellar genome such as mitochondrial or chloroplast genome or genetic material that can exist independently to the main body of genetic material such as an infecting viral genome, plasmids, episomes, transposons for example. A target nucleic acid sequence can be within the coding sequence of a gene, within transcribed non-coding sequence such as, for example, leader sequences, trailer sequence or introns, or within non-transcribed sequence, either upstream or downstream of the coding sequence. The nucleic acid target sequence is defined by the 5' to 3' sequence of one strand of said target.

Any potential selected target nucleic acid sequence in the present invention may have a specific sequence on its 3' end, named the protospacer adjacent motif or protospacer associated motif (PAM). The PAM is present in the targeted nucleic acid sequence but not in the guide RNA that is produced to target it. Preferably, the proto-spacer adjacent motif (PAM) may correspond to 2 to 5 nucleotides starting immediately or in the vicinity of the proto-spacer at the leader distal end. The sequence and the location of the PAM vary among the different systems. PAM motif can be for examples NNAGAA, NAG, NGG, NGGNG, AWG, CC, CC, CCN, TCN, TTC as non limiting examples (shah SA, RNA biology 2013). Different Type II systems have differing PAM requirements. For example, the S. pyogenes system requires an NGG sequence, where N can be any nucleotides. S. thermophilus Type II systems require NGGNG (Horvath and Barrangou 2010) and NNAGAAW (Deveau, Barrangou et al. 2008), while different S. mutant systems tolerate NGG or NAAR (van der Ploeg 2009). PAM is not restricted to the region adjacent to the proto-spacer but can also be part of the proto-spacer (Mojica, Diez-Villasenor et al. 2009). In a particular embodiment, the Cas9 protein can be engineered to recognize a non natural PAM motif. In this case, the selected target sequence may comprise a smaller or a larger PAM motif with any combinations of amino acids. In a preferred embodiment, the selected target sequence comprise a PAM motif which comprises at least 3, preferably, 4, more preferably 5 nucleotides recognized by the Cas9 variant according to the present invention. Preferably, the Cas9 variant comprise at least one mutated residue in the DNA/RNA binding region, preferably in the amino acid sequence selected from the group consisting of SEQ ID NO: 34 to SEQ ID NO: 48 and recognizes a non natural PAM motif. The aligned region (see Table 1, 3 and 5) of the Cas9 homologues can also be mutated in the present invention to recognize a non natural PAM motif. The capacity of Cas9 to bind a PAM motif within the genomic DNA, in absence of crRNA (or guide RNA) can present a potential toxic effect when Cas9 is overexpressed in the cell. Thus, to avoid this potential toxic effect, the inventors sought to engineer Cas9 or split Cas9 domain which are not capable of binding a PAM motif. The Cas9 variant or split Cas9 domain according to the present invention comprises at least one amino acid residue in the PAM binding region to avoid PAM binding, preferably in the region from residue T38 to E57 and/or from T146 to L169 of the SEQ ID NO: 3 or aligned positions using CLUSTALW method on homologues of Cas family members.

The method of the present invention comprises providing an engineered guide RNA. Guide RNA corresponds to a nucleic acid comprising a complementary sequence to a target nucleic acid sequence. Preferably, guide RNA corresponds to a crRNA and tracrRNA which can be used separately or fused together. In natural type II CRISPR system, the CRISPR targeting RNA (crRNA) targeting sequences are transcribed from DNA sequences known as protospacers. Protospacers are clustered in the bacterial genome in a group called a CRISPR array. The protospacers are short sequences (~20 bp) of known foreign DNA separated by a short palindromic repeat and kept like a record against future encounters. To create the crRNA, the CRISPR array is transcribed and the RNA is processed to separate the individual recognition sequences between the repeats. The spacer-containing CRISPR locus is transcribed in a long pre-crRNA. The processing of the CRISPR array transcript (pre-crRNA) into individual crRNAs is dependent on the presence of a trans-activating crRNA (tracrRNA) that has sequence complementary to the palindromic repeat. The tracrRNA hybridizes to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9 and form the Cas9-tracrRNA:crRNA complex. Engineered crRNA with tracrRNA is capable of targeting a selected nucleic acid sequence, obviating the need of RNase III and the crRNA processing in general (Jinek, Chylinski et al. 2012).

In the present invention, guide RNA is engineered to comprise a sequence complementary to a portion of a target nucleic acid such that it is capable of targeting, preferably cleaving the target nucleic acid sequence. In a particular embodiment, the guide RNA comprises a sequence of 5 to 50 nucleotides, preferably at least 12 nucleotides which is complementary to the target nucleic acid sequence. In a more particular embodiment, the guide RNA is a sequence of at least 30 nucleotides which comprises at least 10 nucleotides, preferably 12 nucleotides complementary to the target nucleic acid sequence.

In the present invention, RNA/DNA binding region of Cas9 can be engineered to allow the recognition of larger guide RNA sequence. In particular, said RNA/DNA binding region of Cas9 can be engineered to increase the number of nucleotides which specifically bind the nucleic acid target sequence. In a particular embodiment, at least 12 nucleotides specifically binds the nucleic acid target sequence, more preferably at least 15 nucleotides, more preferably again at least 20 nucleotides.

In another aspect, guide RNA can be engineered to comprise a larger sequence complementary to a target nucleic acid. Indeed, the inventors showed that the RuvC split Cas9 domain is able to cleave the target nucleic acid sequence only with a tracRNA:crRNA complex (guide RNA). Thus, the guide RNA can bind the target nucleic acid sequence in absence of the HNH split Cas9 domain. The guide RNA can be designed to comprise a larger complementary sequence, preferably more than 20 bp, to increase the annealing between DNA-RNA duplex without the need to have the stability effect of the HNH split domain binding. Thus, the guide RNA can comprise a complementary sequence to a target nucleic acid sequence of more than 20 bp. Such guide RNA allow increasing the specificity of the Cas9 activity.

The guideRNA does not need the presence of the HNH domain to bind to the target nucleic acid sequence and is sufficiently stable to be bound by the RuvC split domain. Thus, in another particular embodiment, said guide RNA comprises only a nucleic acid sequence, preferably a RNA sequence comprising a complementary sequence to said target nucleic acid sequence without a tracrRNA sequence. Said complementary sequence comprises at least 10 nucleotides, preferably at least 20 nucleotides.

The guide RNA may also comprise a complementary sequence followed by 4-10 nucleotides on the 5' end to improve the efficiency of targeting (Cong, Ran et al. 2013; Mali, Yang et al. 2013). In preferred embodiment, the complementary sequence of the guide RNA is followed in 3' end by a nucleic acid sequence named repeat sequences or 3' extension sequence. Coexpression of several guide RNA with distinct complementary regions to two different genes targeted both genes can be used simultaneously. Thus, in particular embodiment, the guide RNA can be engineered to recognize different target nucleic acid sequences simultaneously. In this case, same guide RNA comprises at least two distinct sequences complementary to a portion of the different target nucleic acid sequences. In a preferred embodiment, said complementary sequences are spaced by a repeat sequence.

The guide RNA according to the present invention can also be modified to increase its stability of the secondary structure and/or its binding affinity for Cas9. In a particular embodiment, the guide RNA can comprise a 2', 3'-cyclic phosphate. The 2', 3'-cyclic phosphate terminus seems to be involved in many cellular processes i.e. tRNA splicing, endonucleolytic cleavage by several ribonucleases, in self-cleavage by RNA ribozyme and in response to various cellular stress including accumulation of unfolded protein in the endoplasmatic reticulum and oxidative stress (Schutz, Hesselberth et al. 2010). The inventors have speculated that the 2', 3'-cyclic phosphate enhances the guide RNA stability or its affinity/specificity for Cas9. Thus, the present invention relates to the modified guide RNA comprising a 2', 3'-cyclic phosphate, and the methods for genome engineering based on the CRISPR/cas system (Jinek, Chylinski et al. 2012; Cong, Ran et al. 2013; Mali, Yang et al. 2013) using the modified guide RNA.

The guide RNA may also comprise a Trans-activating CRISPR RNA (TracrRNA). TracrRNA according to the present invention are characterized by an anti-repeat sequence capable of base-pairing with at least a part of the 3' extension sequence of crRNA to form a tracrRNA:crRNA also named guideRNA (gRNA). TracrRNA comprises a sequence complementary to a region of the crRNA. A synthetic single guide RNA (sgRNA) comprising a fusion of crRNA and tracrRNA that forms a hairpin that mimics the tracrRNA-crRNA complex (Jinek, Chylinski et al. 2012; Cong, Ran et al. 2013; Mali, Yang et al. 2013) can be used to direct Cas9 endonuclease-mediated cleavage of target nucleic acid. This system has been shown to function in a variety of eukaryotic cells, including human, zebra fish and yeast. The sgRNA may comprise two distinct sequences complementary to a portion of the two target nucleic acid sequences, preferably spaced by a repeat sequence.

The methods of the invention involve introducing guide RNA, split Cas9 or Cas9 into a cell. Guide RNA, Cas9 or split Cas9 domain may be synthesized in situ in the cell as a result of the introduction of polynucleotide encoding RNA or polypeptides into the cell. Alternatively, the guide RNA, split Cas9, Cas9 RNA or Cas9 polypeptides could be produced outside the cell and then introduced thereto. Methods for introducing a polynucleotide construct into bacteria, plants, fungi and animals are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposomes and the like. For example, transient transformation methods include for example microinjection, electroporation or particle bombardment. Said polynucleotides may be included in vectors, more particularly plasmids or virus, in view of being expressed in prokaryotic or eukaryotic cells.

cas9 according to the present invention can induce genetic modification resulting from a cleavage event in the target nucleic acid sequence that is commonly repaired through non-homologous end joining (NHEJ). NHEJ comprises at least two different processes. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. By "cleavage event" is intended a double-strand break or a single-strand break event. Said modification may be a deletion of the genetic material, insertion of nucleotides in the genetic material or a combination of both deletion and insertion of nucleotides.

The present invention also relates to a method for modifying target nucleic acid sequence further comprising the step of expressing an additional catalytic domain into a host cell. In a more preferred embodiment, the present invention relates to a method to increase mutagenesis wherein said additional catalytic domain is a DNA end-processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain selected from the group consisting of hExoI (EXO1_HUMAN), Yeast ExoI (EXO1_YEAST), *E. coli* ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain has TREX exonuclease activity, more preferably TREX2 activity. In another preferred embodiment, said catalytic domain is encoded by a single chain TREX polypeptide. Said additional catalytic domain may be fused to a nuclease fusion protein or chimeric protein according to the invention optionally by a peptide linker.

Endonucleolytic breaks are known to stimulate the rate of homologous recombination. Therefore, in another preferred embodiment, the present invention relates to a method for inducing homologous gene targeting in the nucleic acid target sequence further comprising providing to the cell an exogeneous nucleic acid comprising at least a sequence homologous to a portion of the target nucleic acid sequence, such that homologous recombination occurs between the target nucleic acid sequence and the exogeneous nucleic acid.

In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogeneous nucleic acid. Preferably, homologous sequences of at least 50 bp, preferably more than 100 bp and more preferably more than 200 bp are used within said donor matrix. Therefore, the exogenous nucleic acid is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

Depending on the location of the target nucleic acid sequence wherein break event has occurred, such exogenous nucleic acid can be used to knock-out a gene, e.g. when exogenous nucleic acid is located within the open reading frame of said gene, or to introduce new sequences or genes of interest. Sequence insertions by using such exogenous nucleic acid can be used to modify a targeted existing gene, by correction or replacement of said gene (allele swap as a non-limiting example), or to up- or down-regulate the expression of the targeted gene (promoter swap as non-limiting example), said targeted gene correction or replacement.

Modified Cells and Kits

A variety of cells are suitable for use in the method according to the invention. Cells can be any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant, algal or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenurn, Trichoderma reesei, Mortierella alpine, Chrysosporium lucknowense, Kluyveromyceslactis, Pichia pastoris* or *Pichia ciferrii*. More preferably the plant is of the genus *Arabidospis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum tuberosum, Solanum melongena, Solanum esculenturn, Lactuca saliva, Brassica napus, Brassica oleracea, Brassica rapa, Oryza glaberrima, Oryza sativa, Asparagus officinalis, Pisumsativum, Medicago sativa, Zea mays, Hordeum vulgare, Secale cereal, Triticuma estivum, Triticum durum, Capsicum sativus, Cucurbitapepo, Citrullus lanatus, Cucumis melo, Citrus aurantifolia, Citrus maxima, Citrus medico, Citrus reticulata*. More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo solar, Oncorhynchus mykiss, Gallus gallus, Meleagris gallopavo, Drosophila melanogaster, Caenorhabditis elegans*.

In the present invention, the cell is preferably a plant cell, a mammalian cell, a fish cell, an insect cell or cell lines derived from these organisms for in vitro cultures or primary cells taken directly from living tissue and established for in vitro culture. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells. Are also encompassed in the scope of the present invention stem cells, embryonic stem cells and induced Pluripotent Stem cells (iPS).

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

A particular aspect of the present invention relates to an isolated cell as previously described obtained by the method according to the invention. Typically, said isolated cell comprises at least a Cas9 variant, or a split cas9 domain as described above, optionally with guide RNA. Resulting isolated cell comprises a modified target nucleic acid sequence. The resulting modified cell can be used as a cell line for a diversity of applications ranging from bioproduction, animal transgenesis (by using for instance stem cells), plant transgenesis (by using for instance protoplasts), to cell therapy (by using for instance T-cells). The methods of the invention are useful to engineer genomes and to reprogram cells, especially iPS cells and ES cells. Another aspect of the invention is a kit for cell transformation comprising a Cas9 variant or a split Cas9 protein as previously described. This kit more particularly comprise a Cas9 variant or a split Cas9 protein comprising no more than 1100 amino acids encoding for RuvC and/or HNH domains comprising at least one RuvC motif sequence D-[I/L]-G-X-X-S-X-G-W-A or one HNH motif sequence Y-X-X-D-H-X-X-P-X-S-X-X-X-D-X-S, wherein X is anyone of the 20 natural amino acids and [I/L] represents isoleucine or leucine. The kit may also comprise a Cas9 variant or split Cas9 domain comprising at least one residue mutated in the DNA/RNA binding region, preferably in amino acid sequence SEQ ID NO: 34 to SEQ ID NO: 48. The kit may further comprise one or several components of the type II CRISPR system as described above, such as guide RNA, or crRNA comprising a sequence complementary to a nucleic acid target and at least one tracrRNA.

Method for Generating an Animal/a Plant

Animals may be generated by introducing Cas9, a split Cas9 protein, guide RNA into a cell or an embryo. In particular, the present invention relates to a method for generating an animal, comprising providing an eukaryotic cell comprising a target nucleic acid sequence into which it is desired to introduce a genetic modification; generating a cleavage within the target nucleic acid sequence by introducing a cas9 according to the present invention; and generating an animal from the cell or progeny thereof, in which cleavage has occurred. Typically, the embryo is a fertilized one cell stage embryo. Polynucleotides may be introduced into the cell by any of the methods known in the art including micro injection into the nucleus or cytoplasm of the embryo. In a particular embodiment, the method for generating an animal, further comprises introducing an exogenous nucleic acid as desired. The exogenous nucleic acid can include for example a nucleic acid sequence that disrupts a gene after homologous recombination, a nucleic acid sequence that replaces a gene after homologous recombination, a nucleic acid sequence that introduces a mutation into a gene after homologous recombination or a nucleic acid sequence that introduce a regulatory site after homologous recombination. The embryos are then cultured to develop an animal. In one aspect of the invention, an animal in which at least a target nucleic acid sequence of interest has been engineered is provided. For example, an engineered gene may become inactivated such that it is not transcribed or properly translated, or an alternate form of the gene is expressed. The animal may be homozygous or heterozygous for the engineered gene.

The present invention also relates to a method for generating a plant comprising providing a plant cell comprising a target nucleic acid sequence into which it is desired to introduce a genetic modification; generating a cleavage within the target nucleic acid sequence by introducing a Cas9 or a split Cas9 protein according to the present invention; and generating a plant from the cell or progeny thereof, in which cleavage has occurred. Progeny includes descendants of a particular plant or plant line. In a particular embodiment, the method for generating a plant, further comprise introducing an exogenous nucleic acid as desired. Said exogenous nucleic acid comprises a sequence homologous to at least a portion of the target nucleic acid sequence, such that homologous recombination occurs between said exogenous nucleic acid and the target nucleic acid sequence in the cell or progeny thereof. Plant cells produced using methods can be grown to generate plants having in their genome a modified target nucleic acid sequence. Seeds from such plants can be used to generate plants having a phenotype such as, for example, an altered growth characteristic, altered appearance, or altered compositions with respect to unmodified plants.

In a particular embodiment, an animal or a plant may be generated by introducing only one split Cas9 protein. Another animal or plant may be generated by introducing the complementary split Cas9 protein. The resulting animals or plants can be crossed together, to generate descendants expressing both split Cas9 proteins which can cleave target nucleic acid sequence.

The polypeptides of the invention are useful to engineer genomes and to reprogram cells, especially iPS cells and ES cells.

Therapeutic Applications

The method disclosed herein can have a variety of applications. In one embodiment, the method can be used for clinical or therapeutic applications. The method can be used to repair or correct disease-causing genes, as for example a single nucleotide change in sickle-cell disease. The method can be used to correct splice junction mutations, deletions, insertions, and the like in other genes or chromosomal sequences that play a role in a particular disease or disease state.

From the above, the polypeptides according to the invention can be used as a medicament, especially for modulating, activating or inhibiting gene transcription, at the promoter level or through their catalytic domains.

Cas9 or split Cas9 proteins according to the present invention can be used for the treatment of a genetic disease to correct a mutation at a specific locus or to inactivate a gene the expression of which is deleterious. Such proteins can also be used to genetically modify iPS or primary cells, for instance T-cells, in view of injected such cells into a patient for treating a disease or infection. Such cell therapy schemes are more particularly developed for treating cancer, viral infection such as caused by CMV or HIV or self-immune diseases.

General Definitions

In the description above, a number of terms are used extensively. The following definitions are provided to facilitate understanding of the present embodiments.

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or polynucleotide" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By "complementary sequence" is meant the sequence part of polynucleotide (e.g. part of crRNa or tracRNA) that can hybridize to another part of polynucleotides (e.g. the target nucleic acid sequence or the crRNA respectively) under standard low stringent conditions. Such conditions can be for instance at room temperature for 2 hours by using a buffer containing 25% formamide, 4×SSC, 50 mM NaH2PO4/Na2HPO4 buffer; pH 7.0, 5×Denhardt's, 1 mM EDTA, 1 mg/ml DNA+20 to 200 ng/ml probe to be tested (approx. 20-200 ng/ml)). This can be also predicted by standard calculation of hybridization using the number of complementary bases within the sequence and the content in G-C at room temperature as provided in the literature. Preferentially, the sequences are complementary to each other pursuant to the complementarity between two nucleic acid strands relying on Watson-Crick base pairing between the strands, i.e. the inherent base pairing between adenine and thymine (A-T) nucleotides and guanine and cytosine (G-C) nucleotides. Accurate base pairing equates with Watson-Crick base pairing includes base pairing between standard and modified nucleosides and base pairing between modified nucleosides, where the modified nucleosides are capable of substituting for the appropriate standard nucleosides according to the Watson-Crick pairing. The complementary sequence of the single-strand oligonucleotide can be any length that supports specific and stable hybridization between the two single-strand oligonucleotides under the reaction conditions. The complementary sequence generally authorizes a partial double stranded overlap between the two hybridized oligonucleotides over more than 3 bp, preferably more than 5 bp, preferably more than to 10 bp. The complementary sequence is advantageously selected not to be homologous to any sequence in the genome to avoid off-target recombination or recombination not involving the whole donor matrix (i.e. only one oligonucleotide).

By "nucleic acid homologous sequence" it is meant a nucleic acid sequence with enough identity to another one to lead to homologous recombination between sequences, more particularly having at least 80% identity, preferably at least 90% identity and more preferably at least 95%, and even more preferably 98% identity. "Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

Having generally described this invention, a further understanding can be obtained by reference to certain specific examples, which are provided herein for purposes of illustration only, and are not intended to be limiting unless otherwise specified.

EXAMPLES

Example 1: Identification of Conserved Sequence Segments of Cas9 Homologues

In order to increase the efficacy of transfection and vectorization the inventors perform truncations of the protein of Cas9 of *S. pyogenes* (gi|15675041|). The truncated forms of Cas9 will be tested in mammalian cells for efficiency of NHEJ and HR. A first strategy implies a semi rational approach based on the identification of conserved sequence segments of homologues of Cas9 *Pyogenes*. The strategy is based on the use of data derived from sequence features of Cas9 of *pyogenes* i.e. sequence homologues as well as secondary structure predictions and protein domain boundaries predictions.

The sequence of *S. pyogenes* Cas9 belongs to the COG3513 (Predicted CRISPR-associated nuclease, contains McrA/HNH-nuclease and RuvC-like nuclease domain). The alignment of sequence members of COG3513 has been used to build two sequence motifs, each one next to one of the two known catalytic domains RuvC and HNH. The two designed motifs, RuvC motif (D-[I/L]-G-X-X-S-X-G-W-A) (SEQ ID NO: 1) and HNH motif (Y-X-X-D-H-X-X-P-X-S-X-X-X-D-X-S) (SEQ ID NO: 2) have been used to extract all the protein sequences presented in UniProtKB database using the ScanProsite tool (de Castro, Sigrist et al. 2006).

The use of the RuvC motif (D-[I/L]-G-X-X-S-X-G-W-A) (SEQ ID NO: 1) allows the extraction of 358 sequences and the use of HNH motif (Y-X-X-D-H-X-X-P-X-S-X-X-X-D-X-S) (SEQ ID NO: 2) allows the extraction of 187 sequences. All the extracted sequenced have been inspected looking for putative cas9 homologues with interesting features as smaller size, different origins and/or different organization of the locus. The homologues for each domain have been analysed separately and a few of them have been extracted and aligned. The boundaries of each domain have been identified.

RuvC-Like Domain

Among the 358 sequences found using the RuvC sequence motif, eight sequences (SEQ ID NO: 5 to SEQ ID NO: 12) have been extracted and aligned to the original sequence of *S. pyogenes* Cas9 (SEQ ID NO: 3). The alignments have been made using standard multiple sequence alignment software (DIALIGN 2.2.1 software) (Morgenstern 2004). The alignments of the Cas9 homologues are presented in Table 1 as follows:

| | | | |
|---|---|---|---|
| 1) | *S. pyogenes* Cas9 | (SEQ ID NO: 4) | 1368 amino acids (AA) |
| 2) | D8IJI3_LACSC | (SEQ ID NO: 5) | 183 AA |
| 3) | F0K1W4_LACD2 | (SEQ ID NO: 6) | 669 AA |
| 4) | E1NX15_9LACO | (SEQ ID NO: 7) | 142 AA |
| 5) | C5F1Z4_9HELI | (SEQ ID NO: 8) | 344 AA |
| 6) | F3ZS86_9BACE | (SEQ ID NO: 9) | 349 AA |
| 7) | H1D479_9FUSO | (SEQ ID NO: 10) | 198 AA |
| 8) | K1M766_9LACO | (SEQ ID NO: 11) | 857 AA |
| 9) | Q7VG48_HELHP | (SEQ ID NO: 12) | 131 AA |

The protein secondary structure of RuvC-like domain of Cas9 has been predicted using the PSIPRED secondary structure prediction method (Jones 1999; Buchan, Ward et al. 2010) (See Table 2).

Using this multiple sequence alignment and the prediction derived from DoBo server (Eickholt, Deng et al. 2011) together with the secondary structures prediction we can assume that the RuvC-like domain of *S. pyogenes* Cas9 extends until position 166G (SEQ ID NO: 2).

HNH Domain

Among the 187 sequences found using the HNH sequences motif (Y-X-X-D-H-X-X-P-X-S-X-X-X-D-X-S), nine sequences (SEQ ID NO: 14 to 22) have been extracted and aligned to the original sequences of *S. pyogenes* Cas9 (SEQ ID NO: 3) using DIALIGN 2.2.1 software as described above (see Table 3). The alignments of the Cas9 homologues are presented in Table 3 as follows:

| | | | |
|---|---|---|---|
| 1) | D8IJI4_LACSC | (SEQ ID NO: 14) | 897 AA |
| 2) | F0K1W6_LACD2 | (SEQ ID NO: 15) | 544 AA |
| 3) | D4FGK2_9LACO | (SEQ ID NO: 16) | 534 AA |
| 4) | E1NX12_9LACO | (SEQ ID NO: 17) | 667 AA |
| 5) | E7NSW3_TREPH | (SEQ ID NO: 18) | 591 AA |
| 6) | H1D477_9FUSO | (SEQ ID NO: 19) | 387 AA |
| 7) | C2KFJ4_9LACO | (SEQ ID NO: 20) | 544 AA |
| 8) | K1MRU9_9LACO | (SEQ ID NO: 21) | 206 AA |
| 9) | E3ZTQ9_LISSE | (SEQ ID NO: 22) | 874 AA |
| 10) | *S. pyogenes* Cas9 | (SEQ ID NO: 3) | 1368 AA |

The protein secondary structure of HNH domain of Cas9 has been predicted using the PSIPRED secondary structure prediction method (Jones 1999; Buchan, Ward et al. 2010) (See Table 4).

The boundaries of the HNH domain has been identified using the multiple sequence alignment of the *S. pyogenes* Cas9 homologues and DoBO server (Eickholt, Deng et al. 2011) and secondary structure prediction server (psipred). Two versions of Cas9 HNH domains have been predicted. The N-terminus of each HNH domain version corresponds to P800, while the C-terminus corresponds to the Y981 for the shorter version (SEQ ID NO: 23) or G1055 for the longer version (SEQ ID NO: 13). A Cas9 comprising the new RuvC domain identified (SEQ ID NO: 4) and one of the two versions of the HNH domains (SEQ ID NO: 13 and SEQ ID NO: 23) will be engineered and its activity will be tested.

Example 2: Identification of Shorter Cas9 Homologues and Digestion of the C-Terminal Domain of Cas9

The present study further allows identifying four putative natural Cas9 homologues with shorter sequence (SEQ ID NO: 26 to SEQ ID NO: 29). These natural shorter Cas9 versions have been aligned with the *S. pyogenes* Cas9 using DIALIGN 2.1.1 software as described above. The alignments of the shorter Cas9 homologues are presented in Table 5 as follows:

| | | | |
|---|---|---|---|
| 1) | D4IZM9_BUTFI | (SEQ ID NO: 26) | 765 AA |
| 2) | Q9CLT2_PASMU | (SEQ ID NO: 27) | 1056 AA |
| 3) | E0G5X6_ENTFL | (SEQ ID NO: 28) | 936 AA |
| 4) | E0XXB7_9DELT | (SEQ ID NO: 29) | 1011 AA |
| 5) | *S. pyogenes* Cas9 | (SEQ ID NO: 3) | 1368 AA |

The protein secondary structure of shorter Cas9 has been predicted using the PSIPRED secondary structure prediction method (Jones 1999; Buchan, Ward et al. 2010) (See Table 6).

For all the shorter sequence homologs (D41ZM9_BUTFI, Q9CLT2_PASMU, E0G5X6_ENTFL, E0G5X6_ENTFL; SEQ ID NO: 26 to SEQ ID NO: 29) position T956 seems to be quite conserved anyway looking at the secondary structure prediction of Cas9 in this zone Y943 seems to be more a better position to cut the C-terminus of Cas9 of *Pyogenes*.

To perform a progressive enzymatic digestion we will use a modified protocol described by (Lutz, Ostermeier et al. 2001). Through the use of exonuclease and heat inactivation we will create an incremental truncation library of the C-terminal of Cas9. Approximately we will create libraries of fragments of Cas9 starting from 1364 up to ~900 aa.

Three shorter version of the entire sequence of Cas9: Cas9_delta943 (SEQ ID NO: 31), Cas9_delta980 (SEQ ID NO: 32) and Cas9_delta1055 (SEQ ID NO: 33) will be engineered (see FIG. 1).

The new cas9 scaffolds obtained with the two different strategies will be tested in mammalian cells using the sgRNA chimera and the PAM specific for *S. pyogenes* already described in (Mali, Yang et al. 2013)

Example 3: Identification of the Residues Involved in the DNA/RNA Binding Specificity of S. pyogenes Cas9 and Homologues Thereof In the present study, the identification of Cas9 residues involved in the binding of the guide RNA and the PAM motif will allow to engineer new Cas9 scaffolds and thus modulate affinity for the selected target.

Using the multiple sequence alignment of Cas9 homologues as described above, the inventors identified the most conserved regions in terms of primary sequence of S. pyogenes Cas9. The inventors matched this data with results derived from servers capable of predicting DNA and RNA binding residues from sequence features (i.e. BindN) (Wang and Brown 2006). Contemporaneously the solvent accessibility and secondary structure prediction of the primary sequence of Cas9 has been used to identify the most exposed residues on the surface of the protein. The predicted DNA and RNA binding region on S. pyogenes Cas9 are listed in Table 7. The predicted DNA and RNA binding regions on Cas9 homologues are represented in Table 1, 3 and 5 (grey highlighted sequences).

Figure 2:
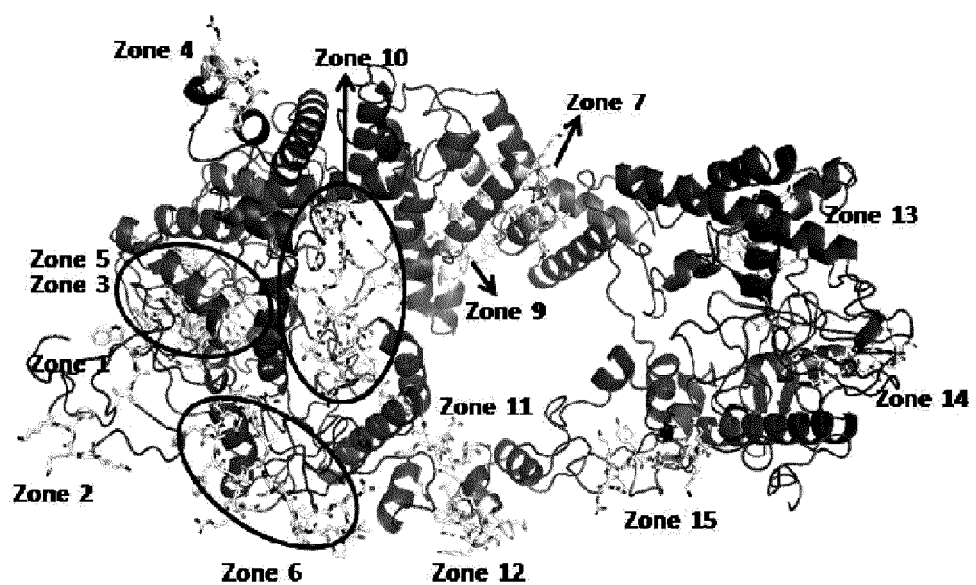
FIGS. 2 and 3: Fifteen DNA/RNA binding regions mapped in the 3D model of the sequence of *S. pyogenes*.
Figure 3:
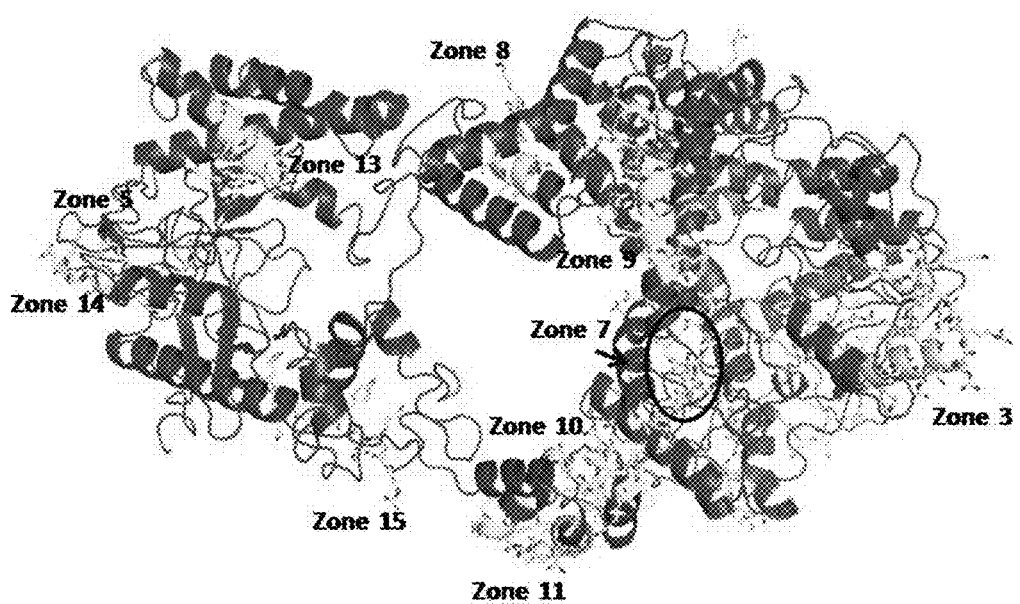

Structure of S. pyogenes Cas9 was predicted using automated software. In FIG. 2 and FIG. 3, the inventors mapped the 15 predicted DNA/RNA binding regions described above on the best 3-dimensional model output to determine the residues susceptible to be in contact with DNA or RNA.

A multiple sequence alignment between Cas9 of S. pyogenes (SEQ ID NO: 62) and S. Thermophilus (SEQ ID NO: 64) and the sequence of two pdb structures of RuvC domain of E. Coli and T. Thermophilus (SEQ ID NO: 63 and SEQ ID NO: 61) has also been built using clustalw (see Table 8).

The multiple sequence alignment of the two RuvC domains with the two sequences of Cas9 can point out the stretch of residues not presented in the RuvC domains that could be responsible of the specificity of the PAM. The RuvC domains have a specificity of cleavage which is not present in Cas9, on the contrary the stretch of residues 38T-57E and T146-L169 (which are not conserved in the RuvC domains) could represents the zone responsible of the specificity of the PAM. In particular the differences of sequences between Cas9 of S. pyogens and S. Thermophilus in these two zones could hint to the specificity of each PAM. The residues 39-DRHS-42 and E57 and D147 and I154 are the principal differences between the Cas9 of S. pyogenes and S. Thermophilus and finally they could be the positions responsible for the PAM specificity. Also interestingly are the positions 173D-174L and 177D which are highly exposed and on the same loop of two key residues for the activity of RuvC domain of E. Coli: lys 107 and lys 118 (both positions are not conserved in Cas9).

Collecting all these different sources of data allows the inventors to pinpoint the most probable DNA/RNA binding segments of S. pyogenes Cas9. In a first approach, the inventors will create independent libraries (from 3 to 5 amino acids) for each DNA/RNA binding region. In parallel, the inventors will select cluster of amino acids, based on their 3D localization, belonging to different zones but lying on possible patch of charge surface.

In particular to decipher Cas9 residues involved in the recognition of the PAM motif, the inventors will create Cas9 variants libraries comprising randomized residues at each protein seed positions (i.e. with a NVK degenerate codes). The Cas9 variants libraries will be further screened against artificial synthesized targets. As a first set up, the synthesized targets will comprise 20 constant nucleotides necessary for the complex sgRNA::DNA while the base responsible for the recognition of the PAM motif will be modified. Currently the number of PAM nucleotides specifically recognized by S. pyogenes Cas9 were restricted to 2 (NGG; (Mali, Yang et al. 2013)). Here, the inventors plan to increase or suppress the number of nucleotides specifically recognized by Cas9 as a way to modulate its specificity.

The "non natural PAM" will be constituted of at least 5 bases; they will be treated as 3 sliding windows of three bases each starting from position 1 to 5. Finally the cas9 libraries will be screened against each set of 64 targets constituting the 3 different sliding windows.

All the Cas9 constructs will be analysed in yeast with a high-throughput screening platform. Once identified a "non natural PAM", different rounds of refinements will be performed in order to assess the synergistic effects of the contemporary mutation of more than one protein seeds.

Each "non natural PAM" will be also tested on sets of new targets harboring the most dissimilar 20 bases RNA target recognitions. Complementary to this in vivo approach we will also set up experiments of high throughput in vitro protein-DNA interaction using methodology as i.e. Bind-n-Seq. The best combinations of "non natural PAM" and protein constructs will be tested in mammalian cell. Once identified on Cas9 of pyogenes the zone responsible for the recognition of the nucleic acid they will be also plotted on the sequences of chosen homologues and tested in eukaryotic cells.

Example 4: Creation of a Split Cas9 RNA Guided Nuclease

The sequence of Cas9 of S. Pyogenes belongs to the COG3513 (Predicted CRISPR-associated nuclease, contains McrA/HNH-nuclease and RuvC-like nuclease domain. The alignment of sequence members of COG3513 has been used to build two sequence motives (each one next to one of the two known catalytic domains: RuvC and HNH). The two sequence motives have been used to extract (using PROSITE) all the protein sequences presented in Uniprot bearing each of the two domains. The use of the RuvC motif (D-[IL]-G-x(2)-S-x-G-W-A) allows the extractions of 358 sequences while the use of HNH motif (Y-2x-D-H-2x-P-x-S-3x-D-x-S) allows the extraction of 187 sequences.

Between the sequences extracted using the RuvC motif eight sequences derived from different organisms were selected. These RuvC-like sequences share interesting features as such as to be present in a short truncated form (if they are compared to the Cas9 of S. Pyogenes composed of 1368 aa) and also to be related to a putative independent HNH domains.

Six of these eight proteins are annotated as uncharacterized proteins: D8IJI3_LACSC from *Lactobacillus salivaris* (SEQ ID NO: 5), F0K1W4 from *Lactobacillus Delbrueckii* (SEQ ID NO: 6), Q7VG48 from *Helicobacter Hepaticus* (SEQ ID NO: 12) and E9S0G6 from *Treponema Denticola*

(SEQ ID NO: 51) and C5F1Z4 from *Helicobacter Pullorum* (SEQ ID NO: 8). Two RuvC-like domains are annotated as Crispr related proteins: H1D479 from *Fusobacterium Necrophorum* (SEQ ID NO: 10) and K1M766 from *Lactobacillus Crispatus* (SEQ ID NO: 11).

The finding of these naturally occurring independent RuvC/HNH like domains has prompted us to engineer the wild type sequence of *S. Pyogenes* Cas9 to create split cas9 proteins. The wild type sequence of *S. Pyogenes* Cas9 has been divided into two separate polypeptide chains (RuvC and HNH like domains) that co-transfected could assemble to reconstitute the entire wild type sequence of *S. Pyogenes* Cas9. In order to predict the optimal breaking position for the *S. Pyogenes* Cas9 sequence we have built a multiple sequence alignment between the above described eight sequences and wild type sequences of Cas9 of *S. Pyogenes* and *S. Thermophilus* together with the PDB structure of the RuVC domain of *E. coli* (Pdbcode 4EPA) (Table 9). We have integrated these informations with the prediction of secondary structure elements (using PSIPRED) for the sequence of Cas9 *S. Pyogenes* (Table 10).

We have chosen to create a split Cas9 dividing the sequence of *S. Pyogenes* Cas9 in two independent polypeptide chains using as possible breaking point the position: G247. Specifically we have created two separated domains of cas9 of *S. Pyogenes*. The domain N-terminal consists of the residues from position 1 to position 247 (SEQ ID NO: 52) and the C-terminal comprehends the residues from amino acid 248 to 1368 (SEQ ID NO: 53).

A S-Tag plus one NLS was fused to the 5' terminus of the split RuvC domain using standard biological tools yielding pCLS24814 plasmid (SEQ ID NO: 54). A 2NLS-BFP-HA-Tag was fused to the 3' terminus of the split HNH domain, then the first amino acid of the split HNH domain was mutated from Leu to Val to have a better Kozak consensus sequence yielding pCLS24813 (SEQ ID NO: 55; pCLS24813).

The nuclease activity of these two split domains with the guide RNA was tested on endogenous GFP_C9_T01 target (SEQ ID NO: 56) in CHO-KI (π10) cell. pCLS24814 and pCLS24813 were co-transfected at three different doses. Positive control corresponds to the transfection of the wild type Cas9 of *S. Pyogenes* with guide RNA (SEQ ID NO: 57; pCLS22972) and control corresponds to the transfection of each split domain separately in presence of the guide RNA.

Figure 4:
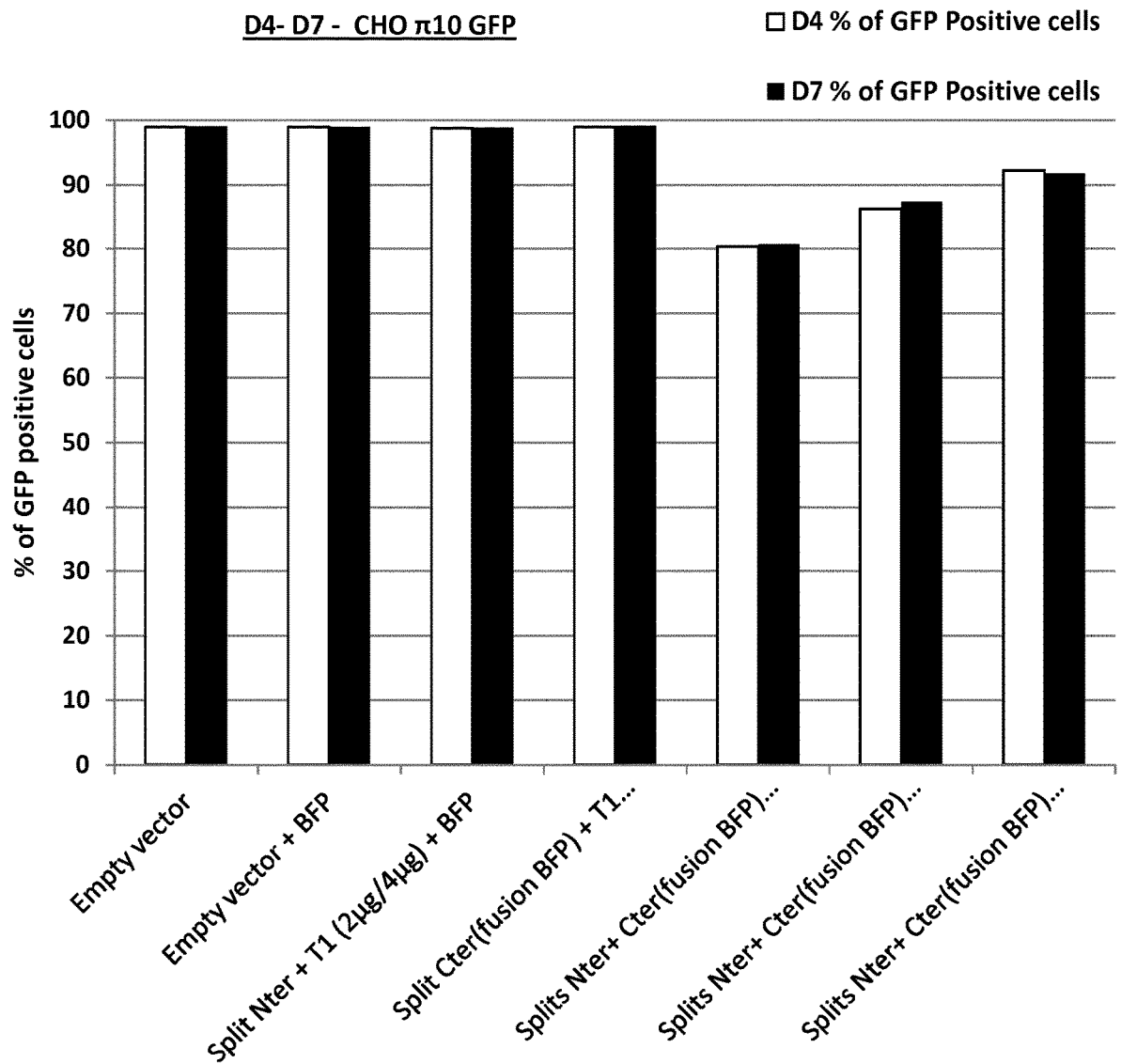
FIG. 4: Nuclease activity of the split Cas9 domains measured as a reduction in GFP by flow cytometry (Macsquant) at day 4 and day 7 post-transfection. The values are reported for each single split domains or for the two co-transfected split domains.

Nuclease activity of the split cas9 domains was measured as a reduction in GFP fluorescence via flow cytometry using MACSQuant Analyzer (Myltenyi Biotec.) at four and seven days post transfection. The results clearly show that the co-transfection of the two split domains induce a reduction of the percentage of GFP positive cells which is stable over the time (from D4 to D7)(FIG. 4).

Figure 5:
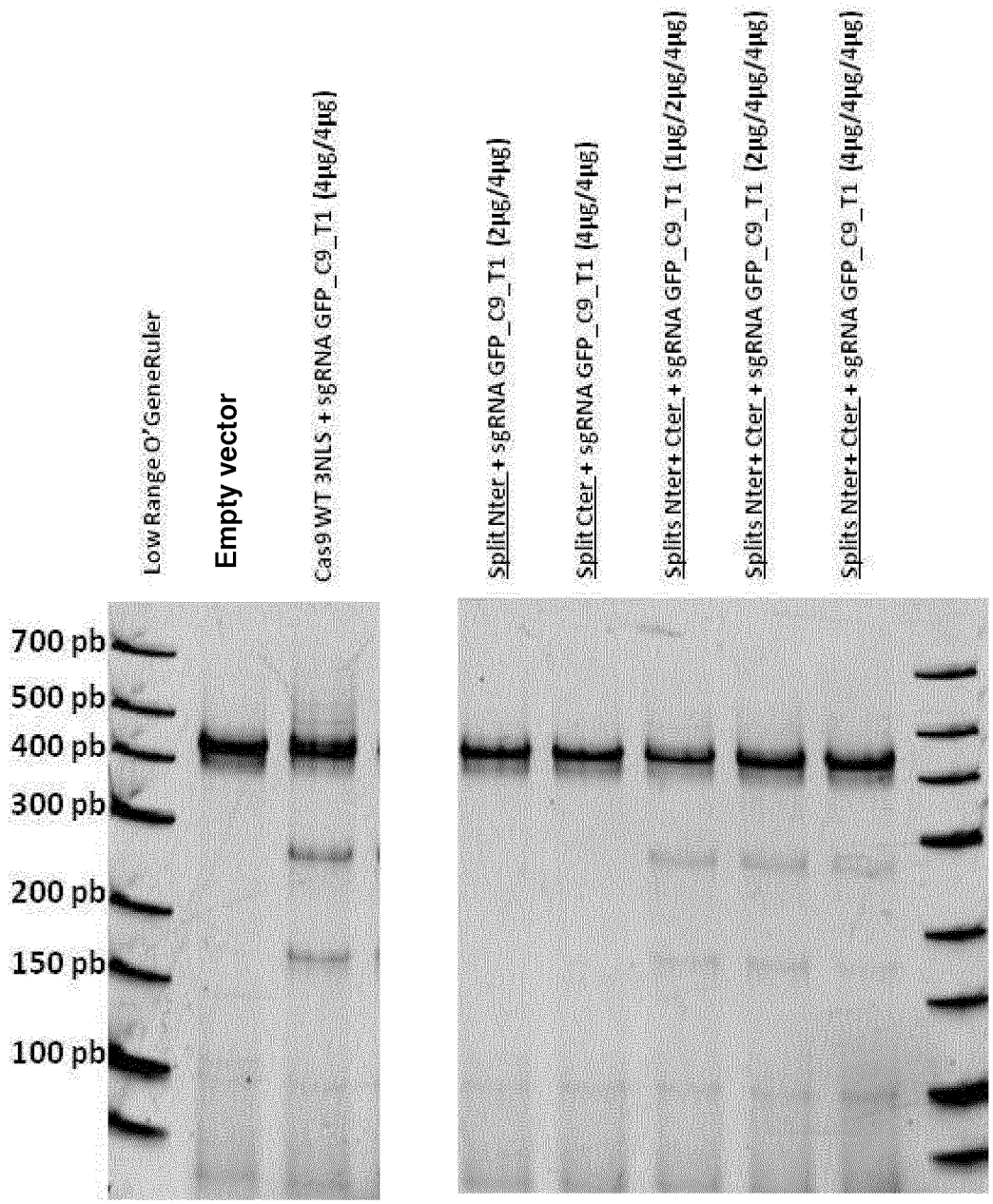
FIG. 5: Nuclease activity of the split Cas9 domains on GFP target tested using EndoT7 assay.

The nuclease activity of the split cas9 was also tested using a T7 Endo assay (FIG. 5). As shown in FIG. 5, co-transfection of both split domains (at the three different doses) induces cleavage of the DNA. Our results show that co-transfection of both split domains efficiently cleave the DNA target with no evident toxicity over the time.

Figure 6:
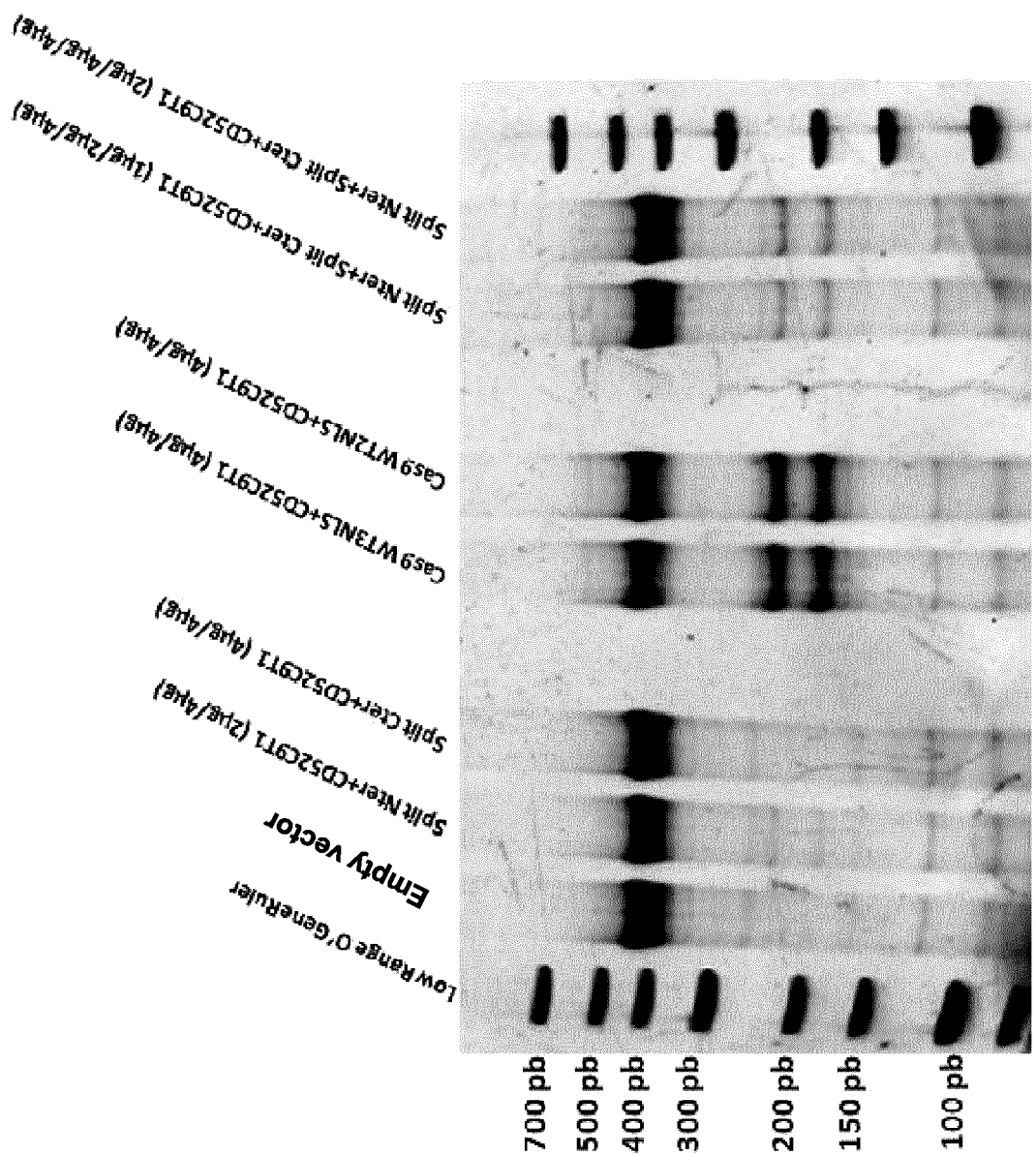
FIG. 6: Nuclease activity of the split Cas9 domains on CD52 target gene tested using EndoT7 assay.

The nuclease activity of these two split domains together or each split separately with the guide RNA was also tested on endogenous CD52 target in CHO-KI (π10) cell. The nuclease activity of the split cas9 was tested using a T7 Endo assay (FIG. 6). As shown in FIG. 6, co-transfection of both split domains induces cleavage of the DNA. Surprisingly, the transfection of RuvC split Cas9 domain (N-terminal domain) alone shows the same cleavage profile. Our results show that the N-terminal split domain is active independently of the C-terminal split domain and can cleave the target nucleic acid sequence.

Material and Methods

CHO-KI (π10) cells containing the chromosomally integrated GFP reporter gene including the guide RNA recognition sequence (SEQ ID NO: 56), were cultured at 37° C. with 5% $CO_2$ in F12-K complete medium supplemented with 2 mM I-glutamine, penicillin (100 IU/ml), streptomycin (100 µg/ml), amphotericin B (Fongizone: 0.25 µg/ml, Life Technologies,) and 10% FBS. Cell transfection was performed according to the manufacturer's instructions using the Nucleofector apparatus (Amaxa, Cologne, Germany). Adherent CHO-KI cells were harvested at day 0 of culture, washed twice in phosphate-buffered saline (PBS), trypsinized, and resuspended in T nucleofection solution to a concentration of $1 \times 10^6$ cells/100 µL.

We performed the co-transfection of the two split domains at three different doses (we keep constant the quantity of the guide RNA encoding plasmide at 4 ug). As first dose we used 1 ug for the N-terminal split and 2ug for the C-terminal plasmid; we also double the dose of the two split domains at 2ug and 4 ug and as third dose we used an equal quantity for the two split domains plasmids at 4 ug.

For each point of transfection we mixed the chosen quantity of the vectors for the two splits domain with the 4 µg of guide RNA plasmid GFP_C9_T01 (SEQ ID NO: 58) with 0.1 mL of the CHO-KI (π10) cell suspension (T Nucleofection solution). We transferred the mix to a 2.0-mm electroporation cuvette and nucleofected using program U23 of Amaxa Nucleofector apparatus.

250 ng of BFP expression plasmid have been added to the samples (besides to the one with the C-terminal split domain) in order to estimate the transfection efficiency. Maximum 20 min after nucleofection, 0.5 mL of prewarmed CHO-K1 medium was added to the electroporation cuvette. For each sample cells were then divided into two parts to seed two Petri dish (10 ml F12-K) and cultured at 37° C. under 5% $CO_2$ as previously described.

On day 4 post-transfection, cells were washed twice in phosphate-buffered saline (PBS), trypsinized, resuspended in 5 mL medium and percentage of GFP negative cells (200 µl at 2×105 cells/mL). The percentage of GFP negative cells was monitored at D4 and D7 (FIG. 4) by flow cytometry MACSQuant Analyzer (Myltenyi Biotec.). Four days post-transfection (day 4), genomic DNA was extracted and the locus of interest was amplified with locus primers 1 and 2 (SEQ ID NO: 59 and 60). Amplicons were analyzed by EndoT7 assay according to the protocol described in (Reyon, Tsai et al. 2012) see FIG. 5.

TABLE 1

Multiple sequence alignment of RuvC domain of Cas9 homologues: D8IJI3_LACSC (SEQ ID NO: 4), F0K1W4_LACD2 (SEQ ID NO: 5), E1NX15_9LACO (SEQ ID NO: 6), C5F1Z4_9HELI (SEQ ID NO: 7), F3ZS86_9BACE (SEQ ID NO: 8), H1D479_9FUSO (SEQ ID NO: 9), K1M766_9LACO (SEQ ID NO: 10), Q7VG48_HELHP (SEQ ID NO: 11) with *S. pyogenes* Cas9 (SEQ ID NO: 3).

```
Cas9 pyogenes    1   ---MDKKYSI GLDIGTNSVG WAVITDEYKV PSKKFkvlgn tdrhsikKNL
D8IJI3_LACSC     1   m----ERYHI GLDIGTSSIG WAVIGDDFKI KRKKG----- -------KNL
F0K1W4_LACD2     1   MAKP-KDYTI GLDIGTNSVG WVVTDDQNNI LRIKG----- -------KKA
E1NX15_9LACO     1   ---MNNNYYL GLDLGTNSVG WAVTDDHYNI IKFHG----- -------KHM
C5F1Z4_9HELI     1   M-K-----IL GFDIGIASIG WAFVENGE-- -----L---- ---------KD
F3ZS86_9BACE     1   mkK-----IL GLDIGTNSVG WAVVNTNQeg epsqI----- ---------EK
H1D479_9FUSO     1   MKKF-ENYYL GLDIGTSSIG WAVTNSQYDI LKFNG----- -------KYM
K1M766_9LACO     1   mtkLNNEYMV GLDIGTNSCG WVATDFDNNI LKMHG----- -------KRA
Q7VG48_HELHP     1   M-R-----IL GFDIGITSIG WAYVESNE-- -----L---- ---------KD Cas9 pyogenes    48  IGALLF---- ---------D SGETAEATRL KRTARRRYTR RKNRICYLQE
D8IJI3_LACSC     35  IGVRLF---- ---------K EGDTAAERRS FRTQRRRLNR RKWRLKLLEE
F0K1W4_LACD2     38  IGARLF---- ---------T EGKVAAERRS FRTTRRRLSR RRWRIKMLEE
E1NX15_9LACO     36  WGMRLF---- ---------E EAETAKDRRL HRQARRRRQR LVERINLLEE
C5F1Z4_9HELI     26  CGVRIFTKAE NPK------T GDSLAMPRRE ARSVRRRLAR RKGRLETLKR
F3ZS86_9BACE     33  LGSRIIPMSQ DildkfgqgQ TVSSTASRTD YRGIRRLRER SLLRRERLHR
H1D479_9FUSO     38  WGTRLF---- ---------P EANTAQERRI HRSSRRRLKR RKERIQILQM
K1M766_9LACO     39  LGSHLF---- ---------D EGVSAADRRA FRTTRRRIKR RKWRLKLLEE
Q7VG48_HELHP     26  CGVRIFTKAE NPK------N GDSLAAPRRE ARGARRRLAR RKARLNAIKR Cas9 pyogenes    85  IFSNE----- -------MAK VD-------- ---------- ----------
D8IJI3_LACSC     72  IFDPY----- -------MAE VD-------- ---------- ----------
F0K1W4_LACD2     75  LFDEE----- -------IAK VD-------- ---------- ----------
E1NX15_9LACO     73  LFDKE----- -------ISK VD-------- ---------- ----------
C5F1Z4_9HELI     70  LLAKE----- -------WDL CY-------- ---------- ----------
F3ZS86_9BACE     83  VLhildflpk hyadsigWDp rnsktygkfl pgtevklawv ptadghqflf
H1D479_9FUSO     75  LFDKE----- -------IAK ID-------- ---------- ----------
K1M766_9LACO     76  IFDEE----- -------MAK VD-------- ---------- ----------
Q7VG48_HELHP     70  LLCKE----- -------FEL nln------- ---------- ----------

Cas9 pyogenes    95  -DSFFHRLEE S-FLVEEDKK herhpifgni vdeva--YHE KYPTIYHLRK
D8IJI3_LACSC     82  -EYFFARLKE S-NLSPKDSN KKYLGSLlfp -DISDSNFYD KYPTIYHLRR
F0K1W4_LACD2     85  -PSFFARLHE S-WISPKDKR KRYSAIVFPS PEE-DKKFHE SYPTIYHLRD
E1NX15_9LACO     83  -QGFFARKKE S-DLHFEDKT TKSEYALFND KSYTDRDYYK QYPTIFHLIM
C5F1Z4_9HELI     80  -EDYIAADGE LPKAFmgknl tnp------- ---------- -----YVLRY
F3ZS86_9BACE     133 ySTYLEMLED L-KQTQAQLF ETSQTPVPLD w--------- ---TIIYLRK
H1D479_9FUSO     85  -SGFFQRLKD S-KYYKEDKT EKQTNSIFHD KDYSDKEYHQ KFPTIYHLRK
K1M766_9LACO     86  -PNFFARLKE S-GLSPLDTR KNVSSIVFPT KKM-DKQFYK KFPTIYHLRN
Q7VG48_HELHP     81  --DYLANDGE LPKAYQTSKD TKSPYELY-- ---------- ---TAFHWII

*
Cas9 pyogenes    141 KLVDSTDKAD LRLIYLALAH MIKFRGHFLI EGDLNpdn-- ----------
D8IJI3_LACSC     129 DLMEKDKKFD LREIYLAIHH IVKYRGNFL- ---------- ----------
F0K1W4_LACD2     132 KLMKDDQKHD IREIYIAVHQ MIKARGNFL- ---------- ----------
E1NX15_9LACO     131 DLIENDKKgi yv-------- ---------- ---------- ----------
C5F1Z4_9HELI     107 EALQRLLSK- -EELVRVVLH IAKHRGYGN- ---------- ----------
F3ZS86_9BACE     170 KALTQPITK- -HELAWLLLH FNTKRGYYQR RGELEdtptd klveyhalkv
H1D479_9FUSO     133 FLLEGNKPKD IRFVYLALHH ILTHRGHFLf pdm------- ----------
K1M766_9LACO     133 ALMKQDKKFD LRAIYIAIHH IVKYRGNFL- ---------- ----------
Q7VG48_HELHP     114 fa-------- ---------- ---------- ---------- ----------
```

\* corresponds to the predicted 3'-end amino acid (G166) of the *S. pyogenes* Cas9 RuvC-like domain.
Grey highlighted sequence: predicted DNA/RNA binding region (see example 3).

TABLE 2

Secondary structure predictions for the RuvC domain and amino acids sequence of the RuvC domain of the *S. pyogenes* Cas9 (SEQ ID NO: 12).

Sequence of *S. pyogenes* Cas9 (SEQ ID NO: 12)
MDKKYSIGLDIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRG Secondary structure Cas9 of *Pyogenes*
CCCCSSSSSSCCCCSSSSSSCCCCCCCCCCCCCCCCCCCCCCCSSSS
SSCCCCCCHHHHHHHHHHHHHHHHHHHHHHHHHHHHCCCCCHHHHH
HCCCCCCCCCCCCCCCCCCCHHHHHHHHCCCHHHHHHHHCCCCCCC
HHHHHHHHHHHHHHCC H represents helix, S represents sheet and C represents coil.

TABLE 3

Multiple sequence alignment of HNH domains of Cas9 homologues:
D8IJI4_LACSC (SEQ ID NO: 13), F0K1W6_LACD2 (SEQ ID NO: 14), D4FGK2_9LACO (SEQ ID NO: 15), E1NX12_9LACO (SEQ ID NO: 16), E7NSW3_TREPH (SEQ ID NO: 17), H1D477_9FUSO (SEQ ID NO: 18), C2KFJ4_9LACO (SEQ ID NO: 19), K1MRU9_9LACO (SEQ ID NO: 20), E3ZTQ9_LISSE (SEQ ID NO: 21) with Cas9 *Pyogenes* (SEQ ID NO: 3).

```
                              *
D8IJI4_LACSC    510  -RKGKSKLTN TRYKKISETY EKITDELISE YELGKLQSKL DSKANNmr--
F0K1W6_LACD2      5  ---------- ---------- ---------- ---------- ----------
D4FGK2_9LACO      1  ---------- ---------- ---------- ---------- ----------
E1NX12_9LACO     82  SKEDHPKRKL SRKADLKQVY KDSKKQIISI IGKDKYQDLS NELDNK---D
E7NSW3_TREPH      4  GKEAEKGRTS SRYASIKALY ENCKQDLADY DA-------- -VLEQFkseE
H1D477_9FUSO    258  QEDMKKERKE SRKSTFLTLY KSIKEEGRDW IK-------- -EIENW---S
C2KFJ4_9LACO      1  ---------- ---------- ---------- ---------- ----------
K1MRU9_9LACO      1  ---------- ---------- ---------- ---------- ----------
E3ZTQ9_LISSE    309  ENQTTGKGKN NSKPRFTSLE KAIKELGSQI LK-------- -EHPT----D
Cas9 Pyogenes   766  ENQTTQKGQK NSRERMKRIE EGIKELGSQI LK-------- -EHPV----E D8IJI4_LACSC    557  -------DIYY LYFMQLGRDM YTGEKINIDE L----HQYYD IDHIFPRSFI
F0K1W6_LACD2      5  ---------- ---------- ---------- -----AD-YD VDHIMPQSFV
D4FGK2_9LACO      1  ---------- -------RDA YTDKPINIDE V----SQYYD IDHILPQSFI
E1NX12_9LACO    129  DRDLRWDNLY LYYTQLGRSM YSLKPIDISE LMNKNL--YD IDHIYPRSKI
E7NSW3_TREPH     45  PLRLRSDKLY LYYTQLGRCM YTGRVIDIDR LMSDNSA-YD IDHIYPRSKI
H1D477_9FUSO    296  DSEFRSKKLY LYYTQMGKCM YTGEKISLDQ LFNKNI--YD IDHIYPRSKI
C2KFJ4_9LACO      1  -------KYY LYFMQLGRDA YTGKPINIDE V----SQYYD IDHILPQSFI
K1MRU9_9LACO      1  ---------- ---MQLGRDA YTGKPINIDE V----SQYYD IDHILPQSFI
E3ZTQ9_LISSE    346  NQGLKNDRLY LYYLQNGKDM YTGQELDIHN L----SN-YD IDHVVPQSFI
Cas9 Pyogenes   803  NTQLQNEKLY LYYLQNGRDM YVDQELDINR L----SD-YD VDHIVPQSFL D8IJI4_LACSC    597  KDNSLNNRVL TRKEINNNEK adrtaadlya v--------KM GDFWRKLRKQ
F0K1W6_LACD2     19  KDDSLDNRVL VARAVNNQKS DKVPALLFGN KVVADLGITV REMWDKWQKL
D4FGK2_9LACO     30  KDDSLNNRVL VAKPINNGKS DGVPLKLFGD NLATGLGITV KQMWNNWADK
E1NX12_9LACO    177  YDDSIENRVL VEKELNVKKS DIYPIsd-AN IIPQKIKGQV ESFWKMLYDH
E7NSW3_TREPH     94  KDDSLTNRVL VVKDANQDKR DEplSP-QIQ D-------KQ KGFWDFLKHN
H1D477_9FUSO    344  KDDSIENIVL VKRNINAKKT DEYPLErNIQ Q-------KQ HDFWKMLHSK
C2KFJ4_9LACO     40  KDDSLNNRVL VAKPINNGKS DGVPLKLFGD NLATGLGITV KQMWNNWADK
K1MRU9_9LACO     34  KDDSLNNRVL VAKPINNGKS DGVPLKLFGD NLATGLGITV KQMWNNWADK
E3ZTQ9_LISSE    391  TDNSIDNRVL ASSAANREKG DNVPSL-EVV R-------KR KVYWEKLYQA
Cas9 Pyogenes   848  KDDSIDNKVL TRSDKNRGKS DNVPSE-EVV K-------KM KNYWRQLLNA D8IJI4_LACSC    640  GLITEKKYKN LLT--RTDSI DKYTKQSFIK RQLVETSQVV KMAANILQDK
F0K1W6_LACD2     69  GMISKRKLSN LLT--DPDAL TEYRAQGFIR RQLVETSQVI KLTATILQSE
D4FGK2_9LACO     80  GLINKAKQNN LFL--DPENI NKHQASGFIR KQLVETSQII KLATTILQAE
E1NX12_9LACO    226  KLIGDKKYAR LIR--SK-AF TDDELAGFIA RQLVETRQAT KETADLLKRL
E7NSW3_TREPH    136  NFISIEKYER LTY--RG-YF TEEMLSGFIA RQLVETRQGT KTAGQILEQL
H1D477_9FUSO    387  N--------- ---------- ---------- ---------- ----------
C2KFJ4_9LACO     90  GLINKAKQNN LFL--DPENI NKHQASGFIR KQLVETSQII KLATTILQAE
K1MRU9_9LACO     84  GLINKAKQNN LFL--DPENI NKHQASGFIR KQLVETSQII KLATTILQAE
E3ZTQ9_LISSE    433  KLMSKRKFDY LTKAERG-GL TEADKARFIH RQLVETRQIT KNVANILHQR
Cas9 Pyogenes   890  KLITQRKFDN LTKAERG-GL SELDKAGFIK RQLVETRQIT KHVAQILDSR
                                                                          *
```

TABLE 3-continued

Multiple sequence alignment of HNH domains of Cas9 homologues:
D8IJI4_LACSC (SEQ ID NO: 13), F0K1W6_LACD2 (SEQ ID NO: 14), D4FGK2_9LACO
(SEQ ID NO: 15), E1NX12_9LACO (SEQ ID NO: 16), E7NSW3_TREPH (SEQ ID NO:
17), H1D477_9FUSO (SEQ ID NO: 18), C2KFJ4_9LACO (SEQ ID NO: 19),
K1MRU9_9LACO (SEQ ID NO: 20), E3ZTQ9_LISSE (SEQ ID NO: 21) with
Cas9 Pyogenes (SEQ ID NO: 3).

```
D8IJI4_LACSC    688  YS--------  ---NTKIIEV  RARLNSDLRK  EYELIKNREV  NDYHHAIDGY
F0K1W6_LACD2    117  PP--------  ---DSKIIEV  PAKYNSIVRK  QFDLYKSREV  NDPHHAIDAY
D4FGK2_9LACO    128  YP--------  ---KTKIIVV  KASSNHYLRN  EFDLYKSREV  NDYHHAIDAY
E1NX12_9LACO    273  CP--------  ---KSRIVYA  KAQNASIFRQ  KFDIPKSRTI  NDLHHAQDAY
E7NSW3_TREPH    183  YP--------  ---DSTVVYC  KAANTSEFRQ  KFNLIKCREI  NDLHHAHDAY
H1D477_9FUSO    388  ----------  ----------  ----------  ----------  ----------
C2KFJ4_9LACO    138  YP--------  ---KTKIIVV  KASSNHYLRN  EFDLYKSREV  NDYHHAIDAY
K1MRU9_9LACO    132  YP--------  ---KTKIIVV  KASSNHYLRN  EFDLYKSREV  NDYHHAIDAY
E3ZTQ9_LISSE    482  FNCKKDESGN  VIEQVRIVTL  KAALVSQFRK  QFQLYKVREV  NDYHHAHDAY
Cas9 Pyogenes   939  MNTKYDENDK  LIREVKVITL  KSKLVSDFRK  DFQFYKVREI  NNYHHAHDAY D8IJI4_LACSC    727  LTIFIGQYLY  KTYPKLRSYF  VYDDFKKL--  -----D----  -----SNYLK
F0K1W6_LACD2    156  LSTIVGNYLY  QVYPNLRRMF  VYGEFKKFSS  NaeESA----  -----HDVAR
D4FGK2_9LACO    167  LTTICGNLLY  QAYPKLRPFF  VYGQFKKFSS  DP-KKE----  -----NEILK
E1NX12_9LACO    312  LNIVVGNIFD  T---------  ------KFTQ  DP-RNF----  -----IKNTK
E7NSW3_TREPH    222  LNIAVGNVYY  T---------  ------KFTS  NP-RNF----  -----MK1--
H1D477_9FUSO    388  ----------  ----------  ----------  ----------  ----------
C2KFJ4_9LACO    177  LTTICGNLLY  QAYPKLRPFF  VYGQFKKFSS  DP-KKE----  -----NEILK
K1MRU9_9LACO    171  LTTICGNLLY  QAYPKLRPFF  VYGQFKKFSS  DP-KKrk---  ----------
E3ZTQ9_LISSE    532  LNCVVANTLL  KVYPQLEPEF  VYGDYHQF--  -----Dwfka  n--------K
Cas9 Pyogenes   989  LNAVVGTALI  KKYPKLESEF  VYGDYKVY--  -----Dvrkm  iakseQEIGK
                                                          *

D8IJI4_LACSC    761  HMDKFNFIWK  LEDKKAE-D-  ----------  --VYDN-VNN  EFILNVPKMK
F0K1W6_LACD2    197  RVKSMNFLDD  LLRGTHG-D-  ----------  --NIycrSTG  EIVFNRNDII
D4FGK2_9LACO    207  KTKNFDFVAK  LLGSKAP-N-  ----------  --EIRS-QQG  KVLFEKNKIR
E1NX12_9LACO    337  DSRNYNLe--  ----------  ----------  -----K-IYD  YNVERNNYVA
E7NSW3_TREPH    245  ----------  ----KEP-Y-  ----------  --NLRE-LFD  RDVERNNTIA
H1D477_9FUSO    388  ----------  ----------  ----------  ----------  ----------
C2KFJ4_9LACO    217  KTKNFDFVAK  LLGSKAP-N-  ----------  --EIRS-QQG  KVLFEKNKIR
K1MRU9_9LACO    207  ----------  ----------  ----------  ----------  ----------
E3ZTQ9_LISSE    567  ATAKKQFYTN  IMLFFakkD-  ----------  --RIID-ENG  EILWDK-KYL
Cas9 Pyogenes  1032  ATAKYFFYSN  IMNFFkteit  langeirkrp  liETNG-ETG  EIVWDKGRDF
```

* corresponds to the predicted 5'-first and 3'-end positions of the HNH Domain of the *S. pyogenes* Cas9.
Grey highlighted sequence: predicted DNA/RNA binding region (see example 3).

TABLE 4

Secondary structure predictions for the HNH domain and related HNH domain sequence of the *S. pyogenes* Cas9 (SEQ ID NO: 23).

Sequence of Cas9 Pyogenes
PVENTQLQNEKLYLYYLQNGRDMYVDQELDINRLSDYDVDHIVPQSFLKD
DSIDNKVLTRSDKNRGKSDNVPSEEVVKKMKNYWRQLLNAKLITQRKFDN
LTIKAERGGLSELDKAGFIKRQLVETRQITKHVAQILDSRMNTKYDENDK
LIREVKVITLKSKLVSDFRKDFQFYKVREINNYHHAHDAYLNAVVGTALI
KKYPKLESEFVYGDYKVYDVRKMIAKSEQEIGKATAKYFFYSNIMNFFKT
EITLANG Secondary structure Prediction (Psipred)
CCCCCHHHHHHHHHHHHHCCCCCCCCCCCCHCHCCCCCCCSSSCCCCCCC
CCHHHHHHCCHHHHHHHCCCCHHHHHHHHHHHHHHHHHCCCCHHHHHH
HHHHCCCCCCCHCHHHHHHCCHHHHHHHHHHHHHHHHHHHHCCCCCCC
CCCCSSSSSCCHHHHHHHHHCCCCCCCCCCCCHHHHHHHHHHCCHHHHH
HHHHCHHHHHCCHHHHHHHHHHCCCCCCHHHHHHCCCCCCCCHHCCHHHH
HHHHCC H represents helix, S represents sheet and C represents coil.

TABLE 5

Multiple sequence alignment of shorter Cas9 homologues: D4IZM9_BUTFI
(SEQ ID NO: 24), Q9CLT2_PASMU (SEQ ID NO: 25), E0G5X6_ENTFL (SEQ ID NO:
26), E0XXB7_9DELT (SEQ ID NO: 27) with Cas9 Pyogenes (SEQ ID NO: 3).

```
D4IZM9_BUTFI    1  mgi------- ---------- TIGLDLGVAS VGWAVVNDDY EILESCSNIF
Q9CLT2_PASMU    1  mgttnls--- ---------Y ILGLDLGIAS VGWAVVeine nedpigliDV
E0G5X6_ENTFL    1  MK-------- ------KDY VIGLDLGTNS VGWAVMTEDY QLVKKKMPIY
E0XXB7_9DELT    1  msskaidsle qldlfkpQEY TLGLDLGIKS IGWAILSGEr ia------NA
Cas9 Pyogenes   1  MD-------- -------KKY SIGLDIGTNS VGWAVITDEY KVPSKKFKVL D4IZM9_BUTFI   34  ---------- PSADASK--- ---------- ---NSERRGF RQGRRLTRRR
Q9CLT2_PASMU   39  GVRIFERAEV PKTGESL--- ---------- ---ALSRRLA RSTRRLIRRR
E0G5X6_ENTFL   36  ---------- GNTEKKKIKK NFWGVRLFEE GHTAEDRRLK RTARRRISRR
E0XXB7_9DELT   45  GVYLFETAEE LNSTGNK--- ---------- ---LISKAAE RGRKRRIRRM
Cas9 Pyogenes  36  ---------- GNTDRhsIKK NLIGALLFDS GETAEATRLK RTARRRYTRR D4IZM9_BUTFI   58  KNRIHDFQKL WEDKgf---- ---------- ---------- ----------
Q9CLT2_PASMU   73  AHRLLLAKRF LKREgilsti dlekglpnqa ---------- ----------
E0G5X6_ENTFL   76  RNRLRYLQAF FEEAMTDLDE NFFARLQESF LVPEDKKWHR HPIFakleDE
E0XXB7_9DELT   79  LDRkarrgrh iryll----- ---------- --------ER EGLPTDELEE
Cas9 Pyogenes  76  KNRICYLQEI FSNEMAKVDD SFFHRLEESF LVEEDKKHER HPIFGNIVDE D4IZM9_BUTFI   74  VIPSQGTEDV LAIKIKGLS- -EKLSVDEVY WVLLNSLKHR GIsy----LD
Q9CLT2_PASMU  103  ---------- WELRVAGLE- -RRLSAIEWG AVLLHLIKHR GYLSKRKNES
E0G5X6_ENTFL  126  VAYHETYPTI YHLRKKLADS SEQADLRLIY LALAHIVKYR GHFLIEGKLS
E0XXB7_9DELT  106  VVVHQSNRTL WDVRAEAVE- -RKLTKQELA AVLFHLVRHR GYFPNTKKLP
Cas9 Pyogenes 126  VAYHEKYPTI YHLRKKLVDS TDKADLRLIY LALAHMIKFR GHFLIEGDLN D4IZM9_BUTFI  118  DADSGDNSSD YAKSISRNEE ELKEKLpcei qwerlqkyga yrgnisived
Q9CLT2_PASMU  141  QTNNKELGAL LSGVAQNHQL LQsddyrtpa elalkkfake eghi-RNQRG
E0G5X6_ENTFL  176  TENISVKEQF QQFMIIYNQT Fvngesrlvs ap-------- ----------
E0XXB7_9DELT  154  PDDESDSADE EQGKINRATS RLREELkasd cktigqflaq nrdrqRNREG
Cas9 Pyogenes 176  PDNSDVDKLF IQLVQTYNQL FEenpinasg vdakailsar lsksrrlen- D4IZM9_BUTFI  168  gepitlrnvf ttsaykKEVE QFIDTQAKYN AQYSGDFKAD YLEIFNRKRe
Q9CLT2_PASMU  190  AYTHTFNRLD LL----AELN LLFAQQHQFG NPHCKEhiqq ymtellmwqk
E0G5X6_ENTFL  208  -----LPESV LI----EEEL TEKASRTKKS EKVLQQFPQE KANGLFGQFL
E0XXB7_9DELT  204  DYSNLMARKL VF----EEAL QILAFQRKQG HELSKDFEKT YLDVLMGQRs
Cas9 Pyogenes 225  ---------- ---------- ---------- --LIAQLPGE KKNGLFGNLI D4IZM9_BUTFI  218  ---------- ---------- ---------- ---------- ----------
Q9CLT2_PASMU  236  palsgeail- ---------- ---------- ---------- ----------
E0G5X6_ENTFL  249  KLMVGNKADF KKVFGLEEEA KItyasESYE EDLEGILAKV GDEYSDVFLA
E0XXB7_9DELT  250  grspk----- ---------- ---------- ---------- ----------
Cas9 Pyogenes 243  ALSLGLTPNF KSNFDLAEDA KLqlskDTYD DDLDNLLAQI GDQYADLFLA D4IZM9_BUTFI  218  ---------- ---------- ---------- ---------- ----------
Q9CLT2_PASMU  245  ---------- ---------- ---------- ---------- ----------
E0G5X6_ENTFL  299  AKNVYDAVEL STILadsdkk shaklsssmi vRFTEHQEDL KKFKRFIREN
E0XXB7_9DELT  255  ---------- ---------- ---------- ---------- ----------
Cas9 Pyogenes 293  AKNLSDAILL SDILrvntei tkaplsasmi kRYDEHHQDL TLLKALVRQQ D4IZM9_BUTFI  218  ---------- ---------- ---------- ---------- ----------
Q9CLT2_PASMU  245  ---------- ---------- ---------- ---------- ----------
E0G5X6_ENTFL  349  CPDEYDNLFK NEQKDGYAGY IahaGKVSQL KFYQYVKKII QDIAGAEYFL
E0XXB7_9DELT  255  ---------- ---------- ---------- ---------- ----------
Cas9 Pyogenes 343  LPEKYKEIFF DQSKNGYAGY Id--GGASQE EFYKFIKPIL EKMDGTEELL D4IZM9_BUTFI  218  ---------- ---------- ---------- ---------- ----------
Q9CLT2_PASMU  245  ---------- ---------- ---------- ---------- ----------
E0G5X6_ENTFL  399  EKIaQENFLR KQRTFDNGVI PHQIHLAELQ AIIHRQaaYY PFLKENQEKI
E0XXB7_9DELT  255  ---------- ---------- ---------- ---------- ----------
Cas9 Pyogenes 391  VKLnREDLLR KQRTFDNGSI PHQIHLGELH AILRRQedFY PFLKDNREKI D4IZM9_BUTFI  218  ---------Y YEGPgnelsr tdygkyttei nadgeyitvd nif-------
Q9CLT2_PASMU  245  ---------- ---------- ---------- ---------- ----------
E0G5X6_ENTFL  449  EQLVTFRIPY YVGPLSKGDa STFAWLKRQS EEPIRPWNLQ ETVDLDQSAT
E0XXB7_9DELT  255  ---------- ---------- ---------- ---------- ----------
Cas9 Pyogenes 441  EKILTFRIPY YVGPLARGN- SRFAWMTRKS EETITPWNFE EVVDKGASAW D4IZM9_BUTFI  252  ---DKLVGKC SVNPDERRAA GASYTAQEFN VLNDLNNLTI SSESsfi---
Q9CLT2_PASMU  245  ----KMLGKC THEKNEFKAA KHTYSAERFV WLTKLNNLRI LEDGAER-Al
E0G5X6_ENTFL  499  AFIERMTNFD TYLPSEKVLP KHSLLYEKFM VFNELTKISY TDDRGIK-AN
E0XXB7_9DELT  255  ------LGNC SLIPSELRAP SSAPSTEWFK FLQNLGNLQI SNAYREewsi
Cas9 Pyogenes 490  SFIERMTNFD knLPNEKVLP KHSLLYEYFT VYNELTKVKY VTEGMRKpAF D4IZM9_BUTFI  296  ---------- ---EDGKLTE DAKRKIIeTI K----NAKTV NVKKIICdvi
Q9CLT2_PASMU  290  neeeRQLLIN HPYEKSKLTY AQVRKLLGLS EQAIFKHLRY SK--------
E0G5X6_ENTFL  548  FSGKEKEKIF DYLFKTRRKV --------KK K----DIIQF YR--------
E0XXB7_9DELT  299  daprRAQIID ACSQRSTSSY WQIRRDFQIP DEYRFNLVNY ER--------
Cas9 Pyogenes 540  LSGEQKKAIV DLLFKTNRKV --------TV K----QLKED YFKKIECfds
```

TABLE 5-continued

Multiple sequence alignment of shorter Cas9 homologues: D4IZM9_BUTFI (SEQ ID NO: 24), Q9CLT2_PASMU (SEQ ID NO: 25), E0G5X6_ENTFL (SEQ ID NO: 26), E0XXB7_9DELT (SEQ ID NO: 27) with Cas9 Pyogenes (SEQ ID NO: 3).

```
D4IZM9_BUTFI   329  gdkkcqisga riDKNEKEIF HSFE------ -----AYNKM RRALEEIGF-
Q9CLT2_PASMU   332  ---------- --ENAESATF MELF------ -----AWHAI RKALENQGLK
E0G5X6_ENTFL   578  ---------- --NEYNTEIV TLSGLEEDQF NASFSTYQDL LKc----GLT
E0XXB7_9DELT   341  ---------- --RDPDVDLQ EYLQQQERKT LANFRNWKQL EKiigtghpi
Cas9 Pyogenes  578  veisgv---- ---------- ------EDRF NASLGTYHDL LKIIKDKDF- D4IZM9_BUTFI   367  ---DISSLSR ENLDLIGDIL TLNTDRESIL NAFNRKGIEL ADEAkdilvk
Q9CLT2_PASMU   359  DTWQDLAKKP DLLDEIGTAF SLYKTDEDIQ QYLTNKVPNS VINAL--LVS
E0G5X6_ENTFL   612  RAELDHPDNA EKLEDIIKIL TIFEDRQRIR TQLSTFKGQF SAEVLKKLER
E0XXB7_9DELT   379  ---------- QTLDEAARLI TLIKDDEKLS DQLADLLPEA SDKAITQLCE
Cas9 Pyogenes  607  ---LDNEENE DILEDIVLTL TLFEDREMIE ERLKTYAHLF DDKVMKQLKR D4IZM9_BUTFI   414  vrktngsl-- ---------- FNKWQSFGLS IMNELIPELY AQPknqmell
Q9CLT2_PASMU   407  LNFDKFIELS LKSLRKILPL MEQGKRYDQA CREiyghhyg eanqktsqll
E0G5X6_ENTFL   662  KHYTGWGRL- ---------- ---------- ---------- ----------
E0XXB7_9DELT   419  LDFTTAAKIS LEAMYRILPH MNQGMGFFDA CQQESLPEID VPPagdrvpp
Cas9 Pyogenes  654  RRYTGWGRL- ---------- ---------- ---------- ----------

D4IZM9_BUTFI   452  tamgvfksrg drfleckeip gdlivDDIYN PVVSKTVRIT VRILNALIKK
Q9CLT2_PASMU   457  paipaq---- ---------- ------EIRN PVVLRTLSQA RKVINAIIRQ
E0G5X6_ENTFL   671  ---------- ---------- ---------- --------S  KKLINGIYDK
E0XXB7_9DELT   469  f--------- ---------- -----DEMYN PVVNRVLSQS RKLINAVIDE
Cas9 Pyogenes  663  ---------- ---------- ---------- --------S  RKLINGIRDK D4IZM9_BUTFI   502  YG-------- ---------- ---------- ---------- ----------
Q9CLT2_PASMU   487  YG-------- ---------- ---------- ---------- ----------
E0G5X6_ENTFL   682  ESGKTILGYL IKDdgvskhy NRNFMQLIND SQLSFKNAIQ KAQSSeheET
E0XXB7_9DELT   495  YG-------- ---------- ---------- ---------- ----------
Cas9 Pyogenes  674  QSGKTILDFL KSDgfa---- NRNFMQLIHD DSLTFKEDIQ KAQVSgqgDS D4IZM9_BUTFI   504  ---------- ---------- ---------- ----Y-PDRV VIEMPRDK-N
Q9CLT2_PASMU   489  ---------- ---------- ---------- ----S-PARV HIETGRELGK
E0G5X6_ENTFL   732  LSETVNELAG SPAIKKGIYQ SLKIVDELVA IMGyA-PKRI VVEMAREN-Q
E0XXB7_9DELT   497  ---------- ---------- ---------- ----M-PAKI RVELARDLGK
Cas9 Pyogenes  720  LHEHIANLAG SPAIKKGILQ TVKVVDELVK VMGrhkPENI VIEMAREN-Q D4IZM9_BUTFI   518  SDEEQQRLKK EQRDNENEIK DIKARVKTEY GREITEEDFR QHSKLSLKLK
Q9CLT2_PASMU   504  SFKERREIQK QQEDNRTKRE SAVQKPKELF SDFSSEPK-- --SKDILKFR
E0G5X6_ENTFL   780  TTSTGKRRSI QRLKIVEKAM AEIGSNL--- ---LKEQPTT NEQLRDTRLF
E0XXB7_9DELT   512  grELRERIKL DQLDKSKQnd ---QRAEDFR AEFQQAPR-- --GDQSLRYR
Cas9 Pyogenes  769  TTQKGQKNSR ERMKRIEEGI KELGSQI--- ---LKEHPVE NTQLQNEKLY D4IZM9_BUTFI   568  LWNEQQGICP YSGKSIKIDD LL---Dnpnl FEVDHIIPLS ISFDDSRNNK
Q9CLT2_PASMU   550  LYEQQHGKCL YSGKEINIHR LNekgY---- VEIDHALPFS RTWDDSFNNK
E0G5X6_ENTFL   824  LYYMQNGKDM YTGDELSLHR LS---H---- YDIDHIIPQS FMKDDSLDNL
E0XXB7_9DELT   555  LWKEQNCTCP YSGRMIPVNS VLse-D---- TQIDHILPIS QSFDNSLSNK
Cas9 Pyogenes  813  LYLLQNGRDM YVDQELDINR LS---D---- YDVDHIVPQS FLKDDSIDNK D4IZM9_BUTFI   615  VLVYSSENQD KGNRTPLAYL asvnrqwdih sfmdyvLKTY AGAQKRKKRD
Q9CLT2_PASMU   596  VLVLASENQN KGNQTPYEWL qgkinserwk nfvalvlgsq csaa------
E0G5X6_ENTFL   867  VLVGSTENRG KSDDVPSKEV VKDMKAYWek lyaAGLI--- ---SQRKFQR
E0XXB7_9DELT   600  VLCFTEENAQ KSNRTPFEYL daadfqr--- ------LEAI SGNWPEAKRN
Cas9 Pyogenes  856  VLTRSDKNRG KSDNVPSEEV VKKMKNYWrq llnAKLI--- ---TQRKFDN
                                                                    *

D4IZM9_BUTFI   665  NLLNEQDITK VEVLQGFVNR NINDTRYASK VVLNSLQEYF SSK-------
Q9CLT2_PASMU   640  --KKQRLLTQ VIDDNKFIDR NLNDTRYIAR FLSNYIQENL llvgknkk--
E0G5X6_ENTFL   911  LTKGEQGGLT LEDKAHFIQR QLVETR---- ---------- ----------
E0XXB7_9DELT   641  KLLHKSfg-- -KVAEEWKSR ALNDTRYLTS ALADHLRHHL PDS-------
Cas9 Pyogenes  900  LTKAERGGLS ELDKAGFIKR QLVETRQITK HVAQILDSRM NTKydendkl
                       *

D4IZM9_BUTFI   708  ----ECSTkv kvirgsfthq mrvnlk---- ---------- ----------
Q9CLT2_PASMU   686  ----NVFTPN GQITALLRSR WGLIKARENN NRHHALDAIV VACATPSMQQ
E0G5X6_ENTFL   937  ---------- ---------- ---------- ---------- ----------
E0XXB7_9DELT   681  ----KIQTVN GRITGYLRKQ WGLEKDRDKH t-HHAVDAIV VACTTPAIVQ
Cas9 Pyogenes  950  irevKVITLK SKLVSDFRKD FQFYKVREIN NYHHAHDAYL NAVVGTALIK
```

* corresponds to the predicted 3'-end positions of the shorter Cas9 versions.

Grey highlighted sequence: predicted DNA/RNA biding region (see example 3).

TABLE 6

Secondary structure predictions of shorter Cas9 versions and related shorter *S. pyogenes* Cas9 sequence. H represents helix, S represents sheet and C represents coil.

Sequence of Cas9 Pyogenes
MDKKYSIGLDIGTNSVGWAVITDEEKVPSKKEKVLGNTDRHSIKKNLIG
ALLFDSGETAEATRLKRTARRRYTRRKNRICYLQEIFSNEMAKVDDSFF
HRLEESFLVEEDKKHERHPIEGNIVDEVAYHEKYPTIYHLRKKLVDSTD
KADLRLIYLALAHMIKERGHFLIEGDLNPDNSDVDKLFIQLVQTYNQLF
EENPINASGVDAKAILSARLSKSRRLENLIAQLPGEKKNGLFGNLIALS
LGLIPNEKSNEDLAEDAKLQLSKDTYDDDLDNLLAQIGDQYADLFLAAK
NLSDAILLSDILRVNTEITKAPLSASMIKRYDEHHQDLTLLKALVRQQL
PEKYKEIFFDQSKNGYAGYIDGGASQEEFEKEIKPILEKMDGTEELLVK
LNREDLLRKQRTFDNGSIPHQIHLGELHAILRRQEDFYPFLKDNREKIE
KILTFRIPYYVGPLARGNSRFAWMTRKSEETITPWNFEEVVDKGASAQS
FIERMTNEDKNLPNEKVLPKHSLLYEYFTVYNELTKVKYVTEGMRKPAF
LSGEQKKAIVDLLFKTNRKVIVKQLKEDYFKKIECFDSVEISGVEDRFN
ASLGTYHDLLKIIKDKDFLDNEENEDILEDIVLTLTLFEDREMIEERLK
TYAHLFDDKVMKQLKRRRYTGWGRLSRKLINGIRDKQSGKTILDFLKSD
GFANRNFMQLIHDDSLTFKEDIQKAQVSGQGDSLHEHIANLAGSPAIKK
GILQTVKVVDELVKVMGRHKPENIVIEMARENQTTQKGQKNSRERMKRI
EEGIKELGSQILKEHPVENTQLQNEKLYLYYLQNGRDMYVDQELDINRL
SDYDVDHIVPQSFLKDDSIDNKVLTRSDKNRGKSDNVPSEEVVKKMKNY
WRQLLNAKLITQRKFDNLTKAERGGLSELDKAGFIKRQLVETRQITKHV
AQILDSRMNTKYDENDKLIREVKVITLKSKLVSDFRKDFQFYKVREINK
Y

TABLE 6-continued

Secondary structure predictions of shorter Cas9 versions and related shorter *S. pyogenes* Cas9 sequence. H represents helix, S represents sheet and C represents coil.

Secondary structure Prediction (Psipred)
CCCCSSSSSSSCCCCSSSSSSSCCCCCCCCCCCCCCCCCCCCCCCCSSS
SSSCCCCCHHHHHHHHHHHHHHHHHHHHHHHHHHHCCCCCHHH
HHCCCCCCCCCCCCCCCCCCHHHHHHHHCCCHHHHHHHHHCCCC
CCCHHHHHHHHHHHHCCCCCCCCCCCCCCCHHHHHHHHHHHHHC
CCCCCCHHHHHHHHHHCCCCHHHHHHHHCCCCCCCHHHHHHHHHH
HCCCCCHHCCCCCCCCCCCSCCCCHHHHHHHHHHCHHHHHHHHHHH
HHHHHHHHHCCCCCCCCCCCCCHHHHHHHHHHHHHHHHHHHHHCC
HHHCCCCCCCCCCCCSSCHHHHHHHHHHHHHHHCHHHCCCHHHHH
HHHSCCCCCCCCCCCCCCCCCSSSCCCCCCCCCCCCCCCHHCCCHHHH
HHHHCCCCCCCCCCCCCCCCCHHHHHHHHHHHHHCSSSCCCCCCCCCC
CCHHHHHHHHHHCCCCCHHHHHHHHHHCCCCCCCSCCCCCCCCH
CCCHHHHHHHHCCCCCCCCCCCHHHHHHHHHHHCCCHHHHHHH
HHCCCCCHHHHHHCCCCHHHHHHHHHHCCHHHHCCCCHHHHHHHH
HHCCHHHHHHHHCCCCCHHHHHHHHHHHCCCCHHHHHHHCCCHHHHH
HHHHHHHHHHHHCCCCCCSSSSSSCCCCCCHHHHHHHHHHHH
HHHHHHHHHCCCCCHHHHHHHHHHHHHCCCCCCCCCCCCHCHC
CCCCCCSSSCCCCCCCCHHHHHHCCHHHHHHCCCCHHHHHHHHHHH
HHHHHCCCCCHHHHHHHCCCCCCCCCHHHHHHHHHHHHHHH
HHHHHHHHHHCCCCCCCCCSSSSCCHHHHHHHHHHCCCCCCCCCCC
CHHHHHHHHHHCCHHHHHHHHCCHHHCCCHHHHHHHHHCCCCCHH
HHHHCCCCCCCHHCCHHHHHHHHCCCCCCCCCCCCCCCCCSSSSC

TABLE 7

List of DNA/RNA binding regions of *S. pyogenes* Cas9.

| No | SEQ ID | Cas 9 domain | amino acid positions | sequence of amino acids | secondary structure prediction | degree of solvent exposition |
| --- | --- | --- | --- | --- | --- | --- |
| 1 | 34 | RuvC domain | S15-V20 | SVGWAV | CEEEEE | C-terminal exposed |
| 2 | 35 | RuvC domain | S29-K33 | SKKFK | CCCCC | not exposed |
| 3 | 36 | RuvC domain | T63-R78 | TRLKRTARRRYTRRKNR | HHHHHHHHHHHHHHHH | not exposed |
| 4 | 37 | Interdomain | S213-R221 | SARLSKSRR | HHCCCHHH | not exposed |
| 5 | 38 | Interdomain | K314-Y325 | KAPLSASMIKRY | CCCCCHHHHHH | not exposed |
| 6 | 39 | Interdomain | F446-R467 | FRIPYYVGPLARGNSRFAWMTR | HCCCCCCCCCCCCCCHHHHHHH | not exposed |
| 7 | 40 | Interdomain | T525-R535 | TKVKYVTEGMR | HCEEEECCCCC | highly exposed |
| 8 | 41 | Interdomain | R557-K565 | RKVTVKQLK | CCCCHHHH | highly exposed |
| 9 | 42 | Interdomain | K652-K665 | KRRRYTGWGRLSRK | HCCCCCCHHHHHHH | c-terminal highly exposed |
| 10 | 43 | Interdomain | Q768-R780 | QTTQKGQKNSRER | CCCHHHHHHHHHH | highly exposed |
| 11 | 44 | HNH domain | R859-S867 | RSDKNRGKS | CCCCCCCCC | average exposed |
| 12 | 45 | HNH domain | K878-A889 | KKMKNYWRQLLNA | HHHHHHHHHHHH | not exposed |
| 13 | 46 | HNH domain | N979-Y988 | NNYHHAHDAY | CCCHHHHHH | not exposed |
| 14 | 47 | HNH domain | E1150-S1159 | EGKSKKLKS | EECCCCCCEEH | not exposed |
| 15 | 48 | HNH domain | R1333-E1341 | RKRYTSTKE | CCCCCCCCC | not exposed |

TABLE 8

Multiple sequence alignment between Cas9 of *S. pyogenes* (SEQ ID NO: 61) and *S. thermophilus* (SEQ ID NO: 64) and the sequence of two pdb structures of RuvC domain of *E. coli* and *T. thermophilus* (SEQ ID NO: 62 and SEQ ID NO: 63).

```
              ....|....| ....|....| ....|....| ....|....| ....|....| ....|....|
                   5          15         25         35         45         55
4EP4:A|PDB    ---------- ---------- ----MVVAGI DPGITHLGLG VVAVEGKG-A LKARLLHG--
Cas9_sp       ---------- ---------- -MDKKYSIGL DIGTNSVGWA VITDEYKVPS KKFKVLGNTD
Cas9_S.The    MLFNKCIIIS INLDFSNKEK CMTKPYSIGL DIGTNSVGWA VITDNYKVPS KKMKVLGNTS
RuvC_E.Col    ---------- ---------- ---MAIILGI DPGSRVTGYG VIRQVGR--- -QLSYLGS--

....|....| ....|....| ....|....| ....|....| ....|....| ....|....|
                  65         75         85         95        105        115
4EP4:A|PDB    ---------- --------EV VKTSPQEPAK ERVGRIHARV LEVLHRFRPE AVAVEEQFFY
Cas9_sp       RHSIKKNLIG ALLFDSGETA EATRLKRTAR RRYTRRKNRI CYLQEIFSNE MAKVDDSFFH
Cas9_S.The    KKYIKKNLLG VLLFDSGITA EGRRLKRTAR RRYTRRRNRI LYLQEIFSTE MATLDDAFFQ
RuvC_E.Col    ---------- --------GC IRTKVDD-LP SRLKLIYAGV TEIITQFQPD YFAIEQVFMA

....|....| ....|....| ....|....| ....|....| ....|....| ....|....|
                 125        135        145        155        165        175
4EP4:A|PDB    RQNELAYKVG WALG------ --AVLVAAFE AGVPVYAYGP MQVKQA---- ----------
Cas9_sp       RLEESFLVEE DKKHERHPIF GNIVDEVAYH EKYPTIYHLR KKLVDSTDKA DLRLIYLALA
Cas9_S.The    RLDDSFLVPD DKRDSKYPIF GNLVEEKVYH DEFPTIYHLR KYLADSTKKA DLRLVYLALA
RuvC_E.Col    KNADSALKLG QARG------ --VAIVAAVN QELPVFEYAA RQVKQT---- ----------

....|....| ....|....| ....|....| ....|....| ....|....| ....|....|
                 185        195        205        215        225        235
4EP4:A|PDB    ---------- LAGHGHAAKE EVALMVRGIL G-----LKEA PRPSHLADAL AIALTHAFYA
Cas9_sp       HMIKFRGHFL IEGDLNPDNS DVDKLFIQLV QTYNQLFEEN PINASGVDAK AILSARLSKS
Cas9_S.The    HMIKYRGHFL IEGEFNSKNN DIQKNFQDFL DTYNAIFESD LSLENSKQLE EIVKDKISKL
RuvC_E.Col    ---------- VVGIGSAEKS QVQHMVRTLL K-----LPAN P-QADAADAL AIAITHCHVS

....|....| ....|....| ....|....| ....|....| ....|....| ....|....|
                 245        255        265        275        285        295
4EP4:A|PDB    R--MGTAKPL ---------- ---------- ---------- ---------- ----------
Cas9_sp       RRLENLIAQL PGEKKNGLFG NLIALSLGLT PNFKSNFDLA EDAKLQLSKD TYDDDLDNLL
Cas9_S.The    EKKDRILKLF PGEKNSGIFS EFLKLIVGNQ ADFRKCFNLD EKASLHFSKE SYDEDLETLL
RuvC_E.Col    QNAMQMSESR LNLARGRLR- ---------- ---------- ---------- ----------
```

TABLE 9

Multiple sequence alignment of the eight select sequences with Cas9 wild type of *S. Pyogenes* and Cas9 of *S. Thermophilus* and 4EP4 pdbcode. The position of the G247 is marked by a black arrow.

```
            ....|....| ....|....| ....|....| ....|....| ....|....| ....|....| ....|....|
                 5          15         25         35         45         55         65
Cas9wt      ---------- ---------- -MDKKYSIGL DIGTNSVGWA VITDEYKVPS KKFKVLGNTD RHSIKKNLIG
D8IJI3      ---------- ---------- --MERYHIGL DIGTSSIGWA VIGDDFKIK- ---------- -RKKGKNLIG
F0K1W4      ---------- ---------M AKPKDYTIGL DIGTNSGWV VTDDQNNIL- ---------- -RIKGKKAIG
C5F1Z4      ---------- ---------- ----MKILGF DIGIASIGWA FVENGELKD- ---------- -CGVRIFTKA
F3ZS86      ---------- ---------- ---MKKILGL DIGTNSVGWA VVNTNQEGEP SQIEKLGSRI IPMSQDILDK
H1D479      ---------- ---------M KKFENYYLGL DIGTSSIGWA VTNSQYDIL- ---------- -KFNGKYMWG
K1M766      ---------- --------MT KLNNEYMVGL DIGTNSCGWV ATDFDNNIL- ---------- -KMHGKRALG
Q7VG48      ---------- ---------- ----MRILGF DIGITSIGWA YVESNELKD- ---------- -CGVRIFTKA
E9S0G6      ---------- --------MK KEIKDYFLGL DVGTGSVGWA VTDTDYKLL- ---------- -KANRKDLWG
4EP4        ---------- ---------- ----MVVAGI DPGITHLGLG VVAVE----- ---------- ----GKGALK
G3ECR1      MLFNKCIIIS INLDFSNKEK CMTKPYSIGL DIGTNSVGWA VITDNYKVPS KKMKVLGNTS KKYIKKNLLG

....|....| ....|....| ....|....| ....|....| ....|....| ....|....| ....|....|
                75         85         95        105        115        125        135
Cas9wt      ALLFDSGETA EATRLKRTAR RRYTR---RK NRICYLQEIF SNEMAKVDDS FFHR-LEES- FLVEEDKKHE
D8IJI3      VRLFKEGDTA AERRSFRTQR RRLNR---RK WRLKLLEEIF DPYMAEVDEY FFAR-LKESS LSPKDSNKKY
F0K1W4      ARLFTEGKVA AERRSFRTTR RRLSR---RR WRIKMLEELF DEEIAKVDPS FFAR-LHESW ISPKDK-RKR
C5F1Z4      ENPKTGDSLA MPRREARSVR RRLAR---RK GRLETLKRLL AKEWDLCYED YIAADGELPK AFMG-KNLTN
F3ZS86      FGQGQTVSST ASRTDYRGIR RLRERSLLRR ERLHRVLHIL DFLPKHYADS IGWDPRNSKT YGKFLPGTEV
H1D479      TRLFPEANTA QERRIHSSRR RRLKR---RK ERIQILQMLF DKEIAKIDSG FFQR-LKDSK YYKEDKTEKQ
K1M766      SHLFDEGVSA ADRRAFRTTR RRIKR---RK HELKLLEEIF DEEMAKVDPN FFAR-LKESG LSPLDT-RKN
Q7VG48      ENPKNGDSLA APRREARGAR RRLAR---RK ARLNAIKRLL CKEFELNLND YLANDGELPK AYQTSKDTKS
E9S0G6      MRCFETAETA EVRRLHRGAR RRIER---RK KRIKLLQELF SQEIAKTDEG FFQR-MKESP FYAEDKTILQ
4EP4        ARLLHGEVVK TSPQ--EPAK ERVGR---IH ARVLEVLHRF RPEAVAVEEQ FFYR------ --QNELAYKV
G3ECR1      VLLFDSGITA EGRRLKRTAR RRYTR---RR NRILYLQEIF STEMATLDDA FFQR-LDDS- FLVPDDKRDS
```

TABLE 9-continued

Multiple sequence alignment of the eight select sequences with Cas9 wild type of S. Pyogenes and Cas9 of S. Thermophilus and 4EP4 pdbcode. The position of the G247 is marked by a black arrow.

```
            ....|....| ....|....| ....|....| ....|....| ....|....| ....|....| ....|....|
              145        155        165        175        185        195        205
Cas9wt   RHPIFGN-IV DEVAYHEKYP TIYHLRKKLV DSTDKADLRL IYLALAHMIK FRGHFLIEGD LNPDNSDVDK
D8IJI3   LGSLLFP-DI SDSNFYDKYP TIYHLRRDLM EKDKKFDLRE IYLALHHIVK YRGNFLEKVP AKNYKNSGAS
F0K1W4   YSAIVFPSPE EDKKFHESYP TIYHLRDKLM KDDQKHDIRE IYIAVHQMIK ARGNFLHDES VETYRSGMSS
C5F1Z4   PYVLRYEALQ RLLSKEELVR VVLHIAKHRG YGNKNAKITK SEESKREQGK ILSALATNAS VIARYRTVGE
F3ZS86   KLAWVPTADG HQFLFYSTYL EMLEDLKQTQ AQLFETSQTP VPLDWTIYYL RKKALTQPIT KHELAWLLLH
H1D479   TNSIFHDKDY SDKEYHQDFP TIYHLRKFLL EGNKPKDIRF VYLALHHILT HRGHFLFPDM EVSNVTEFSN
K1M766   VSSIVFPTKK MDKQFYKKFP TIYHLRNALM KQDKKFDLRA IYIAIHHIVK YRGNFLSNSS ISNFSASKIE
Q7VG48   PYEL-YTAFH ---------- ---------- ---------- ---------W IIFAFCSIAS SLS-------
E9S0G6   ENALFNDRDF TDKTYHKAYP TINHLIKAWI ENKVKPDPRL LYLACHNIIK KRGHFLF-EG DFDSENQFDT
4EP4     GWALGAVLVA AFEAGVPVYA YGPMQVKQAL AGHGHAAKEE VALMVRGILG LKEAPRPSHL ADALAIALTH
G3ECR1   KYPIFGN-LV EEKVYHDEFP TIYHLRKYLA DSTKKADLRL VYLALAHMIK YRGHFLIEGE FNSKNNDIQK
            ....|....| ....|....| ....|....| ....|....| ....|....| ....|....| ....|....|
              215        225        235        245        255        265        275
Cas9wt   LFI------- --QLVQTYNQ LFEENP---- ----INASGV DAKAILSARL SKSRRLENLI AQLP------
D8IJI3   IG-------- --FLLEEVNR FI-------- ---------- ---------- ---------- ----------
F0K1W4   LGGRSERNIL SVQTLEELND LFAENEGTEE VELNVASAEQ INDILTGGHL N-ADSQKEIS NLLLPSSFPS
C5F1Z4   YFYK------ --EFCEVIKN PQGLNT---- ---NENCTQP KVRVLKPIRN KGGEYTN--- ----------
F3ZS86   FNTKR----- --GYYQRRGE LEDTPT---- ----DKLVEY HALKVVDVEV DPEDQSK--- ----------
H1D479   IFS------- --ELKQYLYD EMDLDF---- ----EWKTEN ---------- ---------- ----------
K1M766   ID-------- --RFVNELND LYSIFLPESG VIFDAGNASK VEDIIRNEQM FKLDKIKEIA DVLP------
Q7VG48   ---------- ---------N RQ-------- ---------- ----MLPI-- ---------- ----------
E9S0G6   SIQ------- --AFFEYLRE DMEVDI---- ----DADSQK IKEILKDSSL KNSEKQSRLN KILG------
4EP4     AFY------- -----ARMGT AKPL------ ---------- ---------- ---------- ----------
G3ECR1   NFQ------- --DFLDTYNA IFESDL---- ----SLENSK QLEEIVKDKI SKLEKKDRIL KLFP------
            ....|....| ....|....| ....|..▼.| ....|....| ....|....| ....|....| ....|....|
              285        295        305        315        325        335        345
Cas9wt   ---------- GEKKNGLFGN LIALSLGLTP NFKSNFD--- --LAEDAKLQ LSK--DTYDD DLDNLLAQIG
D8IJI3   ---------- ---------- ---------- ---------- ---------- ---------- ----------
F0K1W4   FDDKAKEKQV KKLINNVATN ISKAWLGYKA DFSTILNLAK VDKDQKKIFA FALQGGDEED KVQELESLLE
C5F1Z4   ---------- -CILQEDLQR ELRCIFEHQK GFGFSITQEF QDKILKIAFY QRSLKDFSHL VGKCTFYPDE
F3ZS86   ---------- ---KPWYFVH LENGWIYKRQ SSEPLDNWKG LVKEFIVTTH LDKEGKPKLD KEGEVRRSFS
H1D479   ---------- ---------- ---------- ---------- ---------- ---------- ----------
K1M766   ---DTENKSG LKLSKKISKE ISKAILGYKA KFEIIL-QVN VDKTDSSIWN FKLNDENADV NLSEITSDLT
Q7VG48   ---------- ---------- ---------- ---------- ---------- ---------- ----------
E9S0G6   ---------- LKSSDKQKKA ITNLISGNKI NFADLYDNPD LKDAEKNSIS FSK--DDFDA LSDDLASILG
4EP4     ---------- ---------- ---------- ---------- ---------- ---------- ----------
G3ECR1   ---------- GEKNSGIFSE FLKLIVGNQA DFRKCFN--- --LDEKASLH FSK--ESYDE DLETLLGYIG
```

TABLE 10

Secondary structure elements prediction for the Cas9 wild type of S. Pyogenes sequence using PSIPRED. The sequence has been divided into the two split domains: N-terminal and C-terminal domain. In bold is marked the Leucine 248 which has been mutated to Valine in the sequence of the C-terminal domain.

Sequence of Cas9 Pyogenes

N-terminal domain
MDKKYSIGLDIGTNSVGWAVITDEYKVPSKKFKVLGNTDRHSIKKNLIG
ALLFDSGETAEATRLKRTARRRYTRRKNRICYLQEIFSNEMAKVDDSFF
HRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLF
EENPINASGVDAKAILSARLSKSRRLENLIAQLPGEKKNGLFGNLIALS
LG C-terminal domain
LTPNFKSNFDLAEDAKLQLSKDTYDDDLDNLLAQIGDQYADLFLAAKNL
SDAILLSDILRVNTEITKAPLSASMIKRYDEHHQDLTLLKALVRQQLPE
KYKEIFFDQSKNGYAGYIDGGASQEEFYKFIKPILEKMDGTEELLVKLN
REDLLRKQRTFDNGSIPHQIHLGELHAILRRQEDFYPFLKDNREKIEKI
LTFRIPYYVGPLARGNSRFAWMTRKSEETITPWNFEEVVDKGASAQSFI
ERMTNFDKNLPNEKVLPKHSLLYEYFTVYNELTKVKYVTEGMRKPAFLS
GEQKKAIVDLLFKTNRKVTVKQLKEDYFKKIECFDSVEISGVEDRFNAS
LGTYHDLLKIIKDKDFLDNEENEDILEDIVLTLTLFEDREMIEERLKTY
AHLFDDKVMKQLKRRRYTGWGRLSRKLINGIRDKQSGKTILDFLKSDGF
ANRNFMQLIHDDSLTFKEDIQKAQVSGQGDSLHEHIANLAGSPAIKKGI
LQTVKVVDELVKVMGRHKPENIVIEMARENQTTQKGQKNSRERMKRIEE
GIKELGSQILKEHPVENTQLQNEKLYLYYLQNGRDMYVDQELDINRLSD
YDVDHIVPQSFLKDDSIDNKVLTRSDKNRGKSDNVPSEEVVKKMKNYWR
QLLNAKLITQRKFDNLTKAERGGLSELDKAGFIKRQLVETRQITKHVAQ
ILDSRMNTKYDENDKLIREVKVITLKSKLVSDFRKDFQFYKVREINNY Secondary structure Prediction (Psipred)

N-terminal domain
CCCCSSSSSSCCCCSSSSSSCCCCCCCCCCCCCCCCCCCCCCCCCSSS
SSSCCCCCCHHHHHHHHHHHHHHHHHHHHHHHHHHHHHHHCCCCCHHH
HHHCCCCCCCCCCCCCCCCCCCCHHHCHHHHHHHHHHHHHHHCCCC
CCCHHHHHHHHHHHHHHCCCCCCCCCCCCCCCHHHHHHHHHHHHHHC
CCCCCCHHHHHHHHHHCCCCHHHHHHCCCCCCCHHHHHHHHHHHH
HC C-terminal domain
CCCCHHCCCCCCCCCCCSCCCCCHHHHHHHHHCHHHHHHHHHHHHH
HHHHHHHCCCCCCCCCCCCHHHHHHHHHHHHHHHHHHHHHHHHCCHH
HHHHHHHHCCCCCCCCCCCCHHHHHHHHHHHHHHHHHCCCCHHHHHH
HCCCCCCCCCCCCSCHHHHHHHHHHHHHHHHHCCCHHHHHH
HHSCCCCCCCCCCCCCCCCCSSSCCCCCCCCCCCCCHHCCCHHHHHH
HHCCCCCCCCCCCCCCCHHHHHHHHHHHHHHCSSSCCCCCCCCCCCC
HHHHHHHHHHHHCCCCHHHHHHHHHHHCCCCCCCSCCCCCCCCHCC
CHHHHHHHHHCCCCCCCCCCCHHHHHHHHHHHCCCHHHHHHHHHH TABLE 10-continued Secondary structure elements prediction for the Cas9 wild type of S. Pyogenes sequence using PSIPRED. The sequence has been divided into the two split domains: N-terminal and C-terminal domain. In bold is marked the Leucine 248 which has been mutated to Valine in the sequence of the C-terminal domain.

CCCCHHHHHHHCCCCCHHHHHHHHHHCCHHHCCCHHHHHHHHH
CCHHHHHHHCCCCCHHHHHHCCCCCCCCHHHHHHCCCCHHHHHH
HHHHHHHHHHHHCCCCCCSSSSSSCCCCCCHHHHHHHHHHHHHH
HHHHHHHHHHCCCCCHHHHHHHHHHHCCCCCCCCCCCHCHCCC
CCCCSSSCCCCCCCCHHHHHHCCHHHHHHCCCHHHHHHHHHHHH
HHHHCCCCHHHHHHHHCCCCCCHCHHHHHHCCHHHHHHHHHHH
HHHHHHHHCCCCCCCCCCSSSSSCHHHHHHHHCCCCCCCCCCCH
HHHHHHHHHCCHHHHHHHHHCHHHHHCCCHHHHHHHHCCCCCHHHH
HHCCCCCCCCHHCCHHHHHHHHCCCCCCCCCCCCCCCCSSSSC

REFERENCES

Buchan, D. W., S. M. Ward, et al. (2010). "Protein annotation and modelling servers at University College London." *Nucleic Acids Res* 38(Web Server issue): W563-8.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Dalgaard, J. Z., A. J. Klar, et al. (1997). "Statistical modeling and analysis of the LAGLIDADG family of site-specific endonucleases and identification of an intein that encodes a site-specific endonuclease of the HNH family." *Nucleic Acids Res* 25(22): 4626-38.

de Castro, E., C. J. Sigrist, et al. (2006). "ScanProsite: detection of PROSITE signature matches and ProRule-associated functional and structural residues in proteins." *Nucleic Acids Res* 34(Web Server issue): W362-5.

Deltcheva, E., K. Chylinski, et al. (2011). "CRISPR RNA maturation by trans-encoded small RNA and host factor RNase III." *Nature* 471(7340): 602-7.

Deveau, H., R. Barrangou, et al. (2008). "Phage response to CRISPR-encoded resistance in Streptococcus thermophilus." *J Bacteriol* 190(4): 1390-400.

Eickholt, J., X. Deng, et al. (2011). "DoBo: Protein domain boundary prediction by integrating evolutionary signals and machine learning." *BMC Bioinformatics* 12: 43.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Gorbalenya, A. E. (1994). "Self-splicing group I and group II introns encode homologous (putative) DNA endonucleases of a new family." *Protein Sci* 3(7): 1117-20.

Haft, D. H., J. Selengut, et al. (2005). "A guild of 45 CRISPR-associated (Cas) protein families and multiple CRISPR/Cas subtypes exist in prokaryotic genomes." *PLoS Comput Biol* 1(6): e60.

Horvath, P. and R. Barrangou (2010). "CRISPR/Cas, the immune system of bacteria and archaea." *Science* 327 (5962): 167-70.

Jinek, M., K. Chylinski, et al. (2012). "A programmable dual-RNA-guided DNA endonuclease in adaptive bacterial immunity." *Science* 337(6096): 816-21.

Jones, D. T. (1999). "Protein secondary structure prediction based on position-specific scoring matrices." *J Mol Biol* 292(2): 195-202.

Kleanthous, C., U. C. Kuhlmann, et al. (1999). "Structural and mechanistic basis of immunity toward endonuclease colicins." *Nat Struct Biol* 6(3): 243-52.

Lutz, S., M. Ostermeier, et al. (2001). "Rapid generation of incremental truncation libraries for protein engineering using alpha-phosphothioate nucleotides." *Nucleic Acids Res* 29(4): E16.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Makarova, K. S., N. V. Grishin, et al. (2006). "A putative RNA-interference-based immune system in prokaryotes: computational analysis of the predicted enzymatic machinery, functional analogies with eukaryotic RNAi, and hypothetical mechanisms of action." *Biol Direct* 1: 7.

Mali, P., L. Yang, et al. (2013). "RNA-guided human genome engineering via Cas9." *Science* 339(6121): 823-6.

Mojica, F. J., C. Diez-Villasenor, et al. (2009). "Short motif sequences determine the targets of the prokaryotic CRISPR defence system." *Microbiology* 155(Pt 3): 733-40.

Morgenstern, B. (2004). "DIALIGN: multiple DNA and protein sequence alignment at BiBiServ." *Nucleic Acids Res* 32(Web Server issue): W33-6.

Qi, L. S., M. H. Larson, et al. (2013). "Repurposing CRISPR as an RNA-guided platform for sequence-specific control of gene expression." *Cell* 152(5): 1173-83.

Reyon, D., S. Q. Tsai, et al. (2012). "FLASH assembly of TALENs for high-throughput genome editing." *Nat Biotechnol* 30(5): 460-5.

Sapranauskas, R., G. Gasiunas, et al. (2011). "The *Streptococcus thermophilus* CRISPR/Cas system provides immunity in *Escherichia coli*." *Nucleic Acids Res* 39(21): 9275-82.

Schutz, K., J. R. Hesselberth, et al. (2010). "Capture and sequence analysis of RNAs with terminal 2',3'-cyclic phosphates." *Rna* 16(3): 621-31.

Shub, D. A., H. Goodrich-Blair, et al. (1994). "Amino acid sequence motif of group I intron endonucleases is conserved in open reading frames of group II introns." *Trends Biochem Sci* 19(10): 402-4.

Sorek, R., C. M. Lawrence, et al. (2013). "CRISPR-mediated Adaptive Immune Systems in Bacteria and Archaea." *Annu Rev Biochem*.

van der Ploeg, J. R. (2009). "Analysis of CRISPR in *Streptococcus mutans* suggests frequent occurrence of acquired immunity against infection by M102-like bacteriophages." *Microbiology* 155(Pt 6): 1966-76.

Wang, L. and S. J. Brown (2006). "BindN: a web-based tool for efficient prediction of DNA and RNA binding sites in amino acid sequences." *Nucleic Acids Res* 34(Web Server issue): W243-8.

The invention claimed is:

1. A method of genome targeting in a mammalian cell comprising:
   (a) selecting a target nucleic acid sequence comprising a PAM motif,
   (b) providing a guide RNA comprising a sequence complementary to the target nucleic acid sequence;
   (c) providing two nucleic acids encoding two separate Split Cas9, one Split Cas9 providing a RuvC domain and another Split Cas9 providing an HNH domain,
   wherein said RuvC domain comprises at least one RuvC motif sequence D-I-G-T-N-S-V-G-W-A (amino acids 10-19 of SEQ ID NO:52) and has at least 90% identity with the amino acid sequence of SEQ ID NO:52,
   wherein said HNH domain comprises at least one HNH motif sequence Y-D-V-D-H-I-V-P-Q-S-F-L-K-D-D-S (amino acids 589-604 of SEQ ID NO:53) and has at least 90% identity with the amino acid sequence of SEQ ID NO:53 and
   wherein one of the Split Cas9 is less than 1000 amino acids long; and
   (d) introducing into the cell said guide RNA and said two nucleic acids encoding two separate Split Cas9; such that said two separate Split Cas9 process the target nucleic acid sequence in the cell.

2. The method of claim 1, wherein the C-terminal domain of the Split Cas9 providing an HNH domain is truncated after the HNH motif sequence Y-D-V-D-H-I-V-P-Q-S-F-L-K-D-D-S (amino acids 589-604 of SEQ ID NO:53).

3. The method of claim 1, wherein said RuvC domain comprises the amino acid sequence of SEQ ID NO: 4.

4. The method of claim 1, wherein said RuvC domain comprises the amino acid sequence of SEQ ID NO: 52.

5. The method of claim 1, wherein said HNH domain comprises the amino acid sequence of SEQ ID NO: 13.

6. The method of claim 1, wherein said HNH domain comprises the amino acid sequence of SEQ ID NO: 53.

7. A method of genome targeting in a mammalian cell comprising:
   (a) selecting a target nucleic acid sequence comprising a PAM motif,
   (b) providing a guide RNA comprising a sequence complementary to the target nucleic acid sequence;
   (c) providing two nucleic acids encoding two separate Split Cas9, one Split Cas9 providing a RuvC domain and another Split Cas9 providing an HNH domain,
   wherein said RuvC domain comprises at least one RuvC motif sequence D-I-G-T-N-S-V-G-W-A (amino acids 10-19 of SEQ ID NO:52) and has at least 90% identity with the amino acid sequence of SEQ ID NO:52,
   wherein said HNH domain comprises at least one HNH motif sequence Y-D-V-D-H-I-V-P-Q-S-F-L-K-D-D-S (amino acids 589-604 of SEQ ID NO:53) and has at least 90% identity with the amino acid sequence of SEQ ID NO:53 and
   wherein one of the Split Cas9 is less than 800 amino acids long; and
   (d) introducing into the cell said guide RNA and said two nucleic acids encoding two separate Split Cas9; such that said two separate Split Cas9 process the target nucleic acid sequence in the cell.

8. A method of genome targeting in a mammalian cell comprising:
   (a) selecting a target nucleic acid sequence comprising a PAM motif,
   (b) providing a guide RNA comprising a sequence complementary to the target nucleic acid sequence;
   (c) providing two nucleic acids encoding two separate Split Cas9, one Split Cas9 providing a RuvC domain and another Split Cas9 providing an HNH domain,
   wherein said RuvC domain comprises at least one RuvC motif sequence D-I-G-T-N-S-V-G-W-A (amino acids 10-19 of SEQ ID NO:52) and has at least 90% identity with the amino acid sequence of SEQ ID NO:52,
   wherein said HNH domain comprises at least one HNH motif sequence Y-D-V-D-H-I-V-P-Q-S-F-L-K-D-D-S (amino acids 589-604 of SEQ ID NO:53) and has at least 90% identity with the amino acid sequence of SEQ ID NO:53 and
   wherein one of the Split Cas9 is less than 500 amino acids long; and
   (d) introducing into the cell said guide RNA and said two nucleic acids encoding two separate Split Cas9; such that said two separate Split Cas9 process the target nucleic acid sequence in the cell.

9. The method of claim 1, wherein the wild type sequence of S. pyogenes Cas9 has been divided into two nucleic acids encoding the two separate Split Cas9.

10. The method of claim 1, wherein said two separate Split Cas9 are the N-terminal domain comprising SEQ ID NO:52 and the C-terminal domain comprising SEQ ID NO:53.

11. The method of claim 1, further comprising introducing an exogenous nucleic acid sequence comprising at least one sequence homologous to at least a portion of the target nucleic acid sequence.

12. The method of claim 1, wherein said RuvC domain has at least 95% amino sequence identity with the amino acid sequence of SEQ ID NO: 52.

13. The method of claim 1, wherein said HNH domain has at least 95% amino sequence identity with the amino acid sequence of SEQ ID NO: 53.

14. The method of claim 12, wherein said HNH domain has at least 95% amino sequence identity with the amino acid sequence of SEQ ID NO: 53.

15. The method of claim 1, wherein said two separate Split Cas9 generate a double-strand break in the target nucleic acid sequence in the cell.

16. The method of claim 7, wherein said two separate Split Cas9 generate a double-strand break in the target nucleic acid sequence in the cell.

17. The method of claim 8, wherein said two separate Split Cas9 generate a double-strand break in the target nucleic acid sequence in the cell.

18. The method of claim 15, wherein repair of the double-stranded break double-strand break in the target nucleic acid induces a genetic modification of the target nucleic acid.

19. The method of claim 16, wherein repair of the double-stranded break double-strand break in the target nucleic acid induces a genetic modification of the target nucleic acid.

20. The method of claim 17, wherein repair of the double-stranded break double-strand break in the target nucleic acid induces a genetic modification of the target nucleic acid.

21. The method of claim 20, wherein the C-terminus of the split Cas9 comprising the RuvC domain is between positions G166 and P800.

22. The method of claim 21, wherein the N-terminus of the split Cas9 comprising the HNH domain is between positions G166 and P800.

23. The method of claim 22, wherein while the HNH domain is truncated after the HNH motif sequence Y-D-V-D-H-I-V-P-Q-S-F-L-K-D-D-S (amino acids 589-604 of SEQ ID NO:53).

24. The method of claim 22, wherein said two separate Split Cas9 are the N-terminal domain consisting of the amino acid sequence of SEQ ID NO:52 and the C-terminal domain consisting of the amino acid sequence of SEQ ID NO:53.

25. The method of claim 14, wherein said two separate Split Cas9 are an N-terminal domain comprising amino acids 1-166 of the amino acid sequence of SEQ ID NO:52 and a C-terminal domain comprising amino acids 800-981 of the amino acid sequence of SEQ ID NO:53.

26. The method of claim 14, wherein said two separate Split Cas9 are an N-terminal domain comprising amino acids 1-166 of the amino acid sequence of SEQ ID NO:52 and a C-terminal domain comprising amino acids 800-1055 of the amino acid sequence of SEQ ID NO:53.

27. The method of claim 14, wherein said two separate Split Cas9 are an N-terminal domain comprising an amino acid sequence corresponding to amino acids 1-166 of the amino acid sequence of SEQ ID NO:52 and a C-terminal domain comprising an amino acid sequence corresponding to amino acids 800-981 of the amino acid sequence of SEQ ID NO:53.

28. The method of claim 14, wherein said two separate Split Cas9 are an N-terminal domain comprising an amino acid sequence corresponding to amino acids 1-166 of the amino acid sequence of SEQ ID NO:52 and a C-terminal domain comprising an amino acid sequence corresponding to amino acids 800-1055 of the amino acid sequence of SEQ ID NO:53.

* * * * *

SEQUENCE LISTING

<160> NUMBER OF SEQ ID NOS: 64

<210> SEQ ID NO 1
<211> LENGTH: 10
<212> TYPE: PRT
<213> ORGANISM: artificial sequence
<220> FEATURE:
<223> OTHER INFORMATION: RuvC motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Asp Xaa Gly Xaa Xaa Ser Xaa Gly Trp Ala
1               5                   10

<210> SEQ ID NO 2
<211> LENGTH: 16
<212> TYPE: PRT
<213> ORGANISM: artificial sequence
<220> FEATURE:
<223> OTHER INFORMATION: HNH motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 2

Tyr Xaa Xaa Asp His Xaa Xaa Pro Xaa Ser Xaa Xaa Xaa Asp Xaa Ser
1               5                   10                  15

<210> SEQ ID NO 3
<211> LENGTH: 1368
<212> TYPE: PRT
<213> ORGANISM: Streptococcus pyogenes serotype M1
<220> FEATURE:
<221> NAME/KEY: MISC_FEATURE
<223> OTHER INFORMATION: Cas9

<400> SEQUENCE: 3

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

```
Gly Ala Leu Leu Phe Asp Ser Gly Glu Thr Ala Glu Ala Thr Arg Leu
         50                  55                  60
Lys Arg Thr Ala Arg Arg Tyr Thr Arg Lys Asn Arg Ile Cys
 65                  70                  75                  80
Tyr Leu Gln Glu Ile Phe Ser Asn Glu Met Ala Lys Val Asp Asp Ser
                         85                  90                  95
Phe Phe His Arg Leu Glu Glu Ser Phe Leu Val Glu Glu Asp Lys Lys
                 100                 105                 110
His Glu Arg His Pro Ile Phe Gly Asn Ile Val Asp Glu Val Ala Tyr
             115                 120                 125
His Glu Lys Tyr Pro Thr Ile Tyr His Leu Arg Lys Lys Leu Val Asp
         130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                 165                 170                 175
Asp Asn Ser Asp Val Asp Lys Leu Phe Ile Gln Leu Val Gln Thr Tyr
             180                 185                 190
Asn Gln Leu Phe Glu Glu Asn Pro Ile Asn Ala Ser Gly Val Asp Ala
         195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                 245                 250                 255
Asp Leu Ala Glu Asp Ala Lys Leu Gln Leu Ser Lys Asp Thr Tyr Asp
             260                 265                 270
Asp Asp Leu Asp Asn Leu Leu Ala Gln Ile Gly Asp Gln Tyr Ala Asp
         275                 280                 285
Leu Phe Leu Ala Ala Lys Asn Leu Ser Asp Ala Ile Leu Leu Ser Asp
290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                 325                 330                 335
Ala Leu Val Arg Gln Gln Leu Pro Glu Lys Tyr Lys Glu Ile Phe Phe
             340                 345                 350
Asp Gln Ser Lys Asn Gly Tyr Ala Gly Tyr Ile Asp Gly Gly Ala Ser
         355                 360                 365
Gln Glu Glu Phe Tyr Lys Phe Ile Lys Pro Ile Leu Glu Lys Met Asp
         370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                 405                 410                 415
Gly Glu Leu His Ala Ile Leu Arg Arg Gln Glu Asp Phe Tyr Pro Phe
             420                 425                 430
Leu Lys Asp Asn Arg Glu Lys Ile Glu Lys Ile Leu Thr Phe Arg Ile
         435                 440                 445
Pro Tyr Tyr Val Gly Pro Leu Ala Arg Gly Asn Ser Arg Phe Ala Trp
450                 455                 460
```

-continued

```
Met Thr Arg Lys Ser Glu Glu Thr Ile Thr Pro Trp Asn Phe Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
```

```
            885                 890                 895
Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290
```

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 4
<211> LENGTH: 166
<212> TYPE: PRT
<213> ORGANISM: artificial sequence
<220> FEATURE:
<223> OTHER INFORMATION: RuvC domain of S. pyogenes Cas9

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly
                165

<210> SEQ ID NO 5
<211> LENGTH: 183
<212> TYPE: PRT
<213> ORGANISM: Lactobacillus salivarius (strain CECT 5713)
<220> FEATURE:
<221> NAME/KEY: MISC_FEATURE
<223> OTHER INFORMATION: D8IJI3_LACSC

<400> SEQUENCE: 5

Met Glu Arg Tyr His Ile Gly Leu Asp Ile Gly Thr Ser Ser Ile Gly
1               5                   10                  15

Trp Ala Val Ile Gly Asp Asp Phe Lys Ile Lys Arg Lys Lys Gly Lys
                20                  25                  30

Asn Leu Ile Gly Val Arg Leu Phe Lys Glu Gly Asp Thr Ala Ala Glu
            35                  40                  45

```
Arg Arg Ser Phe Arg Thr Gln Arg Arg Leu Asn Arg Arg Lys Trp
 50                  55                  60

Arg Leu Lys Leu Leu Glu Glu Ile Phe Asp Pro Tyr Met Ala Glu Val
 65                  70                  75                  80

Asp Glu Tyr Phe Phe Ala Arg Leu Lys Glu Ser Asn Leu Ser Pro Lys
                 85                  90                  95

Asp Ser Asn Lys Lys Tyr Leu Gly Ser Leu Leu Phe Pro Asp Ile Ser
                100                 105                 110

Asp Ser Asn Phe Tyr Asp Lys Tyr Pro Thr Ile Tyr His Leu Arg Arg
                115                 120                 125

Asp Leu Met Glu Lys Asp Lys Lys Phe Asp Leu Arg Glu Ile Tyr Leu
130                 135                 140

Ala Ile His His Ile Val Lys Tyr Arg Gly Asn Phe Leu Glu Lys Val
145                 150                 155                 160

Pro Ala Lys Asn Tyr Lys Asn Ser Gly Ala Ser Ile Gly Phe Leu Leu
                165                 170                 175

Glu Glu Val Asn Arg Phe Ile
                180

<210> SEQ ID NO 6
<211> LENGTH: 669
<212> TYPE: PRT
<213> ORGANISM: Lactobacillus delbrueckii subsp. bulgaricus
<220> FEATURE:
<221> NAME/KEY: MISC_FEATURE
<223> OTHER INFORMATION: F0K1W4_LACD2

<400> SEQUENCE: 6

Met Ala Lys Pro Lys Asp Tyr Thr Ile Gly Leu Asp Ile Gly Thr Asn
  1               5                  10                  15

Ser Val Gly Trp Val Val Thr Asp Asp Gln Asn Asn Ile Leu Arg Ile
                 20                  25                  30

Lys Gly Lys Lys Ala Ile Gly Ala Arg Leu Phe Thr Glu Gly Lys Val
                 35                  40                  45

Ala Ala Glu Arg Arg Ser Phe Arg Thr Thr Arg Arg Leu Ser Arg
 50                  55                  60

Arg Arg Trp Arg Ile Lys Met Leu Glu Glu Leu Phe Asp Glu Glu Ile
 65                  70                  75                  80

Ala Lys Val Asp Pro Ser Phe Phe Ala Arg Leu His Glu Ser Trp Ile
                 85                  90                  95

Ser Pro Lys Asp Lys Arg Lys Arg Tyr Ser Ala Ile Val Phe Pro Ser
                100                 105                 110

Pro Glu Glu Asp Lys Lys Phe His Glu Ser Tyr Pro Thr Ile Tyr His
                115                 120                 125

Leu Arg Asp Lys Leu Met Lys Asp Asp Gln Lys His Asp Ile Arg Glu
130                 135                 140

Ile Tyr Ile Ala Val His Gln Met Ile Lys Ala Arg Gly Asn Phe Leu
145                 150                 155                 160

His Asp Glu Ser Val Glu Thr Tyr Arg Ser Gly Met Ser Ser Leu Gly
                165                 170                 175

Gly Arg Ser Glu Arg Asn Ile Leu Ser Val Gln Thr Leu Glu Glu Leu
                180                 185                 190

Asn Asp Leu Phe Ala Glu Asn Glu Gly Thr Glu Glu Val Glu Leu Asn
                195                 200                 205

Val Ala Ser Ala Glu Gln Ile Asn Asp Ile Leu Thr Gly Gly His Leu
210                 215                 220
```

```
Asn Ala Asp Ser Gln Lys Glu Ile Ser Asn Leu Leu Pro Ser Ser
225                 230                 235                 240

Phe Pro Ser Phe Asp Asp Lys Ala Lys Glu Lys Gln Val Lys Lys Leu
            245                 250                 255

Ile Asn Asn Val Ala Thr Asn Ile Ser Lys Ala Trp Leu Gly Tyr Lys
                260                 265                 270

Ala Asp Phe Ser Thr Ile Leu Asn Leu Ala Lys Val Asp Lys Asp Gln
            275                 280                 285

Lys Lys Ile Phe Ala Phe Ala Leu Gln Gly Gly Asp Glu Glu Asp Lys
290                 295                 300

Val Gln Glu Leu Glu Ser Leu Leu Glu Gln Ser Gln Thr Asp Ile Val
305                 310                 315                 320

Asp Arg Leu Ile Glu Ile Arg His Ala Ile Val Leu Ser Glu Ile Val
                325                 330                 335

Pro Val Gly Met Thr Leu Ser Glu Ala Met Ile Asp Lys Tyr Asp Gln
            340                 345                 350

His Lys Glu Asp Leu Ile Thr Leu Lys Ala Val Ile Arg Asn Thr Lys
        355                 360                 365

Asp Lys Lys Lys Ala Ala Lys Leu Gln Ala Ile Tyr Asp Leu Tyr Val
370                 375                 380

Lys Lys Arg His Ala Asp Leu Ala Lys Ala Met Lys Leu Thr Gly Ile
385                 390                 395                 400

Lys Lys Arg Ser Glu Leu Leu Asp Pro Glu Glu Leu Lys Lys Gly Ile
                405                 410                 415

Ser Ser Leu Leu Asp Asp Ser Pro Glu Ala Val Glu Ile Lys Gln Arg
            420                 425                 430

Leu Glu Glu Lys Thr Phe Leu Pro Leu Gln Arg Ser Asn Asn Asn Gly
                435                 440                 445

Val Ile Pro Asn Gln Leu His Gln Val Glu Leu Asp Glu Ile Ile Lys
450                 455                 460

Lys Gln Ser Lys Tyr Tyr Pro Phe Leu Ala Glu Lys Asn Pro Asp Glu
465                 470                 475                 480

Ser Glu Glu Ala Gln Lys Ala Pro Thr Lys Leu Asp Ala Leu Leu
                485                 490                 495

Thr Phe Arg Val Pro Tyr Tyr Val Gly Pro Met Ile Thr Lys Glu Glu
            500                 505                 510

Gln Glu Ala Gln Asn Gly His Ser Phe Ala Trp Met Val Arg Arg Asp
                515                 520                 525

Pro Gln Asp His Glu Ala Ile Thr Pro Trp Asn Phe Glu Lys Lys Val
            530                 535                 540

Asp Lys Met Ala Ser Ala Thr Gln Phe Ile Lys Arg Met Thr Thr Lys
545                 550                 555                 560

Asp Thr Tyr Leu Leu Gly Glu Asp Val Leu Pro Ala Ser Ser Leu Lys
                565                 570                 575

Tyr Gln Leu Phe Thr Val Leu Asn Glu Leu Asn Asn Leu Arg Val Asn
            580                 585                 590

Gly Lys Lys Leu Thr Ser Asp Glu Lys Glu Gln Val Ile Glu Gly Leu
        595                 600                 605

Phe Lys Lys Gln Lys Thr Val Lys Ala Asp Lys Phe Val Lys Tyr Trp
610                 615                 620

Gln Ala Lys His Ile Gly Ala Asp Ile Lys Val Lys Gly Leu Ser Asp
625                 630                 635                 640
```

```
Pro Ser Lys Phe Asn Ser Thr Met Ser Thr Tyr Ile Asp Phe Lys Lys
                    645                 650                 655

Ile Phe Gly Asp Gln Leu Asn Asp Val Asn Arg Gln Arg
                660                 665
```

```
<210> SEQ ID NO 7
<211> LENGTH: 142
<212> TYPE: PRT
<213> ORGANISM: Lactobacillus iners SPIN 2503V10-D
<220> FEATURE:
<221> NAME/KEY: MISC_FEATURE
<223> OTHER INFORMATION: E1NX15_9LACO

<400> SEQUENCE: 7
```

```
Met Asn Asn Tyr Tyr Leu Gly Leu Asp Leu Gly Thr Asn Ser Val
1               5                   10                  15

Gly Trp Ala Val Thr Asp His Tyr Asn Ile Ile Lys Phe His Gly
                20                  25                  30

Lys His Met Trp Gly Met Arg Leu Phe Glu Glu Ala Glu Thr Ala Lys
                35                  40                  45

Asp Arg Arg Leu His Arg Gln Ala Arg Arg Arg Gln Arg Leu Val
    50                  55                  60

Glu Arg Ile Asn Leu Leu Glu Glu Leu Phe Asp Lys Glu Ile Ser Lys
65                  70                  75                  80

Val Asp Gln Gly Phe Phe Ala Arg Lys Lys Glu Ser Asp Leu His Phe
                85                  90                  95

Glu Asp Lys Thr Thr Lys Ser Glu Tyr Ala Leu Phe Asn Asp Lys Ser
                100                 105                 110

Tyr Thr Asp Arg Asp Tyr Tyr Lys Gln Tyr Pro Thr Ile Phe His Leu
                115                 120                 125

Ile Met Asp Leu Ile Glu Asn Asp Lys Lys Gly Ile Tyr Val
                130                 135                 140
```

```
<210> SEQ ID NO 8
<211> LENGTH: 344
<212> TYPE: PRT
<213> ORGANISM: Helicobacter pullorum MIT 98-5489
<220> FEATURE:
<221> NAME/KEY: MISC_FEATURE
<223> OTHER INFORMATION: C5F1Z4_9HELI

<400> SEQUENCE: 8
```

```
Met Lys Ile Leu Gly Phe Asp Ile Gly Ile Ala Ser Ile Gly Trp Ala
1               5                   10                  15

Phe Val Glu Asn Gly Glu Leu Lys Asp Cys Gly Val Arg Ile Phe Thr
                20                  25                  30

Lys Ala Glu Asn Pro Lys Thr Gly Asp Ser Leu Ala Met Pro Arg Arg
                35                  40                  45

Glu Ala Arg Ser Val Arg Arg Arg Leu Ala Arg Arg Lys Gly Arg Leu
    50                  55                  60

Glu Thr Leu Lys Arg Leu Leu Ala Lys Glu Trp Asp Leu Cys Tyr Glu
65                  70                  75                  80

Asp Tyr Ile Ala Ala Asp Gly Glu Leu Pro Lys Ala Phe Met Gly Lys
                85                  90                  95

Asn Leu Thr Asn Pro Tyr Val Leu Arg Tyr Glu Ala Leu Gln Arg Leu
                100                 105                 110

Leu Ser Lys Glu Glu Leu Val Arg Val Val Leu His Ile Ala Lys His
                115                 120                 125
```

```
Arg Gly Tyr Gly Asn Lys Asn Ala Lys Ile Thr Lys Ser Glu Glu Ser
            130                 135                 140

Lys Arg Glu Gln Gly Lys Ile Leu Ser Ala Leu Ala Thr Asn Ala Ser
145                 150                 155                 160

Val Ile Ala Arg Tyr Arg Thr Val Gly Glu Tyr Phe Tyr Lys Glu Phe
                165                 170                 175

Cys Glu Val Ile Lys Asn Pro Gln Gly Leu Asn Thr Asn Glu Asn Cys
            180                 185                 190

Thr Gln Pro Lys Val Arg Val Leu Lys Pro Ile Arg Asn Lys Gly Gly
        195                 200                 205

Glu Tyr Thr Asn Cys Ile Leu Gln Glu Asp Leu Gln Arg Glu Leu Arg
    210                 215                 220

Cys Ile Phe Glu His Gln Lys Gly Phe Gly Phe Ser Ile Thr Gln Glu
225                 230                 235                 240

Phe Gln Asp Lys Ile Leu Lys Ile Ala Phe Tyr Gln Arg Ser Leu Lys
                245                 250                 255

Asp Phe Ser His Leu Val Gly Lys Cys Thr Phe Tyr Pro Asp Glu Pro
            260                 265                 270

Arg Ala Pro Lys Phe Ser Leu Ser Ala Ile Glu Phe Ile Thr Lys Ala
        275                 280                 285

Lys Ala Ile Asn Leu Leu Ala Ser Ile Ala Lys Glu Ser Gly Glu Val
    290                 295                 300

Trp Asp Lys Glu Gln Trp Arg Glu Arg Leu Asp Ser Val Phe Ser Ala
305                 310                 315                 320

Val Cys Glu Arg Gly Ile Asn Thr Ile Pro Ser Ser His Phe Leu
                325                 330                 335

Asn Ile Phe Asp Ile Leu Tyr Leu
            340

<210> SEQ ID NO 9
<211> LENGTH: 349
<212> TYPE: PRT
<213> ORGANISM: Bacteroides coprosuis DSM 18011
<220> FEATURE:
<221> NAME/KEY: MISC_FEATURE
<223> OTHER INFORMATION: F3ZS86_9BACE

<400> SEQUENCE: 9

Met Lys Lys Ile Leu Gly Leu Asp Ile Gly Thr Asn Ser Val Gly Trp
1               5                   10                  15

Ala Val Val Asn Thr Asn Gln Glu Gly Glu Pro Ser Gln Ile Glu Lys
            20                  25                  30

Leu Gly Ser Arg Ile Ile Pro Met Ser Gln Asp Ile Leu Asp Lys Phe
        35                  40                  45

Gly Gln Gly Gln Thr Val Ser Ser Thr Ala Ser Arg Thr Asp Tyr Arg
    50                  55                  60

Gly Ile Arg Arg Leu Arg Glu Arg Ser Leu Leu Arg Arg Glu Arg Leu
65                  70                  75                  80

His Arg Val Leu His Ile Leu Asp Phe Leu Pro Lys His Tyr Ala Asp
                85                  90                  95

Ser Ile Gly Trp Asp Pro Arg Asn Ser Lys Thr Tyr Gly Lys Phe Leu
            100                 105                 110

Pro Gly Thr Glu Val Lys Leu Ala Trp Val Pro Thr Ala Asp Gly His
        115                 120                 125

Gln Phe Leu Phe Tyr Ser Thr Tyr Leu Glu Met Leu Glu Asp Leu Lys
    130                 135                 140
```

```
Gln Thr Gln Ala Gln Leu Phe Glu Thr Ser Gln Thr Pro Val Pro Leu
145                 150                 155                 160

Asp Trp Thr Ile Tyr Tyr Leu Arg Lys Lys Ala Leu Thr Gln Pro Ile
                165                 170                 175

Thr Lys His Glu Leu Ala Trp Leu Leu Leu His Phe Asn Thr Lys Arg
            180                 185                 190

Gly Tyr Tyr Gln Arg Arg Gly Glu Leu Glu Asp Thr Pro Thr Asp Lys
        195                 200                 205

Leu Val Glu Tyr His Ala Leu Lys Val Val Asp Val Glu Val Asp Pro
    210                 215                 220

Glu Asp Gln Ser Lys Lys Pro Trp Tyr Phe Val His Leu Glu Asn Gly
225                 230                 235                 240

Trp Ile Tyr Lys Arg Gln Ser Ser Glu Pro Leu Asp Asn Trp Lys Gly
                245                 250                 255

Leu Val Lys Glu Phe Ile Val Thr Thr His Leu Asp Lys Glu Gly Lys
            260                 265                 270

Pro Lys Leu Asp Lys Glu Gly Glu Val Arg Arg Ser Phe Ser Ser Pro
        275                 280                 285

Lys Glu Asp Asp Trp Thr Leu Val Lys Lys Thr Glu Asn Asp Leu
290                 295                 300

Glu Lys Ser Gly Leu Thr Val Gly Ala Tyr Ile Tyr Gln Thr Leu Leu
305                 310                 315                 320

Asn Lys Pro Asn Gln Lys Ile Arg Gly Gly Leu Ile Lys His Ile Glu
                325                 330                 335

Arg Asn Tyr Tyr Val Glu Glu Leu Glu Gln Ile Leu Arg
            340                 345

<210> SEQ ID NO 10
<211> LENGTH: 198
<212> TYPE: PRT
<213> ORGANISM: Fusobacterium necrophorum subsp. funduliforme 1_1_36S
<220> FEATURE:
<221> NAME/KEY: MISC_FEATURE
<223> OTHER INFORMATION: H1D479_9FUSO

<400> SEQUENCE: 10

Met Lys Lys Phe Glu Asn Tyr Tyr Leu Gly Leu Asp Ile Gly Thr Ser
1               5                   10                  15

Ser Ile Gly Trp Ala Val Thr Asn Ser Gln Tyr Asp Ile Leu Lys Phe
            20                  25                  30

Asn Gly Lys Tyr Met Trp Gly Thr Arg Leu Phe Pro Glu Ala Asn Thr
        35                  40                  45

Ala Gln Glu Arg Arg Ile His Arg Ser Arg Arg Arg Leu Lys Arg
    50                  55                  60

Arg Lys Glu Arg Ile Gln Ile Leu Gln Met Leu Phe Asp Lys Glu Ile
65                  70                  75                  80

Ala Lys Ile Asp Ser Gly Phe Phe Gln Arg Leu Lys Asp Ser Lys Tyr
                85                  90                  95

Tyr Lys Glu Asp Lys Thr Glu Lys Gln Thr Asn Ser Ile Phe His Asp
            100                 105                 110

Lys Asp Tyr Ser Asp Lys Glu Tyr His Gln Asp Phe Pro Thr Ile Tyr
        115                 120                 125

His Leu Arg Lys Phe Leu Leu Glu Gly Asn Lys Pro Lys Asp Ile Arg
    130                 135                 140

Phe Val Tyr Leu Ala Leu His His Ile Leu Thr His Arg Gly His Phe
```

```
                145                 150                 155                 160
Leu Phe Pro Asp Met Glu Val Ser Asn Val Thr Glu Phe Ser Asn Ile
                    165                 170                 175

Phe Ser Glu Leu Lys Gln Tyr Leu Tyr Asp Glu Met Asp Leu Asp Phe
                    180                 185                 190

Glu Trp Lys Thr Glu Asn
            195

<210> SEQ ID NO 11
<211> LENGTH: 857
<212> TYPE: PRT
<213> ORGANISM: Lactobacillus crispatus FB077-07
<220> FEATURE:
<221> NAME/KEY: MISC_FEATURE
<223> OTHER INFORMATION: K1M766_9LACO

<400> SEQUENCE: 11

Met Thr Lys Leu Asn Asn Glu Tyr Met Val Gly Leu Asp Ile Gly Thr
1               5                   10                  15

Asn Ser Cys Gly Trp Val Ala Thr Asp Phe Asp Asn Asn Ile Leu Lys
                20                  25                  30

Met His Gly Lys Arg Ala Leu Gly Ser His Leu Phe Asp Glu Gly Val
            35                  40                  45

Ser Ala Ala Asp Arg Arg Ala Phe Arg Thr Thr Arg Arg Arg Ile Lys
        50                  55                  60

Arg Arg Lys Trp Arg Leu Lys Leu Leu Glu Glu Ile Phe Asp Glu Glu
65                  70                  75                  80

Met Ala Lys Val Asp Pro Asn Phe Phe Ala Arg Leu Lys Glu Ser Gly
                85                  90                  95

Leu Ser Pro Leu Asp Thr Arg Lys Asn Val Ser Ser Ile Val Phe Pro
            100                 105                 110

Thr Lys Lys Met Asp Lys Gln Phe Tyr Lys Lys Phe Pro Thr Ile Tyr
        115                 120                 125

His Leu Arg Asn Ala Leu Met Lys Gln Asp Lys Lys Phe Asp Leu Arg
130                 135                 140

Ala Ile Tyr Ile Ala Ile His His Ile Val Lys Tyr Arg Gly Asn Phe
145                 150                 155                 160

Leu Ser Asn Ser Ser Ile Ser Asn Phe Ser Ala Ser Lys Ile Glu Ile
                165                 170                 175

Asp Arg Phe Val Asn Glu Leu Asn Asp Leu Tyr Ser Ile Phe Leu Pro
            180                 185                 190

Glu Ser Gly Val Ile Phe Asp Ala Gly Asn Ala Ser Lys Val Glu Asp
        195                 200                 205

Ile Ile Arg Asn Glu Gln Met Phe Lys Leu Asp Lys Ile Lys Glu Ile
210                 215                 220

Ala Asp Val Leu Pro Asp Thr Glu Asn Lys Ser Gly Leu Lys Leu Ser
225                 230                 235                 240

Lys Lys Ile Ser Lys Glu Ile Ser Lys Ala Ile Leu Gly Tyr Lys Ala
                245                 250                 255

Lys Phe Glu Ile Ile Leu Gln Val Asn Val Asp Lys Thr Asp Ser Ser
            260                 265                 270

Ile Trp Asn Phe Lys Leu Asn Asp Glu Asn Ala Asp Val Asn Leu Ser
        275                 280                 285

Glu Ile Thr Ser Asp Leu Thr Asp Thr Gln Leu Gln Ile Leu Asp Leu
    290                 295                 300
```

```
Val Arg Asn Leu Phe Ser Ala Ile Ser Leu Leu Asn Ile Val Asp Glu
305                 310                 315                 320

Gly Ser Thr Leu Ser Glu Ser Met Ile Arg Lys Tyr Asn Asp His Ala
            325                 330                 335

Gln Asp Leu Lys Leu Leu Lys Thr Val Ile Lys Asn His Ser Asp Arg
                340                 345                 350

Lys Lys Ala His Asn Leu Gln Leu Ala Tyr Asp Lys Tyr Val Asn Asn
            355                 360                 365

Arg His Phe Val Asp Val Glu Thr Lys Lys Ala Phe Pro Asn Lys His
    370                 375                 380

Leu Tyr Arg Lys Ser Asp Phe Tyr Glu Ile Val Lys Lys Asn Leu Asp
385                 390                 395                 400

Ala Ser Lys Glu Ala Val Gln Ile Arg Lys Glu Ile Ala Leu Asp Lys
                405                 410                 415

Phe Met Pro Lys Gln Arg Ser Asp Glu Asn Gly Val Ile Pro Phe Gln
                420                 425                 430

Leu Asn Gln Ile Glu Leu Asp Lys Ile Ile Glu Asn Gln Gly Lys Tyr
            435                 440                 445

Tyr Pro Phe Leu Lys Glu Ile Asn Pro Ile Lys Ala His Arg Met Gln
450                 455                 460

Ala Pro Tyr Lys Leu Asp Glu Leu Ile Arg Phe Arg Val Pro Tyr Tyr
465                 470                 475                 480

Val Gly Pro Met Ile Glu Pro Thr Asn Ser Ser Tyr Pro Gln Thr Arg
                485                 490                 495

Gln Asn Gln Ser Phe Ala Trp Met Val Arg Lys Ala Lys Gly Arg Ile
            500                 505                 510

Thr Pro Trp Asn Phe Asp Glu Lys Val Asp Arg Gln Lys Ser Ala Asn
            515                 520                 525

Asn Phe Ile Lys Arg Leu Thr Thr Lys Asp Thr Tyr Leu Phe Gly Glu
            530                 535                 540

Asp Val Leu Pro Ala Asn Ser Leu Leu Tyr Gln Lys Tyr Thr Val Leu
545                 550                 555                 560

Asp Glu Leu Asn Lys Ile Ser Val Asn Gly Lys Lys Leu Ser Val Ser
                565                 570                 575

Val Lys Gln Glu Leu Tyr Glu Asp Leu Phe Lys Lys Asn Asn Thr Val
            580                 585                 590

Ser Ala Lys Gln Leu Lys Asn Trp Leu Ile Glu Asn Gln Lys Leu Pro
            595                 600                 605

Tyr Ile Lys Ile Lys Gly Leu Ala Asp Gln Thr Lys Phe Asn Ser Ser
        610                 615                 620

Leu Ser Thr Tyr Ile Lys Leu Lys Lys Ser Gly Leu Phe Val Asp Lys
625                 630                 635                 640

Leu Asp Ser Asn Glu Phe Arg Asp Phe Glu Lys Ile Ile Glu Trp
                645                 650                 655

Ser Thr Ile Phe Glu Asp Lys Gln Ile Tyr Ile Gln Lys Leu Gln Thr
            660                 665                 670

Ile Asp Trp Leu Thr Ala Lys Gln Ile Gln Phe Leu Gln Asn Ile Arg
        675                 680                 685

Leu Gln Gly Trp Gly Arg Leu Ser Lys Lys Leu Leu Thr Ala Ile Val
            690                 695                 700

Asp Ser Asn Gly Gln Asn Ile Ile Glu Gln Leu Trp Asn Ser Gln Gln
705                 710                 715                 720

Ile Phe Met Ser Ile Val Asn Lys Ala Asp Ile Lys Gly Thr Ile Thr
```

```
                725                 730                 735

Asp Ala Asn Gln Asp Leu Met His Ser Asn Ser Met Glu Asp Ile Leu
            740                 745                 750

Ser Glu Ala Tyr Thr Ser Pro Ala Asn Lys Lys Met Ile Arg Gln Val
        755                 760                 765

Val Lys Val Val His Asp Ile Gln Lys Ala Ala Ser Gly Gln Ala Pro
    770                 775                 780

Lys Gln Ile Ala Ile Glu Phe Ala Arg Glu Ser Arg Arg Asn Ser Lys
785                 790                 795                 800

Leu Ser Gln Thr Arg Gly His Lys Leu Gln Asp Ile Tyr Gln Lys Ile
            805                 810                 815

Ser Gly Asp Ile Val Asn Lys Asn Leu Lys Asp Lys Leu Ala Glu Tyr
        820                 825                 830

Ile Lys Asn Asn Gln Leu Ser Val Trp Glu Lys Asn Ser Phe Gln Met
    835                 840                 845

Asn Lys Asn Asp Gln Asp Phe Leu Phe
850                 855

<210> SEQ ID NO 12
<211> LENGTH: 131
<212> TYPE: PRT
<213> ORGANISM: Helicobacter hepaticus (strain ATCC 51449 / 3B1)
<220> FEATURE:
<221> NAME/KEY: MISC_FEATURE
<223> OTHER INFORMATION: Q7VG48_HELHP

<400> SEQUENCE: 12

Met Arg Ile Leu Gly Phe Asp Ile Gly Ile Thr Ser Ile Gly Trp Ala
1               5                   10                  15

Tyr Val Glu Ser Asn Glu Leu Lys Asp Cys Gly Val Arg Ile Phe Thr
            20                  25                  30

Lys Ala Glu Asn Pro Lys Asn Gly Asp Ser Leu Ala Ala Pro Arg Arg
        35                  40                  45

Glu Ala Arg Gly Ala Arg Arg Arg Leu Ala Arg Arg Lys Ala Arg Leu
    50                  55                  60

Asn Ala Ile Lys Arg Leu Leu Cys Lys Glu Phe Glu Leu Asn Leu Asn
65                  70                  75                  80

Asp Tyr Leu Ala Asn Asp Gly Glu Leu Pro Lys Ala Tyr Gln Thr Ser
            85                  90                  95

Lys Asp Thr Lys Ser Pro Tyr Glu Leu Tyr Thr Ala Phe His Trp Ile
        100                 105                 110

Ile Phe Ala Phe Cys Ser Ile Ala Ser Ser Leu Ser Asn Arg Gln Met
    115                 120                 125

Leu Pro Ile
    130

<210> SEQ ID NO 13
<211> LENGTH: 256
<212> TYPE: PRT
<213> ORGANISM: artificial sequence
<220> FEATURE:
<223> OTHER INFORMATION: large version of HNH domain of S. pyogenes Cas9

<400> SEQUENCE: 13

Pro Val Glu Asn Thr Gln Leu Gln Asn Glu Lys Leu Tyr Leu Tyr Tyr
1               5                   10                  15

Leu Gln Asn Gly Arg Asp Met Tyr Val Asp Gln Glu Leu Asp Ile Asn
            20                  25                  30
```

-continued

```
Arg Leu Ser Asp Tyr Asp Val Asp His Ile Val Pro Gln Ser Phe Leu
             35                  40                  45

Lys Asp Asp Ser Ile Asp Asn Lys Val Leu Thr Arg Ser Asp Lys Asn
 50                  55                  60

Arg Gly Lys Ser Asp Asn Val Pro Ser Glu Glu Val Val Lys Lys Met
 65                  70                  75                  80

Lys Asn Tyr Trp Arg Gln Leu Leu Asn Ala Lys Leu Ile Thr Gln Arg
                 85                  90                  95

Lys Phe Asp Asn Leu Thr Lys Ala Glu Arg Gly Gly Leu Ser Glu Leu
            100                 105                 110

Asp Lys Ala Gly Phe Ile Lys Arg Gln Leu Val Glu Thr Arg Gln Ile
            115                 120                 125

Thr Lys His Val Ala Gln Ile Leu Asp Ser Arg Met Asn Thr Lys Tyr
130                 135                 140

Asp Glu Asn Asp Lys Leu Ile Arg Glu Val Lys Val Ile Thr Leu Lys
145                 150                 155                 160

Ser Lys Leu Val Ser Asp Phe Arg Lys Asp Phe Gln Phe Tyr Lys Val
                165                 170                 175

Arg Glu Ile Asn Asn Tyr His His Ala His Asp Ala Tyr Leu Asn Ala
            180                 185                 190

Val Val Gly Thr Ala Leu Ile Lys Lys Tyr Pro Lys Leu Glu Ser Glu
        195                 200                 205

Phe Val Tyr Gly Asp Tyr Lys Val Tyr Asp Val Arg Lys Met Ile Ala
210                 215                 220

Lys Ser Glu Gln Glu Ile Gly Lys Ala Thr Lys Tyr Phe Phe Tyr
225                 230                 235                 240

Ser Asn Ile Met Asn Phe Phe Lys Thr Glu Ile Thr Leu Ala Asn Gly
                245                 250                 255
```

<210> SEQ ID NO 14
<211> LENGTH: 897
<212> TYPE: PRT
<213> ORGANISM: Lactobacillus salivarius (strain CECT 5713)
<220> FEATURE:
<221> NAME/KEY: MISC_FEATURE
<223> OTHER INFORMATION: D8IJI4_LACSC
<220> FEATURE:
<221> NAME/KEY: misc_feature
<222> LOCATION: (822)..(822)
<223> OTHER INFORMATION: Xaa can be any naturally occurring amino acid

<400> SEQUENCE: 14

```
Met Leu Ile Glu Ser Asp Glu Lys Asn Lys Leu Thr Phe Asn Asp Glu
 1               5                  10                  15

Asn Ile Asp Asp Ile Phe Asn Glu Leu Ser His Ser Leu Asp Asp Asn
             20                  25                  30

Gln Met Asp Leu Leu Thr Lys Thr Arg Glu Ile Tyr Phe Lys Phe Lys
         35                  40                  45

Leu Asn Met Ile Val Pro Thr Gly Tyr Thr Leu Ser Glu Ser Met Ile
 50                  55                  60

Glu Lys Tyr Glu Met His Lys Ala His Leu Lys Met Tyr Lys Glu Phe
 65                  70                  75                  80

Ile Asn Thr Leu Asn Ala Lys Asp Arg Lys Ile Leu Lys Asn Ala Tyr
                 85                  90                  95

Ser Asp Tyr Ile Asn Asn Glu Lys Ala Lys Ala Ala Asn Ala Gln Glu
            100                 105                 110
```

-continued

Asn Phe Tyr Lys Thr Ile Lys Lys Thr Ile Lys Asp Asn Asn Ser Asp
            115                 120                 125

Thr Ala Lys Lys Ile Ile Gly Leu Ile Asp Glu Gly Asn Phe Met Pro
        130                 135                 140

Lys Gln Arg Thr Gly Glu Asn Gly Val Ile Pro His Gln Leu His Gln
145                 150                 155                 160

Ile Glu Leu Asp Arg Ile Ile Glu Asn Gln Ala Lys Tyr Tyr Pro Trp
                165                 170                 175

Leu Ala Glu Glu Asn Pro Val Glu Lys Asn Arg Lys Phe Ala Lys Tyr
            180                 185                 190

Lys Leu Asp Glu Leu Val Thr Phe Arg Val Pro Tyr Tyr Val Gly Pro
        195                 200                 205

Leu Val Asp Lys Thr Glu Ser Asn Lys Asn Glu Lys Glu Thr Lys Phe
210                 215                 220

Ala Trp Met Val Arg Lys Ala Lys Gly Thr Ile Thr Pro Trp Asn Phe
225                 230                 235                 240

Glu Asn Leu Val Asp Arg Thr Glu Ser Ala Asn Arg Phe Ile Lys Arg
                245                 250                 255

Met Thr Ser Lys Asp Thr Tyr Ile Ile Gly Glu Asp Val Leu Pro Ala
            260                 265                 270

Ser Ser Leu Leu Tyr Glu Lys Phe Lys Val Leu Asn Glu Leu Asn Asn
        275                 280                 285

Ile Lys Val Asn Lys Lys Leu Asp Val Glu Gln Lys Gln His Val
290                 295                 300

Tyr Leu Asp Leu Phe Thr Thr Arg Lys Asn Val Thr Lys Asp Asn Leu
305                 310                 315                 320

Ala Thr Ser Leu Asn Cys Asp Val Glu Ser Ile Thr Gly Leu Ser Asp
                325                 330                 335

Asn Glu Lys Phe Asn Ser Ser Leu Ser Ser Tyr Ile Asp Leu Lys Ala
            340                 345                 350

Ile Leu Gly Asn Ala Val Asp Asp Cys Asn Lys Asn Lys Asp Leu Glu
        355                 360                 365

Lys Ile Ile Glu Tyr Ser Thr Ile Phe Glu Asp Gly Asn Ile Tyr Lys
370                 375                 380

Glu Lys Leu Ser Glu Ile Ser Trp Leu Thr Asp Glu Gln Ile Glu Lys
385                 390                 395                 400

Leu Ser Asn Ile His Phe Lys Gly Trp Gly Arg Leu Ser Lys Lys Leu
                405                 410                 415

Leu Thr Gln Ile Thr Asn Glu Asn Gly Glu Arg Ile Ile Asp Ala Leu
            420                 425                 430

Trp Asn Thr Ser Asn Asn Phe Ile Gln Ile Ile Ser Asp Glu Ser Ile
        435                 440                 445

Gln Ala Lys Leu Ala Glu Ile Asn Gly Glu Tyr Ala Asp Lys Ser Asn
450                 455                 460

Leu Glu Asp Ile Leu Asp Glu Ala Tyr Thr Ser Pro Gln Asn Lys Lys
465                 470                 475                 480

Ala Ile Arg Gln Val Met Lys Val Val Glu Asp Ile Glu Lys Ala Met
                485                 490                 495

Lys Cys Lys Pro Thr Ser Ile Ala Ile Glu Phe Thr Arg Arg Lys Gly
            500                 505                 510

Lys Ser Lys Leu Thr Asn Thr Arg Tyr Lys Lys Ile Ser Glu Thr Tyr
        515                 520                 525

Glu Lys Ile Thr Asp Glu Leu Ile Ser Glu Tyr Glu Leu Gly Lys Leu

```
        530                 535                 540
Gln Ser Lys Leu Asp Ser Lys Ala Asn Asn Met Arg Asp Ile Tyr Tyr
545                 550                 555                 560

Leu Tyr Phe Met Gln Leu Gly Arg Asp Met Tyr Thr Gly Glu Lys Ile
                565                 570                 575

Asn Ile Asp Glu Leu His Gln Tyr Tyr Asp Ile Asp His Ile Phe Pro
                580                 585                 590

Arg Ser Phe Ile Lys Asp Asn Ser Leu Asn Asn Arg Val Leu Thr Arg
            595                 600                 605

Lys Glu Ile Asn Asn Glu Lys Ala Asp Arg Thr Ala Ala Asp Leu
610                 615                 620

Tyr Ala Val Lys Met Gly Asp Phe Trp Arg Lys Leu Arg Lys Gln Gly
625                 630                 635                 640

Leu Ile Thr Glu Lys Lys Tyr Lys Asn Leu Leu Thr Arg Thr Asp Ser
                645                 650                 655

Ile Asp Lys Tyr Thr Lys Gln Ser Phe Ile Lys Arg Gln Leu Val Glu
                660                 665                 670

Thr Ser Gln Val Val Lys Met Ala Ala Asn Ile Leu Gln Asp Lys Tyr
            675                 680                 685

Ser Asn Thr Lys Ile Ile Glu Val Arg Ala Arg Leu Asn Ser Asp Leu
690                 695                 700

Arg Lys Glu Tyr Glu Leu Ile Lys Asn Arg Glu Val Asn Asp Tyr His
705                 710                 715                 720

His Ala Ile Asp Gly Tyr Leu Thr Ile Phe Ile Gly Gln Tyr Leu Tyr
                725                 730                 735

Lys Thr Tyr Pro Lys Leu Arg Ser Tyr Phe Val Tyr Asp Asp Phe Lys
                740                 745                 750

Lys Leu Asp Ser Asn Tyr Leu Lys His Met Asp Lys Phe Asn Phe Ile
            755                 760                 765

Trp Lys Leu Glu Asp Lys Lys Ala Glu Asp Val Tyr Asp Asn Val Asn
770                 775                 780

Asn Glu Phe Ile Leu Asn Val Pro Lys Met Lys Asp Tyr Ile Gln Lys
785                 790                 795                 800

Ile Tyr Asn Tyr Lys Tyr Met Leu Ile Ser Lys Glu Val Thr Thr Glu
                805                 810                 815

Ser Gly Ala Phe Tyr Xaa Glu Thr Lys Tyr Asn Ala Lys Thr Ile Asn
                820                 825                 830

Leu Ile Pro Ile Lys Lys Asp Lys Pro Thr Asn Ile Tyr Gly Gly Tyr
            835                 840                 845

Lys Gly Lys Val Ser Ser Tyr Met Met Leu Val Lys Ile Gln Lys Lys
850                 855                 860

Lys Glu Val Ile Tyr Lys Phe Val Gly Val Pro Arg Leu Trp Thr Asp
865                 870                 875                 880

Glu Leu Asp Arg Leu Ile Asp Thr Asp Glu Lys Lys Ala Leu Leu Lys
                885                 890                 895

Lys

<210> SEQ ID NO 15
<211> LENGTH: 544
<212> TYPE: PRT
<213> ORGANISM: Lactobacillus delbrueckii subsp. bulgaricus (strain
      2038)
<220> FEATURE:
<221> NAME/KEY: MISC_FEATURE
<223> OTHER INFORMATION: F0K1W6_LACD2
```

<400> SEQUENCE: 15

```
Met Thr Gly Cys Ala Asp Tyr Asp Val Asp His Ile Met Pro Gln Ser
1               5                   10                  15

Phe Val Lys Asp Asp Ser Leu Asp Asn Arg Val Leu Val Ala Arg Ala
            20                  25                  30

Val Asn Asn Gln Lys Ser Asp Lys Val Pro Ala Leu Leu Phe Gly Asn
        35                  40                  45

Lys Val Val Ala Asp Leu Gly Ile Thr Val Arg Glu Met Trp Asp Lys
50                  55                  60

Trp Gln Lys Leu Gly Met Ile Ser Lys Arg Lys Leu Ser Asn Leu Leu
65                  70                  75                  80

Thr Asp Pro Asp Ala Leu Thr Glu Tyr Arg Ala Gln Gly Phe Ile Arg
                85                  90                  95

Arg Gln Leu Val Glu Thr Ser Gln Val Ile Lys Leu Thr Ala Thr Ile
            100                 105                 110

Leu Gln Ser Glu Phe Pro Asp Ser Lys Ile Ile Glu Val Pro Ala Lys
        115                 120                 125

Tyr Asn Ser Ile Val Arg Lys Gln Phe Asp Leu Tyr Lys Ser Arg Glu
130                 135                 140

Val Asn Asp Phe His His Ala Ile Asp Ala Tyr Leu Ser Thr Ile Val
145                 150                 155                 160

Gly Asn Tyr Leu Tyr Gln Val Tyr Pro Asn Leu Arg Arg Met Phe Val
                165                 170                 175

Tyr Gly Glu Phe Lys Lys Phe Ser Ser Asn Ala Glu Glu Ser Ala His
            180                 185                 190

Asp Val Ala Arg Arg Val Lys Ser Met Asn Phe Leu Asp Asp Leu Leu
        195                 200                 205

Arg Gly Thr His Gly Asp Asn Ile Tyr Cys Arg Ser Thr Gly Glu Ile
210                 215                 220

Val Phe Asn Arg Asn Asp Ile Ile Ser Lys Leu Lys Gln Ala Tyr Ser
225                 230                 235                 240

Phe Lys Gln Met Leu Val Thr Gln Glu Val Phe Thr Lys Lys Ser Ala
                245                 250                 255

Leu Phe Asp Gln Thr Val Tyr Pro Ser Pro Glu Arg Asp Ser Lys Lys
            260                 265                 270

Arg Ser Gly Leu Ile Pro Arg Lys Gly Met Asp Thr Glu Ile Tyr
        275                 280                 285

Gly Gly Tyr Ser Gly Asn Lys Asp Ala Tyr Phe Val Leu Ala Glu Ala
290                 295                 300

Val Lys Glu Lys Gly His Thr Leu Gln Ile Val Gly Val Pro Ile Arg
305                 310                 315                 320

Ala Leu Asn Thr Leu Lys Asn Ser Ala Asn Tyr Ser Glu Lys Leu Leu
                325                 330                 335

Glu Ile Ile Lys Pro Gln Val Met Phe Asn Lys Asp Thr Gly Lys Pro
            340                 345                 350

Ile Lys Gly Ile Lys Asp Val Lys Ile Leu Met Asp Lys Ile Pro Cys
        355                 360                 365

Arg Gln Pro Val Leu Glu Gly Glu Ser Tyr Tyr Met Leu Ala Ser Ser
370                 375                 380

Lys Tyr Arg Tyr Ser Leu Lys Gln Ile Ser Leu Ser Gln Met Ser Met
385                 390                 395                 400

Lys Tyr Ile Leu Asp Tyr Ile Asp Asp Pro Asn Phe Asn Lys His Glu
```

```
                 405                 410                 415
Met Ile Asn Ile Asp Gln Gln Asp Glu Lys Glu Cys Leu Leu Ser Val
            420                 425                 430

Tyr Asp Glu Ile Leu Glu Lys Met Asp Lys Tyr Leu Pro Leu Phe Asp
            435                 440                 445

Ile Arg Ser Phe Arg Lys Lys Leu His Asp Gly Arg Asp Ala Phe Ile
            450                 455                 460

Ala Leu Pro Val Ala Ser Glu Glu Lys Lys Pro Gly Glu Val Asp Val
465                 470                 475                 480

Ile Arg Lys Ile Leu Lys Gly Leu His Ala Asn Ala Asp Ile Thr Asn
            485                 490                 495

Leu Ala Glu Leu Gly Phe Gly Thr Ala Ala Leu Gly Ala Leu Val Ser
            500                 505                 510

Thr Gly Gly Ile Lys Ile Ser Asp Asp Ala Val Phe Ile Tyr Gln Ser
            515                 520                 525

Pro Thr Gly Leu Phe Glu Arg Arg Val Lys Val Ser Asp Leu Leu Lys
530                 535                 540
```

<210> SEQ ID NO 16
<211> LENGTH: 534
<212> TYPE: PRT
<213> ORGANISM: Lactobacillus crispatus 214-1
<220> FEATURE:
<221> NAME/KEY: MISC_FEATURE
<223> OTHER INFORMATION: D4FGK2_9LACO

<400> SEQUENCE: 16

```
Arg Asp Ala Tyr Thr Asp Lys Pro Ile Asn Ile Asp Glu Val Ser Gln
1               5                   10                  15

Tyr Tyr Asp Ile Asp His Ile Leu Pro Gln Ser Phe Ile Lys Asp Asp
            20                  25                  30

Ser Leu Asn Asn Arg Val Leu Val Ala Lys Pro Ile Asn Asn Gly Lys
            35                  40                  45

Ser Asp Gly Val Pro Leu Lys Leu Phe Gly Asp Asn Leu Ala Thr Gly
50                  55                  60

Leu Gly Ile Thr Val Lys Gln Met Trp Asn Asn Trp Ala Asp Lys Gly
65                  70                  75                  80

Leu Ile Asn Lys Ala Lys Gln Asn Asn Leu Phe Leu Asp Pro Glu Asn
            85                  90                  95

Ile Asn Lys His Gln Ala Ser Gly Phe Ile Arg Lys Gln Leu Val Glu
            100                 105                 110

Thr Ser Gln Ile Ile Lys Leu Ala Thr Thr Ile Leu Gln Ala Glu Tyr
            115                 120                 125

Pro Lys Thr Lys Ile Ile Val Val Lys Ala Ser Ser Asn His Tyr Leu
130                 135                 140

Arg Asn Glu Phe Asp Leu Tyr Lys Ser Arg Glu Val Asn Asp Tyr His
145                 150                 155                 160

His Ala Ile Asp Ala Tyr Leu Thr Thr Ile Cys Gly Asn Leu Leu Tyr
            165                 170                 175

Gln Ala Tyr Pro Lys Leu Arg Pro Phe Phe Val Tyr Gly Gln Phe Lys
            180                 185                 190

Lys Phe Ser Ser Asp Pro Lys Lys Glu Asn Glu Ile Leu Lys Lys Thr
            195                 200                 205

Lys Asn Phe Asp Phe Val Ala Lys Leu Leu Gly Ser Lys Ala Pro Asn
210                 215                 220
```

-continued

Glu Ile Arg Ser Gln Gln Gly Lys Val Leu Phe Glu Lys Asn Lys Ile
225                 230                 235                 240

Arg Leu Gln Leu Asn Lys Ala Tyr Asn Tyr Lys Tyr Met Leu Val Ser
            245                 250                 255

Arg Asp Thr Thr Thr Lys Asn Gln Glu Met Phe Gly Met Thr Ile Tyr
        260                 265                 270

Pro Arg Ala Glu Arg Asp Ile Ala Lys Ser Arg Lys Leu Ile Glu Lys
    275                 280                 285

Arg Lys Gly Phe Ser Thr Asp Ile Tyr Gly Tyr Thr Gly Thr Ala
290                 295                 300

Ala Ala Tyr Met Ala Ile Val Arg Ile Asn Lys Thr Lys Ser Ser Gln
305                 310                 315                 320

Tyr Lys Val Ile Ala Val Pro Met Thr Lys Arg Ala Ile Leu Asn Lys
            325                 330                 335

Ala Glu Lys Glu Gly Asn Tyr Glu Lys Ile Leu Lys Gln Ile Leu Ser
        340                 345                 350

Pro Ser Ile Leu Tyr Asn Asp Lys Gly Lys Arg Lys Ala Gly Val Ile
    355                 360                 365

Ser Phe Asp Ile Ile Lys Gly Lys Val Pro Tyr Asn Gln Val Val Gln
370                 375                 380

Asp Gly Asn Lys Lys Phe Leu Leu Lys Ser Ala Ile Tyr Leu Cys Asn
385                 390                 395                 400

Ala Lys Gln Leu Val Leu Ser Glu Glu Ala Met Arg Val Ile Thr Gly
            405                 410                 415

His Trp Leu Asp Ser Asp Lys Gln Asp Gln Glu Leu Leu Asp Val Tyr
        420                 425                 430

Asp Glu Ile Leu Glu Lys Ile Asp Arg Tyr Leu Pro Leu Phe Asp Ile
    435                 440                 445

Arg Asp Phe Arg Asn Lys Leu His Lys Gly Arg Glu Lys Phe Leu Lys
450                 455                 460

Leu Asn Ala Glu Asp Lys Phe Lys Ala Ile Ile Gln Ile Leu Lys Gly
465                 470                 475                 480

Leu His Asp Asn Ser Asp Thr Gly Glu Leu Lys Asp Ile Gly Ile Thr
            485                 490                 495

Val Pro Phe Gly Gln Leu Gln Asn Asn Ser Gly Ile Thr Leu Ser Ser
        500                 505                 510

Asp Thr Ile Leu Val Tyr Gln Ser Pro Thr Gly Leu Phe Glu Lys Arg
    515                 520                 525

Val Lys Ile Ser Ser Leu
    530

<210> SEQ ID NO 17
<211> LENGTH: 667
<212> TYPE: PRT
<213> ORGANISM: Lactobacillus iners SPIN 2503V10-D
<220> FEATURE:
<221> NAME/KEY: MISC_FEATURE
<223> OTHER INFORMATION: E1NX12_9LACO

<400> SEQUENCE: 17

Met Gln Lys His Asn Tyr Asn Leu Met Gln Leu Met Ser Lys Lys Phe
1               5                   10                  15

Thr Phe Lys Ser Lys Ile Asp Glu Ile Asn Lys Ser Tyr Tyr Gln His
            20                  25                  30

Asp Lys Phe Asn Tyr Lys Ser Met Ile Asp Ser Leu Tyr Val Ser Pro
        35                  40                  45

```
Ala Thr Lys Arg Ile Leu Trp Gln Ser Leu Lys Val Val His Glu Ile
 50                  55                  60

Ser Lys Ile Met Lys His Asp Pro Glu Lys Ile Phe Ile Glu Met Ala
 65                  70                  75                  80

Arg Ser Lys Glu Asp His Pro Lys Arg Lys Leu Ser Arg Lys Ala Asp
                     85                  90                  95

Leu Lys Gln Val Tyr Lys Asp Ser Lys Lys Gln Ile Ile Ser Ile Ile
                100                 105                 110

Gly Lys Asp Lys Tyr Gln Asp Leu Ser Asn Glu Leu Asp Asn Lys Asp
                115                 120                 125

Asp Arg Asp Leu Arg Trp Asp Asn Leu Tyr Leu Tyr Tyr Thr Gln Leu
            130                 135                 140

Gly Arg Ser Met Tyr Ser Leu Lys Pro Ile Asp Ile Ser Glu Leu Met
145                 150                 155                 160

Asn Lys Asn Leu Tyr Asp Gln Asp His Ile Phe Pro Lys Ser Lys Lys
                165                 170                 175

Tyr Asp Asp Ser Ile Glu Asn Arg Val Leu Val Lys Glu Leu Asn
                180                 185                 190

Val Lys Lys Ser Asp Ile Tyr Pro Ile Ser Asp Ala Asn Ile Ile Pro
                195                 200                 205

Gln Lys Ile Lys Gly Gln Val Glu Ser Phe Trp Lys Met Leu Tyr Asp
            210                 215                 220

His Lys Leu Ile Gly Asp Lys Lys Tyr Ala Arg Leu Ile Arg Ser Lys
225                 230                 235                 240

Ala Phe Thr Asp Asp Glu Leu Ala Gly Phe Ile Ala Arg Gln Leu Val
                245                 250                 255

Glu Thr Arg Gln Ala Thr Lys Glu Thr Ala Asp Leu Leu Lys Arg Leu
                260                 265                 270

Cys Pro Lys Ser Arg Ile Val Tyr Ala Lys Ala Gln Asn Ala Ser Ile
                275                 280                 285

Phe Arg Gln Lys Phe Asp Ile Pro Lys Ser Arg Thr Ile Asn Asp Leu
            290                 295                 300

His His Ala Gln Asp Ala Tyr Leu Asn Ile Val Val Gly Asn Ile Phe
305                 310                 315                 320

Asp Thr Lys Phe Thr Gln Asp Pro Arg Asn Phe Ile Lys Asn Thr Lys
                325                 330                 335

Asp Ser Arg Asn Tyr Asn Leu Glu Lys Ile Tyr Asp Tyr Asn Val Glu
                340                 345                 350

Arg Asn Asn Tyr Val Ala Trp Ile Ala Pro Asp Gly Glu Thr Asn Gly
            355                 360                 365

Thr Ile Ala Asn Val Lys Cys Asn Leu Ser Thr Lys Asp Phe Arg Val
            370                 375                 380

Thr Arg Pro Ser Phe Tyr Lys Lys Gly Ala Leu Phe Asn Gln Asn Leu
385                 390                 395                 400

Ser Arg Lys Gly Ser Asn Leu Ala Pro Ile Lys Glu His Ser Pro Lys
                405                 410                 415

Ser Asn Pro Leu Lys Tyr Gly Gly Tyr Ser Gly Lys Asn Asn Ser Phe
                420                 425                 430

Phe Val Val Val Ala Gly Lys Asp Asn Lys Gly Lys Asp Ile Val Lys
            435                 440                 445

Leu Ile Pro Val Asn Thr Leu Ile Tyr Asn Lys Met Leu His Cys Asp
450                 455                 460
```

-continued

```
Tyr Lys Ala Lys Gln Glu Leu Leu Thr Ser Tyr Val Ala Asn Asn Phe
465                 470                 475                 480

Ala Ile Asn Asn Phe Arg Ile Val Lys Asp Asp Ile Lys Met Tyr Ser
            485                 490                 495

Leu Val Lys Ile Asp Gly Ala Tyr Tyr Tyr Leu Val Gly Gly Thr Asp
        500                 505                 510

Glu Arg Ile Glu Val Lys Asn Ala Met Gln Leu Leu Leu Ser Lys Asp
    515                 520                 525

Ser Ile Lys Ala Val Lys Ile Leu Glu Lys Glu Ser Lys Asp Gln Phe
530                 535                 540

Ala Asn Ile Lys Asn Tyr Lys Asp Ile Asp Ile Lys Leu Gly Arg Thr
545                 550                 555                 560

Phe Asn Glu Val Val Ser Lys Tyr Thr Asn Ser Val Phe Gly Lys Ser
            565                 570                 575

Met Leu Ile Ser Asp Lys Tyr Arg Lys Asp Ile Phe Lys Ser Val Glu
        580                 585                 590

Lys Ser Ile Leu Glu Phe Asn His Leu Asp Thr Ile Gly Lys Ala Asp
    595                 600                 605

Asn Leu Leu Lys Phe Val Thr Leu Met Arg Pro Ser Gly Ser Ala His
610                 615                 620

Ser Leu Lys Met Val Gly Leu Ile Glu Arg Ile Arg Lys Ser Asn Val
625                 630                 635                 640

Ile Ser Asn Phe Asn Glu Phe Lys Leu Ile Asn Gln Ser Val Thr Gly
            645                 650                 655

Leu Phe Glu Asn Glu Glu Asp Leu Leu Lys Leu
        660                 665
```

<210> SEQ ID NO 18
<211> LENGTH: 591
<212> TYPE: PRT
<213> ORGANISM: Treponema phagedenis F0421
<220> FEATURE:
<221> NAME/KEY: MISC_FEATURE
<223> OTHER INFORMATION: E7NSW3_TREPH

<400> SEQUENCE: 18

```
Met Ala Arg Gly Lys Glu Ala Glu Lys Gly Arg Thr Ser Ser Arg Tyr
1               5                   10                  15

Ala Ser Ile Lys Ala Leu Tyr Glu Asn Cys Lys Gln Asp Leu Ala Asp
            20                  25                  30

Tyr Asp Ala Val Leu Glu Gln Phe Lys Ser Glu Glu Pro Leu Arg Leu
        35                  40                  45

Arg Ser Asp Lys Leu Tyr Leu Tyr Tyr Thr Gln Leu Gly Arg Cys Met
50                  55                  60

Tyr Thr Gly Arg Val Ile Asp Ile Asp Arg Leu Met Ser Asp Asn Ser
65                  70                  75                  80

Ala Tyr Asp Ile Asp His Ile Tyr Pro Arg Ser Lys Ile Lys Asp Asp
            85                  90                  95

Ser Leu Thr Asn Arg Val Leu Val Lys Asp Ala Asn Gln Asp Lys
        100                 105                 110

Arg Asp Glu Pro Leu Ser Pro Gln Ile Gln Asp Lys Gln Lys Gly Phe
    115                 120                 125

Trp Asp Phe Leu Lys His Asn Asn Phe Ile Ser Ile Glu Lys Tyr Glu
130                 135                 140

Arg Leu Thr Tyr Arg Gly Tyr Phe Thr Glu Glu Met Leu Ser Gly Phe
145                 150                 155                 160
```

```
Ile Ala Arg Gln Leu Val Glu Thr Arg Gln Thr Lys Thr Ala Gly
                165                 170                 175

Gln Ile Leu Glu Gln Leu Tyr Pro Asp Ser Thr Val Val Tyr Cys Lys
            180                 185                 190

Ala Ala Asn Thr Ser Glu Phe Arg Gln Lys Phe Asn Leu Ile Lys Cys
            195                 200                 205

Arg Glu Ile Asn Asp Leu His His Ala His Asp Ala Tyr Leu Asn Ile
        210                 215                 220

Ala Val Gly Asn Val Tyr Tyr Thr Lys Phe Thr Ser Asn Pro Arg Asn
225                 230                 235                 240

Phe Met Lys Leu Lys Glu Pro Tyr Asn Leu Arg Glu Leu Phe Asp Arg
                245                 250                 255

Asp Val Glu Arg Asn Asn Thr Ile Ala Trp Val Lys Asn Lys Thr Ile
            260                 265                 270

Thr Thr Ile Lys Asp Met Leu Lys Arg Asn Thr Pro Leu Tyr Thr Arg
        275                 280                 285

Tyr Ala Tyr Cys Lys Thr Gly Gly Phe Phe Asp Gln Asn Ile Met Lys
        290                 295                 300

Lys Gly Lys Gly Gln Phe Pro Leu Lys Glu Asn Ser Pro Leu Ser Asp
305                 310                 315                 320

Ile Ser Lys Tyr Gly Gly Tyr Asn Lys Val Ser Gly Ala Tyr Phe Ile
                325                 330                 335

Leu Val Gln Lys Lys Glu Lys Asp Ala Val Val Arg Ile Leu Glu Thr
            340                 345                 350

Val Pro Leu Tyr Leu Leu Asn Lys Pro Gly Lys Glu Ser Glu Asn Val
        355                 360                 365

Arg Glu Tyr Leu Ser Thr Ala Leu Gly Thr Lys Asp Phe Lys Ile Leu
        370                 375                 380

Ile Pro Lys Ile Lys Ile Asn Ser Leu Phe Lys Ile Asn Gly Phe Leu
385                 390                 395                 400

Val His Ile Thr Gly Lys Thr Asn Asp Arg Phe Leu Val Arg Ser Ala
                405                 410                 415

Val Gln Phe Phe Cys Asp Asp Asn Leu Thr Leu Phe Phe Lys Arg Ile
            420                 425                 430

Ile Ala Phe Asn Gly Leu Arg Asn Leu Asn Lys Asp Lys Ser Met Thr
        435                 440                 445

Ala Tyr Asp Asp Asn Thr Met Arg Val Tyr Val Arg Gly Asn Leu Phe
450                 455                 460

Lys Asp Lys Asn Gln Leu Phe Asp Lys Asn Lys Phe Asn Glu Ile Val
465                 470                 475                 480

Lys Gly Lys Asn Ile Ser Val Tyr Lys Asp Met Val Lys Arg Tyr Glu
                485                 490                 495

Thr Ser Ile Tyr Lys Phe Arg Pro Asn Thr Ala Val Ile Pro Ile Leu
            500                 505                 510

Lys Ser Gly Glu Asp Lys Phe Ile Asn Leu Pro Ile Glu Glu Gln Phe
        515                 520                 525

Lys Ile Leu Gln Glu Ile Leu Lys Leu Phe Gly Ala Ile Asn Gly Thr
        530                 535                 540

Ala Asn Leu Thr Leu Ile Gly Gly Arg Pro Ser Thr Gly Glu Met Lys
545                 550                 555                 560

Ile Ser Asn Asn Ile Ser Asn Leu Lys Gln Cys Ile Leu Ile His Gln
                565                 570                 575
```

Ser Pro Thr Gly Val Phe Glu Gln Gln Ile Asp Leu Leu Lys Ile
            580                 585                 590

<210> SEQ ID NO 19
<211> LENGTH: 387
<212> TYPE: PRT
<213> ORGANISM: Fusobacterium necrophorum subsp. funduliforme 1_1_36S
<220> FEATURE:
<221> NAME/KEY: MISC_FEATURE
<223> OTHER INFORMATION: H1D477_9FUSO

<400> SEQUENCE: 19

Met Phe Phe Leu Lys Ser Ser Ile Leu Tyr Ser Lys Phe Met Val Leu
1               5                   10                  15

Asn Glu Leu Asn Asn Leu Lys Ile Asp Gly Glu Ala Ile Ser Val Asp
            20                  25                  30

Leu Lys Gln Lys Ile Tyr Leu Asn Leu Phe Gln Lys Tyr Lys Lys Val
        35                  40                  45

Thr Leu Lys Lys Leu Lys Gly Tyr Leu Lys Ser Glu Asn Ile Leu Ile
50                  55                  60

Asp Thr Ser Thr Gln Ile Thr Gly Ile Asp Gly Asp Phe Lys Ser Ser
65                  70                  75                  80

Leu Gly Ser Tyr Leu Asp Phe Tyr Asn Ile Leu Gly Asp Lys Val Lys
                85                  90                  95

Thr Asp Phe Gly Lys Lys Leu Ile Glu Asn Cys Ile Leu Trp Ile Thr
            100                 105                 110

Leu Tyr Thr Gly Glu Lys Lys Leu Leu Lys Asn Lys Ile Ile Ala Asn
        115                 120                 125

Tyr Lys Gly Glu Leu Ser Glu Glu Ile Lys Lys Ile Val Asn Leu
130                 135                 140

Lys Tyr Lys Asp Trp Gly Arg Leu Ser Tyr Ala Phe Leu Glu Glu Ile
145                 150                 155                 160

Gln Ser Ala Ser Leu Glu Thr Gly Glu Leu Arg Asn Ile Ile Gln Met
                165                 170                 175

Met Trp Glu Thr Asn Asn Asn Leu Met Glu Leu Leu Ser Ser Asn Tyr
            180                 185                 190

Gln Phe Leu Ser Glu Ile Glu Lys Arg Asn Ser Val Val Ala Ile Gly
        195                 200                 205

Lys Glu Phe Asn Tyr Glu Thr Ile Leu Gly Asp Ser Tyr Ala Ser Pro
210                 215                 220

Ser Val Lys Arg Met Ile Trp Gln Ser Leu Ser Val Val Asp Glu Ile
225                 230                 235                 240

Lys Lys Ile Met Lys Lys Ala Pro Lys Lys Ile Phe Ile Glu Met Ala
                245                 250                 255

Arg Gln Glu Asp Met Lys Lys Glu Arg Lys Glu Ser Arg Lys Ser Thr
            260                 265                 270

Phe Leu Thr Leu Tyr Lys Ser Ile Lys Glu Glu Gly Arg Asp Trp Ile
        275                 280                 285

Lys Glu Ile Glu Asn Trp Ser Asp Ser Glu Phe Arg Ser Lys Lys Leu
290                 295                 300

Tyr Leu Tyr Tyr Thr Gln Met Gly Lys Cys Met Tyr Thr Gly Glu Lys
305                 310                 315                 320

Ile Ser Leu Asp Gln Leu Phe Asn Lys Asn Ile Tyr Asp Ile Asp His
                325                 330                 335

Ile Tyr Pro Arg Ser Lys Ile Lys Asp Asp Ser Ile Glu Asn Ile Val
            340                 345                 350

Leu Val Lys Arg Asn Ile Asn Ala Lys Lys Thr Asp Glu Tyr Pro Leu
            355                 360                 365

Glu Arg Asn Ile Gln Gln Lys Gln His Asp Phe Trp Lys Met Leu His
    370                 375                 380

Ser Lys Asn
385

<210> SEQ ID NO 20
<211> LENGTH: 544
<212> TYPE: PRT
<213> ORGANISM: Lactobacillus crispatus JV-V01
<220> FEATURE:
<221> NAME/KEY: MISC_FEATURE
<223> OTHER INFORMATION: C2KFJ4_9LACO

<400> SEQUENCE: 20

Lys Tyr Tyr Leu Tyr Phe Met Gln Leu Gly Arg Asp Ala Tyr Thr Gly
1               5                   10                  15

Lys Pro Ile Asn Ile Asp Glu Val Ser Gln Tyr Tyr Asp Ile Asp His
            20                  25                  30

Ile Leu Pro Gln Ser Phe Ile Lys Asp Asp Ser Leu Asn Asn Arg Val
        35                  40                  45

Leu Val Ala Lys Pro Ile Asn Asn Gly Lys Ser Asp Gly Val Pro Leu
    50                  55                  60

Lys Leu Phe Gly Asp Asn Leu Ala Thr Gly Leu Gly Ile Thr Val Lys
65                  70                  75                  80

Gln Met Trp Asn Asn Trp Ala Asp Lys Gly Leu Ile Asn Lys Ala Lys
                85                  90                  95

Gln Asn Asn Leu Phe Leu Asp Pro Glu Asn Ile Asn Lys His Gln Ala
            100                 105                 110

Ser Gly Phe Ile Arg Lys Gln Leu Val Glu Thr Ser Gln Ile Ile Lys
        115                 120                 125

Leu Ala Thr Thr Ile Leu Gln Ala Glu Tyr Pro Lys Thr Lys Ile Ile
    130                 135                 140

Val Val Lys Ala Ser Ser Asn His Tyr Leu Arg Asn Glu Phe Asp Leu
145                 150                 155                 160

Tyr Lys Ser Arg Glu Val Asn Asp Tyr His His Ala Ile Asp Ala Tyr
                165                 170                 175

Leu Thr Thr Ile Cys Gly Asn Leu Leu Tyr Gln Ala Tyr Pro Lys Leu
            180                 185                 190

Arg Pro Phe Phe Val Tyr Gly Gln Phe Lys Lys Phe Ser Ser Asp Pro
        195                 200                 205

Lys Lys Glu Asn Glu Ile Leu Lys Lys Thr Lys Asn Phe Asp Phe Val
    210                 215                 220

Ala Lys Leu Leu Gly Ser Lys Ala Pro Asn Glu Ile Arg Ser Gln Gln
225                 230                 235                 240

Gly Lys Val Leu Phe Glu Lys Asn Lys Ile Arg Leu Gln Leu Asn Lys
                245                 250                 255

Ala Tyr Asn Tyr Lys Tyr Met Leu Val Ser Arg Asp Thr Thr Thr Lys
            260                 265                 270

Asn Gln Glu Met Phe Gly Met Thr Ile Tyr Pro Arg Ala Glu Arg Asp
        275                 280                 285

Ile Ala Lys Ser Arg Lys Leu Ile Glu Lys Arg Lys Gly Phe Ser Thr
    290                 295                 300

Asp Ile Tyr Gly Gly Tyr Thr Gly Thr Ala Ala Ala Tyr Met Ala Ile

```
                305                 310                 315                 320
Val Arg Ile Asn Lys Thr Lys Ser Ser Gln Tyr Lys Val Ile Ala Val
                    325                 330                 335

Pro Met Thr Lys Arg Ala Ile Leu Asn Lys Ala Glu Lys Glu Gly Asn
                    340                 345                 350

Tyr Glu Lys Ile Leu Lys Gln Ile Leu Ser Pro Ser Ile Leu Tyr Asn
                    355                 360                 365

Asp Lys Gly Lys Arg Lys Ala Gly Val Ile Ser Phe Asp Ile Ile Lys
                    370                 375                 380

Gly Lys Val Pro Tyr Asn Gln Val Val Gln Asp Gly Asn Lys Lys Phe
385                 390                 395                 400

Leu Leu Lys Ser Ala Ile Tyr Leu Cys Asn Ala Lys Gln Leu Val Leu
                    405                 410                 415

Ser Glu Glu Ala Met Arg Val Ile Thr Gly His Trp Leu Asp Ser Asp
                    420                 425                 430

Lys Gln Asp Gln Glu Leu Leu Asp Val Tyr Asp Glu Ile Leu Glu Lys
                    435                 440                 445

Ile Asp Arg Tyr Leu Pro Leu Phe Asp Ile Arg Asp Phe Arg Asn Lys
                    450                 455                 460

Leu His Lys Gly Arg Glu Lys Phe Leu Lys Leu Asn Ala Glu Asp Lys
465                 470                 475                 480

Phe Lys Ala Ile Ile Gln Ile Leu Lys Gly Leu His Asp Asn Ser Asp
                    485                 490                 495

Thr Gly Glu Leu Lys Asp Ile Gly Ile Thr Val Pro Phe Gly Gln Leu
                    500                 505                 510

Gln Asn Asn Ser Gly Ile Thr Leu Ser Ser Asp Thr Ile Leu Val Tyr
                    515                 520                 525

Gln Ser Pro Thr Gly Leu Phe Glu Lys Arg Val Lys Ile Ser Ser Leu
                    530                 535                 540

<210> SEQ ID NO 21
<211> LENGTH: 206
<212> TYPE: PRT
<213> ORGANISM: Lactobacillus crispatus FB077-07
<220> FEATURE:
<221> NAME/KEY: MISC_FEATURE
<223> OTHER INFORMATION: K1MRU9_9LACO

<400> SEQUENCE: 21

Met Gln Leu Gly Arg Asp Ala Tyr Thr Gly Lys Pro Ile Asn Ile Asp
1               5                   10                  15

Glu Val Ser Gln Tyr Tyr Asp Ile Asp His Ile Leu Pro Gln Ser Phe
                    20                  25                  30

Ile Lys Asp Asp Ser Leu Asn Asn Arg Val Leu Val Ala Lys Pro Ile
                    35                  40                  45

Asn Asn Gly Lys Ser Asp Gly Val Pro Leu Lys Leu Phe Gly Asp Asn
                    50                  55                  60

Leu Ala Thr Gly Leu Gly Ile Thr Val Lys Gln Met Trp Asn Asn Trp
65                  70                  75                  80

Ala Asp Lys Gly Leu Ile Asn Lys Ala Lys Gln Asn Asn Leu Phe Leu
                    85                  90                  95

Asp Pro Glu Asn Ile Asn Lys His Gln Ala Ser Gly Phe Ile Arg Lys
                    100                 105                 110

Gln Leu Val Glu Thr Ser Gln Ile Ile Lys Leu Ala Thr Thr Ile Leu
                    115                 120                 125
```

Gln Ala Glu Tyr Pro Lys Thr Lys Ile Ile Val Val Lys Ala Ser Ser
130                 135                 140

Asn His Tyr Leu Arg Asn Glu Phe Asp Leu Tyr Lys Ser Arg Glu Val
145                 150                 155                 160

Asn Asp Tyr His His Ala Ile Asp Ala Tyr Leu Thr Thr Ile Cys Gly
                165                 170                 175

Asn Leu Leu Tyr Gln Ala Tyr Pro Lys Leu Arg Pro Phe Phe Val Tyr
            180                 185                 190

Gly Gln Phe Lys Lys Phe Ser Ser Asp Pro Lys Lys Arg Lys
        195                 200                 205

<210> SEQ ID NO 22
<211> LENGTH: 874
<212> TYPE: PRT
<213> ORGANISM: Listeria seeligeri FSL N1-067
<220> FEATURE:
<221> NAME/KEY: MISC_FEATURE
<223> OTHER INFORMATION: E3ZTQ9_LISSE

<400> SEQUENCE: 22

Leu Ala Asn Gly Gln Ser Glu Phe Ser Trp Leu Thr Arg Lys Ala Asp
1               5                   10                  15

Gly Glu Ile Arg Pro Trp Asn Ile Glu Glu Lys Val Asp Phe Gly Lys
            20                  25                  30

Ser Ala Ile Asp Phe Ile Glu Lys Met Thr Asn Lys Asp Thr Tyr Leu
        35                  40                  45

Pro Lys Glu Asn Val Leu Pro Lys His Ser Met Cys Tyr Gln Lys Tyr
50                  55                  60

Met Val Tyr Asn Glu Leu Thr Lys Ile Arg Tyr Thr Asp Asp Gln Gly
65                  70                  75                  80

Lys Thr His Tyr Phe Ser Gly Gln Glu Lys Gln Gln Ile Phe Asn Asp
                85                  90                  95

Leu Phe Lys Gln Lys Arg Lys Val Lys Lys Asp Leu Glu Leu Phe
            100                 105                 110

Leu Tyr Asn Met Asn His Val Glu Ser Pro Thr Val Glu Gly Val Glu
        115                 120                 125

Asp Ala Phe Asn Ser Ser Phe Thr Thr Tyr His Asp Leu Gln Lys Val
130                 135                 140

Gly Val Pro Gln Glu Ile Leu Asp Asp Pro Leu Asn Thr Glu Met Leu
145                 150                 155                 160

Glu Glu Ile Ile Lys Ile Leu Thr Val Phe Glu Asp Lys Arg Met Ile
                165                 170                 175

Asn Glu Arg Leu Gln Glu Phe Ser Asn Val Leu Asp Glu Ala Val Leu
            180                 185                 190

Lys Lys Leu Glu Arg Arg His Tyr Thr Gly Trp Gly Arg Leu Ser Ala
        195                 200                 205

Lys Leu Leu Ile Gly Ile Arg Asp Lys Glu Ser His Leu Thr Ile Leu
    210                 215                 220

Asp Tyr Leu Met Asn Asp Lys His Asn Arg Asn Leu Met Gln Leu
225                 230                 235                 240

Ile Asn Asp Ser Asn Leu Ser Phe Lys Ser Ile Ile Glu Lys Glu Gln
                245                 250                 255

Val Ser Thr Ala Asp Lys Asp Ile Gln Ser Ile Val Ala Asp Leu Ala
            260                 265                 270

Gly Ser Pro Ala Ile Lys Lys Gly Ile Leu Gln Ser Leu Lys Ile Val
        275                 280                 285

```
Asp Glu Leu Val Gly Ile Met Gly Tyr Pro Pro Gln Thr Ile Val Val
    290                 295                 300

Glu Met Ala Arg Glu Asn Gln Thr Thr Gly Lys Gly Lys Asn Asn Ser
305                 310                 315                 320

Lys Pro Arg Phe Thr Ser Leu Glu Lys Ala Ile Lys Glu Leu Gly Ser
                325                 330                 335

Gln Ile Leu Lys Glu His Pro Thr Asp Asn Gln Gly Leu Lys Asn Asp
                340                 345                 350

Arg Leu Tyr Leu Tyr Tyr Leu Gln Asn Gly Lys Asp Met Tyr Thr Gly
                355                 360                 365

Gln Glu Leu Asp Ile His Asn Leu Ser Asn Tyr Asp Ile Asp His Val
    370                 375                 380

Val Pro Gln Ser Phe Ile Thr Asp Asn Ser Ile Asp Asn Arg Val Leu
385                 390                 395                 400

Ala Ser Ser Ala Ala Asn Arg Glu Lys Gly Asp Asn Val Pro Ser Leu
                405                 410                 415

Glu Val Val Arg Lys Arg Lys Val Tyr Trp Glu Lys Leu Tyr Gln Ala
                420                 425                 430

Lys Leu Met Ser Lys Arg Lys Phe Asp Tyr Leu Thr Lys Ala Glu Arg
                435                 440                 445

Gly Gly Leu Thr Glu Ala Asp Lys Ala Arg Phe Ile His Arg Gln Leu
    450                 455                 460

Val Glu Thr Arg Gln Ile Thr Lys Asn Val Ala Asn Ile Leu His Gln
465                 470                 475                 480

Arg Phe Asn Cys Lys Lys Asp Glu Ser Gly Asn Val Ile Glu Gln Val
                485                 490                 495

Arg Ile Val Thr Leu Lys Ala Ala Leu Val Ser Gln Phe Arg Lys Gln
                500                 505                 510

Phe Gln Leu Tyr Lys Val Arg Glu Val Asn Asp Tyr His His Ala His
                515                 520                 525

Asp Ala Tyr Leu Asn Cys Val Val Ala Asn Thr Leu Leu Lys Val Tyr
    530                 535                 540

Pro Gln Leu Glu Pro Glu Phe Val Tyr Gly Asp Tyr His Gln Phe Asp
545                 550                 555                 560

Trp Phe Lys Ala Asn Lys Ala Thr Ala Lys Lys Gln Phe Tyr Thr Asn
                565                 570                 575

Ile Met Leu Phe Phe Ala Lys Lys Asp Arg Ile Ile Asp Glu Asn Gly
                580                 585                 590

Glu Ile Leu Trp Asp Lys Lys Tyr Leu Asp Thr Ile Lys Lys Val Leu
                595                 600                 605

Asn Tyr Arg Gln Met Asn Ile Val Lys Lys Thr Glu Ile Gln Lys Gly
    610                 615                 620

Glu Phe Ser Asn Ala Thr Ala Asn Pro Lys Gly Asn Ser Ser Lys Leu
625                 630                 635                 640

Ile Pro Arg Lys Ala Asp Trp Asp Pro Ile Lys Tyr Gly Gly Phe Asp
                645                 650                 655

Gly Ser Asn Met Ala Tyr Ala Ile Val Ile Glu His Glu Lys Arg Lys
                660                 665                 670

Lys Lys Thr Val Ile Lys Lys Glu Leu Ile Gln Ile Asn Ile Met Glu
                675                 680                 685

Arg Thr Ala Phe Glu Lys Asp Gln Lys Glu Phe Leu Glu Gly Lys Gly
    690                 695                 700
```

Tyr Arg Asn Pro Lys Val Ile Thr Lys Ile Pro Lys Tyr Thr Leu Tyr
705                 710                 715                 720

Glu Cys Glu Asn Gly Arg Arg Met Leu Gly Ser Ala Asn Glu Ala
            725                 730                 735

Gln Lys Gly Asn Gln Met Val Leu Pro Asn His Leu Met Thr Leu Leu
            740                 745                 750

Tyr His Ala Lys Asn Cys Glu Ala Ser Asp Gly Lys Ser Leu Ala Tyr
            755                 760                 765

Ile Glu Ser His Arg Glu Met Phe Ala Glu Leu Leu Asp Ser Ile Ser
            770                 775                 780

Glu Phe Ala Ser Arg Tyr Thr Leu Ala Asp Ala Asn Leu Glu Lys Ile
785                 790                 795                 800

Asn Thr Ile Phe Glu Gln Asn Lys Ser Gly Asp Val Lys Val Ile Ala
            805                 810                 815

Gln Ser Phe Val Asn Leu Leu Glu Phe Asn Ala Met Gly Ala Pro Ala
            820                 825                 830

Ser Phe Lys Tyr Phe Glu Thr Asn Ile Glu Arg Lys Arg Tyr Asn Asn
            835                 840                 845

Leu Lys Glu Leu Leu Asn Ala Thr Ile Ile Tyr Gln Ser Ile Thr Gly
            850                 855                 860

Leu Tyr Glu Ala Arg Lys Arg Leu Asp Asp
865                 870

<210> SEQ ID NO 23
<211> LENGTH: 182
<212> TYPE: PRT
<213> ORGANISM: artificial sequence
<220> FEATURE:
<223> OTHER INFORMATION: HNH domain Delta 981 of S. pyogenes Cas9

<400> SEQUENCE: 23

Pro Val Glu Asn Thr Gln Leu Gln Asn Glu Lys Leu Tyr Leu Tyr Tyr
1               5                   10                  15

Leu Gln Asn Gly Arg Asp Met Tyr Val Asp Gln Glu Leu Asp Ile Asn
            20                  25                  30

Arg Leu Ser Asp Tyr Asp Val Asp His Ile Val Pro Gln Ser Phe Leu
        35                  40                  45

Lys Asp Asp Ser Ile Asp Asn Lys Val Leu Thr Arg Ser Asp Lys Asn
50                  55                  60

Arg Gly Lys Ser Asp Asn Val Pro Ser Glu Glu Val Val Lys Lys Met
65                  70                  75                  80

Lys Asn Tyr Trp Arg Gln Leu Leu Asn Ala Lys Leu Ile Thr Gln Arg
                85                  90                  95

Lys Phe Asp Asn Leu Thr Lys Ala Glu Arg Gly Gly Leu Ser Glu Leu
            100                 105                 110

Asp Lys Ala Gly Phe Ile Lys Arg Gln Leu Val Glu Thr Arg Gln Ile
        115                 120                 125

Thr Lys His Val Ala Gln Ile Leu Asp Ser Arg Met Asn Thr Lys Tyr
    130                 135                 140

Asp Glu Asn Asp Lys Leu Ile Arg Glu Val Lys Val Ile Thr Leu Lys
145                 150                 155                 160

Ser Lys Leu Val Ser Asp Phe Arg Lys Asp Phe Gln Phe Tyr Lys Val
                165                 170                 175

Arg Glu Ile Asn Asn Tyr
            180

```
<210> SEQ ID NO 24
<211> LENGTH: 158
<212> TYPE: PRT
<213> ORGANISM: artificial sequence
<220> FEATURE:
<223> OTHER INFORMATION: HNH domain Delta 957 of S. pyogenes Cas9

<400> SEQUENCE: 24

Pro Val Glu Asn Thr Gln Leu Gln Asn Glu Lys Leu Tyr Leu Tyr Tyr
1               5                   10                  15

Leu Gln Asn Gly Arg Asp Met Tyr Val Asp Gln Glu Leu Asp Ile Asn
            20                  25                  30

Arg Leu Ser Asp Tyr Asp Val Asp His Ile Val Pro Gln Ser Phe Leu
        35                  40                  45

Lys Asp Asp Ser Ile Asp Asn Lys Val Leu Thr Arg Ser Asp Lys Asn
    50                  55                  60

Arg Gly Lys Ser Asp Asn Val Pro Ser Glu Glu Val Val Lys Lys Met
65                  70                  75                  80

Lys Asn Tyr Trp Arg Gln Leu Leu Asn Ala Lys Leu Ile Thr Gln Arg
                85                  90                  95

Lys Phe Asp Asn Leu Thr Lys Ala Glu Arg Gly Gly Leu Ser Glu Leu
            100                 105                 110

Asp Lys Ala Gly Phe Ile Lys Arg Gln Leu Val Glu Thr Arg Gln Ile
        115                 120                 125

Thr Lys His Val Ala Gln Ile Leu Asp Ser Arg Met Asn Thr Lys Tyr
    130                 135                 140

Asp Glu Asn Asp Lys Leu Ile Arg Glu Val Lys Val Ile Thr
145                 150                 155

<210> SEQ ID NO 25
<211> LENGTH: 144
<212> TYPE: PRT
<213> ORGANISM: artificial sequence
<220> FEATURE:
<223> OTHER INFORMATION: HNH domain Delta 943 of S. pyogenes Cas9

<400> SEQUENCE: 25

Pro Val Glu Asn Thr Gln Leu Gln Asn Glu Lys Leu Tyr Leu Tyr Tyr
1               5                   10                  15

Leu Gln Asn Gly Arg Asp Met Tyr Val Asp Gln Glu Leu Asp Ile Asn
            20                  25                  30

Arg Leu Ser Asp Tyr Asp Val Asp His Ile Val Pro Gln Ser Phe Leu
        35                  40                  45

Lys Asp Asp Ser Ile Asp Asn Lys Val Leu Thr Arg Ser Asp Lys Asn
    50                  55                  60

Arg Gly Lys Ser Asp Asn Val Pro Ser Glu Glu Val Val Lys Lys Met
65                  70                  75                  80

Lys Asn Tyr Trp Arg Gln Leu Leu Asn Ala Lys Leu Ile Thr Gln Arg
                85                  90                  95

Lys Phe Asp Asn Leu Thr Lys Ala Glu Arg Gly Gly Leu Ser Glu Leu
            100                 105                 110

Asp Lys Ala Gly Phe Ile Lys Arg Gln Leu Val Glu Thr Arg Gln Ile
        115                 120                 125

Thr Lys His Val Ala Gln Ile Leu Asp Ser Arg Met Asn Thr Lys Tyr
    130                 135                 140

<210> SEQ ID NO 26
```

```
<211> LENGTH: 765
<212> TYPE: PRT
<213> ORGANISM: Butyrivibrio fibrisolvens
<220> FEATURE:
<221> NAME/KEY: MISC_FEATURE
<223> OTHER INFORMATION: D4IZM9_BUTFI

<400> SEQUENCE: 26
```

| | | | | | | | | | | | | | | |
|---|---|---|---|---|---|---|---|---|---|---|---|---|---|---|
| Met | Gly | Ile | Thr | Ile | Gly | Leu | Asp | Leu | Gly | Val | Ala | Ser | Val | Gly | Trp |
| 1 | | | | 5 | | | | | 10 | | | | | 15 | |
| Ala | Val | Val | Asn | Asp | Asp | Tyr | Glu | Ile | Leu | Ser | Cys | Ser | Asn | Ile | |
| | | | 20 | | | | | 25 | | | | | 30 | | |
| Phe | Pro | Ser | Ala | Asp | Ala | Ser | Lys | Asn | Ser | Glu | Arg | Arg | Gly | Phe | Arg |
| | | 35 | | | | | 40 | | | | | 45 | | | |
| Gln | Gly | Arg | Arg | Leu | Thr | Arg | Arg | Lys | Asn | Arg | Ile | His | Asp | Phe | |
| 50 | | | | | 55 | | | | | 60 | | | | | |
| Gln | Lys | Leu | Trp | Glu | Asp | Lys | Gly | Phe | Val | Ile | Pro | Ser | Gln | Gly | Thr |
| 65 | | | | 70 | | | | | 75 | | | | | 80 | |
| Glu | Asp | Val | Leu | Ala | Ile | Lys | Ile | Lys | Gly | Leu | Ser | Glu | Lys | Leu | Ser |
| | | | | 85 | | | | | 90 | | | | | 95 | |
| Val | Asp | Glu | Val | Tyr | Trp | Val | Leu | Leu | Asn | Ser | Leu | Lys | His | Arg | Gly |
| | | | 100 | | | | | 105 | | | | | 110 | | |
| Ile | Ser | Tyr | Leu | Asp | Asp | Ala | Asp | Ser | Gly | Asp | Asn | Ser | Ser | Asp | Tyr |
| | | 115 | | | | | 120 | | | | | 125 | | | |
| Ala | Lys | Ser | Ile | Ser | Arg | Asn | Glu | Glu | Leu | Lys | Glu | Lys | Leu | Pro | |
| 130 | | | | | 135 | | | | | 140 | | | | | |
| Cys | Glu | Ile | Gln | Trp | Glu | Arg | Leu | Gln | Lys | Tyr | Gly | Ala | Tyr | Arg | Gly |
| 145 | | | | 150 | | | | | 155 | | | | | 160 | |
| Asn | Ile | Ser | Ile | Val | Glu | Asp | Gly | Glu | Pro | Ile | Thr | Leu | Arg | Asn | Val |
| | | | | 165 | | | | | 170 | | | | | 175 | |
| Phe | Thr | Thr | Ser | Ala | Tyr | Lys | Lys | Glu | Val | Glu | Gln | Phe | Ile | Asp | Thr |
| | | | 180 | | | | | 185 | | | | | 190 | | |
| Gln | Ala | Lys | Tyr | Asn | Ala | Gln | Tyr | Ser | Gly | Asp | Phe | Lys | Ala | Asp | Tyr |
| | | 195 | | | | | 200 | | | | | 205 | | | |
| Leu | Glu | Ile | Phe | Asn | Arg | Lys | Arg | Glu | Tyr | Tyr | Glu | Gly | Pro | Gly | Asn |
| 210 | | | | | 215 | | | | | 220 | | | | | |
| Glu | Leu | Ser | Arg | Thr | Asp | Tyr | Gly | Lys | Tyr | Thr | Thr | Glu | Ile | Asn | Ala |
| 225 | | | | 230 | | | | | 235 | | | | | 240 | |
| Asp | Gly | Glu | Tyr | Ile | Thr | Val | Asp | Asn | Ile | Phe | Asp | Lys | Leu | Val | Gly |
| | | | | 245 | | | | | 250 | | | | | 255 | |
| Lys | Cys | Ser | Val | Asn | Pro | Asp | Glu | Arg | Arg | Ala | Ala | Gly | Ala | Ser | Tyr |
| | | | 260 | | | | | 265 | | | | | 270 | | |
| Thr | Ala | Gln | Glu | Phe | Asn | Val | Leu | Asn | Asp | Leu | Asn | Asn | Leu | Thr | Ile |
| | | 275 | | | | | 280 | | | | | 285 | | | |
| Ser | Ser | Glu | Ser | Ser | Phe | Ile | Glu | Asp | Gly | Lys | Leu | Thr | Glu | Asp | Ala |
| | 290 | | | | | 295 | | | | | 300 | | | | |
| Lys | Arg | Lys | Ile | Ile | Glu | Thr | Ile | Lys | Asn | Ala | Lys | Thr | Val | Asn | Val |
| 305 | | | | | 310 | | | | | 315 | | | | | 320 |
| Lys | Lys | Ile | Ile | Cys | Asp | Val | Ile | Gly | Asp | Lys | Lys | Cys | Gln | Ile | Ser |
| | | | | 325 | | | | | 330 | | | | | 335 | |
| Gly | Ala | Arg | Ile | Asp | Lys | Asn | Glu | Lys | Glu | Ile | Phe | His | Ser | Phe | Glu |
| | | | 340 | | | | | 345 | | | | | 350 | | |
| Ala | Tyr | Asn | Lys | Met | Arg | Arg | Ala | Leu | Glu | Glu | Ile | Gly | Phe | Asp | Ile |
| | | 355 | | | | | 360 | | | | | 365 | | | |
| Ser | Ser | Leu | Ser | Arg | Glu | Asn | Leu | Asp | Leu | Ile | Gly | Asp | Ile | Leu | Thr |

```
                370              375             380
Leu Asn Thr Asp Arg Glu Ser Ile Leu Asn Ala Phe Asn Arg Lys Gly
385                 390                 395                 400

Ile Glu Leu Ala Asp Glu Ala Lys Asp Ile Leu Val Lys Val Arg Lys
                405                 410                 415

Thr Asn Gly Ser Leu Phe Asn Lys Trp Gln Ser Phe Gly Leu Ser Ile
            420                 425                 430

Met Asn Glu Leu Ile Pro Glu Leu Tyr Ala Gln Pro Lys Asn Gln Met
            435                 440                 445

Glu Leu Leu Thr Ala Met Gly Val Phe Lys Ser Arg Gly Asp Arg Phe
450                 455                 460

Leu Glu Cys Lys Glu Ile Pro Gly Asp Leu Ile Val Asp Asp Ile Tyr
465                 470                 475                 480

Asn Pro Val Val Ser Lys Thr Val Arg Ile Thr Val Arg Ile Leu Asn
                485                 490                 495

Ala Leu Ile Lys Lys Tyr Gly Tyr Pro Asp Arg Val Val Ile Glu Met
            500                 505                 510

Pro Arg Asp Lys Asn Ser Asp Glu Glu Gln Gln Arg Leu Lys Lys Glu
            515                 520                 525

Gln Arg Asp Asn Glu Asn Glu Ile Lys Asp Ile Lys Ala Arg Val Lys
            530                 535                 540

Thr Glu Tyr Gly Arg Glu Ile Thr Glu Glu Asp Phe Arg Gln His Ser
545                 550                 555                 560

Lys Leu Ser Leu Lys Leu Lys Leu Trp Asn Glu Gln Gln Gly Ile Cys
                565                 570                 575

Pro Tyr Ser Gly Lys Ser Ile Lys Ile Asp Asp Leu Leu Asp Asn Pro
            580                 585                 590

Asn Leu Phe Glu Val Asp His Ile Ile Pro Leu Ser Ile Ser Phe Asp
            595                 600                 605

Asp Ser Arg Asn Asn Lys Val Leu Val Tyr Ser Ser Glu Asn Gln Asp
610                 615                 620

Lys Gly Asn Arg Thr Pro Leu Ala Tyr Leu Ala Ser Val Asn Arg Gln
625                 630                 635                 640

Trp Asp Ile His Ser Phe Met Asp Tyr Val Leu Lys Thr Tyr Ala Gly
                645                 650                 655

Ala Gln Lys Arg Lys Arg Asp Asn Leu Leu Asn Glu Gln Asp Ile
            660                 665                 670

Thr Lys Val Glu Val Leu Gln Gly Phe Val Asn Arg Asn Ile Asn Asp
            675                 680                 685

Thr Arg Tyr Ala Ser Lys Val Val Leu Asn Ser Leu Gln Glu Tyr Phe
690                 695                 700

Ser Ser Lys Glu Cys Ser Thr Lys Val Lys Val Ile Arg Gly Ser Phe
705                 710                 715                 720

Thr His Gln Met Arg Val Asn Leu Lys Leu Lys Lys Thr Val Met Asn
                725                 730                 735

His Met Phe Ile Met Gln Leu Met Gln Cys Leu Leu Leu Phe His Arg
            740                 745                 750

Trp Asp Met Thr Leu Ile Met Asn Leu Gln Ile Ser Ile
            755                 760                 765

<210> SEQ ID NO 27
<211> LENGTH: 1056
<212> TYPE: PRT
<213> ORGANISM: Pasteurella multocida (strain Pm70)
```

-continued

```
<220> FEATURE:
<221> NAME/KEY: MISC_FEATURE
<223> OTHER INFORMATION: Q9CLT2_PASMU

<400> SEQUENCE: 27

Met Gln Thr Thr Asn Leu Ser Tyr Ile Leu Gly Leu Asp Leu Gly Ile
1               5                   10                  15

Ala Ser Val Gly Trp Ala Val Val Glu Ile Asn Glu Asn Glu Asp Pro
            20                  25                  30

Ile Gly Leu Ile Asp Val Gly Val Arg Ile Phe Glu Arg Ala Glu Val
        35                  40                  45

Pro Lys Thr Gly Glu Ser Leu Ala Leu Ser Arg Arg Leu Ala Arg Ser
    50                  55                  60

Thr Arg Arg Leu Ile Arg Arg Ala His Arg Leu Leu Leu Ala Lys
65                  70                  75                  80

Arg Phe Leu Lys Arg Glu Gly Ile Leu Ser Thr Ile Asp Leu Glu Lys
                85                  90                  95

Gly Leu Pro Asn Gln Ala Trp Glu Leu Arg Val Ala Gly Leu Glu Arg
            100                 105                 110

Arg Leu Ser Ala Ile Glu Trp Gly Ala Val Leu Leu His Leu Ile Lys
        115                 120                 125

His Arg Gly Tyr Leu Ser Lys Arg Lys Asn Glu Ser Gln Thr Asn Asn
130                 135                 140

Lys Glu Leu Gly Ala Leu Leu Ser Gly Val Ala Gln Asn His Gln Leu
145                 150                 155                 160

Leu Gln Ser Asp Asp Tyr Arg Thr Pro Ala Glu Leu Ala Leu Lys Lys
                165                 170                 175

Phe Ala Lys Glu Glu Gly His Ile Arg Asn Gln Arg Gly Ala Tyr Thr
            180                 185                 190

His Thr Phe Asn Arg Leu Asp Leu Leu Ala Glu Leu Asn Leu Leu Phe
        195                 200                 205

Ala Gln Gln His Gln Phe Gly Asn Pro His Cys Lys Glu His Ile Gln
    210                 215                 220

Gln Tyr Met Thr Glu Leu Leu Met Trp Gln Lys Pro Ala Leu Ser Gly
225                 230                 235                 240

Glu Ala Ile Leu Lys Met Leu Gly Lys Cys Thr His Glu Lys Asn Glu
                245                 250                 255

Phe Lys Ala Ala Lys His Thr Tyr Ser Ala Glu Arg Phe Val Trp Leu
            260                 265                 270

Thr Lys Leu Asn Asn Leu Arg Ile Leu Glu Asp Gly Ala Glu Arg Ala
        275                 280                 285

Leu Asn Glu Glu Glu Arg Gln Leu Leu Ile Asn His Pro Tyr Glu Lys
    290                 295                 300

Ser Lys Leu Thr Tyr Ala Gln Val Arg Lys Leu Leu Gly Leu Ser Glu
305                 310                 315                 320

Gln Ala Ile Phe Lys His Leu Arg Tyr Ser Lys Glu Asn Ala Glu Ser
                325                 330                 335

Ala Thr Phe Met Glu Leu Lys Ala Trp His Ala Ile Arg Lys Ala Leu
            340                 345                 350

Glu Asn Gln Gly Leu Lys Asp Thr Trp Gln Asp Leu Ala Lys Lys Pro
        355                 360                 365

Asp Leu Leu Asp Glu Ile Gly Thr Ala Phe Ser Leu Tyr Lys Thr Asp
    370                 375                 380

Glu Asp Ile Gln Gln Tyr Leu Thr Asn Lys Val Pro Asn Ser Val Ile
```

-continued

```
            385                 390                 395                 400
        Asn Ala Leu Leu Val Ser Leu Asn Phe Asp Lys Phe Ile Glu Leu Ser
                        405                 410                 415
        Leu Lys Ser Leu Arg Lys Ile Leu Pro Leu Met Glu Gln Gly Lys Arg
                        420                 425                 430
        Tyr Asp Gln Ala Cys Arg Glu Ile Tyr Gly His His Tyr Gly Glu Ala
                        435                 440                 445
        Asn Gln Lys Thr Ser Gln Leu Leu Pro Ala Ile Pro Ala Gln Glu Ile
                        450                 455                 460
        Arg Asn Pro Val Val Leu Arg Thr Leu Ser Gln Ala Arg Lys Val Ile
        465                 470                 475                 480
        Asn Ala Ile Ile Arg Gln Tyr Gly Ser Pro Ala Arg Val His Ile Glu
                        485                 490                 495
        Thr Gly Arg Glu Leu Gly Lys Ser Phe Lys Glu Arg Glu Ile Gln
                        500                 505                 510
        Lys Gln Gln Glu Asp Asn Arg Thr Lys Arg Glu Ser Ala Val Gln Lys
                        515                 520                 525
        Phe Lys Glu Leu Phe Ser Asp Phe Ser Ser Glu Pro Lys Ser Lys Asp
                        530                 535                 540
        Ile Leu Lys Phe Arg Leu Tyr Glu Gln Gln His Gly Lys Cys Leu Tyr
        545                 550                 555                 560
        Ser Gly Lys Glu Ile Asn Ile His Arg Leu Asn Glu Lys Gly Tyr Val
                        565                 570                 575
        Glu Ile Asp His Ala Leu Pro Phe Ser Arg Thr Trp Asp Asp Ser Phe
                        580                 585                 590
        Asn Asn Lys Val Leu Val Leu Ala Ser Glu Asn Gln Asn Lys Gly Asn
                        595                 600                 605
        Gln Thr Pro Tyr Glu Trp Leu Gln Gly Lys Ile Asn Ser Glu Arg Trp
                        610                 615                 620
        Lys Asn Phe Val Ala Leu Val Leu Gly Ser Gln Cys Ser Ala Ala Lys
        625                 630                 635                 640
        Lys Gln Arg Leu Leu Thr Gln Val Ile Asp Asp Asn Lys Phe Ile Asp
                        645                 650                 655
        Arg Asn Leu Asn Asp Thr Arg Tyr Ile Ala Arg Phe Leu Ser Asn Tyr
                        660                 665                 670
        Ile Gln Glu Asn Leu Leu Leu Val Gly Lys Asn Lys Lys Asn Val Phe
                        675                 680                 685
        Thr Pro Asn Gly Gln Ile Thr Ala Leu Leu Arg Ser Arg Trp Gly Leu
                        690                 695                 700
        Ile Lys Ala Arg Glu Asn Asn Arg His His Ala Leu Asp Ala Ile
        705                 710                 715                 720
        Val Val Ala Cys Ala Thr Pro Ser Met Gln Gln Lys Ile Thr Arg Phe
                        725                 730                 735
        Ile Arg Phe Lys Glu Val His Pro Tyr Lys Ile Glu Asn Arg Tyr Glu
                        740                 745                 750
        Met Val Asp Gln Glu Ser Gly Glu Ile Ile Ser Pro His Phe Pro Glu
                        755                 760                 765
        Pro Trp Ala Tyr Phe Arg Gln Glu Val Asn Ile Arg Val Phe Asp Asn
                        770                 775                 780
        His Pro Asp Thr Val Leu Lys Glu Met Leu Pro Asp Arg Pro Gln Ala
        785                 790                 795                 800
        Asn His Gln Phe Val Gln Pro Leu Phe Val Ser Arg Ala Pro Thr Arg
                        805                 810                 815
```

```
Lys Met Ser Gly Gln Gly His Met Glu Thr Ile Lys Ser Ala Lys Arg
            820                 825                 830

Leu Ala Glu Gly Ile Ser Val Leu Arg Ile Pro Leu Thr Gln Leu Lys
            835                 840                 845

Pro Asn Leu Leu Glu Asn Met Val Asn Lys Glu Arg Glu Pro Ala Leu
            850                 855                 860

Tyr Ala Gly Leu Lys Ala Arg Leu Ala Glu Phe Asn Gln Asp Pro Ala
865                 870                 875                 880

Lys Ala Phe Ala Thr Pro Phe Tyr Lys Gln Gly Gln Gln Val Lys
                885                 890                 895

Ala Ile Arg Val Glu Gln Val Gln Lys Ser Gly Val Leu Val Arg Glu
            900                 905                 910

Asn Asn Gly Val Ala Asp Asn Ala Ser Ile Val Arg Thr Asp Val Phe
            915                 920                 925

Ile Lys Asn Asn Lys Phe Phe Leu Val Pro Ile Tyr Thr Trp Gln Val
            930                 935                 940

Ala Lys Gly Ile Leu Pro Asn Lys Ala Ile Val Ala His Lys Asn Glu
945                 950                 955                 960

Asp Glu Trp Glu Met Asp Glu Gly Ala Lys Phe Lys Phe Ser Leu
                965                 970                 975

Phe Pro Asn Asp Leu Val Glu Leu Lys Thr Lys Glu Tyr Phe Phe
            980                 985                 990

Gly Tyr Tyr Ile Gly Leu Asp Arg Ala Thr Gly Asn Ile Ser Leu Lys
            995                 1000                1005

Glu His Asp Gly Glu Ile Ser Lys Gly Lys Asp Gly Val Tyr Arg
        1010                1015                1020

Val Gly Val Lys Leu Ala Leu Ser Phe Glu Lys Tyr Gln Val Asp
        1025                1030                1035

Glu Leu Gly Lys Asn Arg Gln Ile Cys Arg Pro Gln Gln Arg Gln
        1040                1045                1050

Pro Val Arg
    1055

<210> SEQ ID NO 28
<211> LENGTH: 936
<212> TYPE: PRT
<213> ORGANISM: Enterococcus faecalis TX4248
<220> FEATURE:
<221> NAME/KEY: MISC_FEATURE
<223> OTHER INFORMATION: E0G5X6_ENTFL

<400> SEQUENCE: 28

Met Lys Lys Asp Tyr Val Ile Gly Leu Asp Ile Gly Thr Asn Ser Val
1               5                   10                  15

Gly Trp Ala Val Met Thr Glu Asp Tyr Gln Leu Val Lys Lys Lys Met
            20                  25                  30

Pro Ile Tyr Gly Asn Thr Glu Lys Lys Ile Lys Lys Asn Phe Trp
        35                  40                  45

Gly Val Arg Leu Phe Glu Glu Gly His Thr Ala Glu Asp Arg Arg Leu
    50                  55                  60

Lys Arg Thr Ala Arg Arg Ile Ser Arg Arg Arg Asn Arg Leu Arg
65                  70                  75                  80

Tyr Leu Gln Ala Phe Phe Glu Glu Ala Met Thr Asp Leu Asp Glu Asn
                85                  90                  95

Phe Phe Ala Arg Leu Gln Glu Ser Phe Leu Val Pro Glu Asp Lys Lys
```

```
                100                 105                 110
Trp His Arg His Pro Ile Phe Ala Lys Leu Glu Asp Glu Val Ala Tyr
            115                 120                 125

His Glu Thr Tyr Pro Thr Ile Tyr His Leu Arg Lys Lys Leu Ala Asp
    130                 135                 140

Ser Ser Glu Gln Ala Asp Leu Arg Leu Ile Tyr Leu Ala Leu Ala His
145                 150                 155                 160

Ile Val Lys Tyr Arg Gly His Phe Leu Ile Glu Gly Lys Leu Ser Thr
                165                 170                 175

Glu Asn Ile Ser Val Lys Glu Gln Phe Gln Gln Phe Met Ile Ile Tyr
            180                 185                 190

Asn Gln Thr Phe Val Asn Gly Glu Ser Arg Leu Val Ser Ala Pro Leu
        195                 200                 205

Pro Glu Ser Val Leu Ile Glu Glu Leu Thr Glu Lys Ala Ser Arg
    210                 215                 220

Thr Lys Lys Ser Glu Lys Val Leu Gln Gln Phe Pro Gln Glu Lys Ala
225                 230                 235                 240

Asn Gly Leu Phe Gly Gln Phe Leu Lys Leu Met Val Gly Asn Lys Ala
                245                 250                 255

Asp Phe Lys Lys Val Phe Gly Leu Glu Glu Ala Lys Ile Thr Tyr
            260                 265                 270

Ala Ser Glu Ser Tyr Glu Glu Asp Leu Glu Gly Ile Leu Ala Lys Val
        275                 280                 285

Gly Asp Glu Tyr Ser Asp Val Phe Leu Ala Ala Lys Asn Val Tyr Asp
    290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
                325                 330                 335

Asp Leu Lys Lys Phe Lys Arg Phe Ile Arg Glu Asn Cys Pro Asp Glu
            340                 345                 350

Tyr Asp Asn Leu Phe Lys Asn Glu Gln Lys Asp Gly Tyr Ala Gly Tyr
        355                 360                 365

Ile Ala His Ala Gly Lys Val Ser Gln Leu Lys Phe Tyr Gln Tyr Val
    370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
                405                 410                 415

Val Ile Pro His Gln Ile His Leu Ala Glu Leu Gln Ala Ile Ile His
            420                 425                 430

Arg Gln Ala Ala Tyr Tyr Pro Phe Leu Lys Glu Asn Gln Glu Lys Ile
        435                 440                 445

Glu Gln Leu Val Thr Phe Arg Ile Pro Tyr Tyr Val Gly Pro Leu Ser
    450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
                485                 490                 495

Ala Thr Ala Phe Ile Glu Arg Met Thr Asn Phe Asp Thr Tyr Leu Pro
            500                 505                 510

Ser Glu Lys Val Leu Pro Lys His Ser Leu Leu Tyr Glu Lys Phe Met
        515                 520                 525
```

```
Val Phe Asn Glu Leu Thr Lys Ile Ser Tyr Thr Asp Asp Arg Gly Ile
    530                 535                 540

Lys Ala Asn Phe Ser Gly Lys Glu Lys Glu Lys Ile Phe Asp Tyr Leu
545                 550                 555                 560

Phe Lys Thr Arg Arg Lys Val Lys Lys Asp Ile Ile Gln Phe Tyr
                565                 570                 575

Arg Asn Glu Tyr Asn Thr Glu Ile Val Thr Leu Ser Gly Leu Glu Glu
                580                 585                 590

Asp Gln Phe Asn Ala Ser Phe Ser Thr Tyr Gln Asp Leu Leu Lys Cys
            595                 600                 605

Gly Leu Thr Arg Ala Glu Leu Asp His Pro Asp Asn Ala Glu Lys Leu
        610                 615                 620

Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Ala Glu Val Leu
                645                 650                 655

Lys Lys Leu Glu Arg Lys His Tyr Thr Gly Trp Gly Arg Leu Ser Lys
                660                 665                 670

Lys Leu Ile Asn Gly Ile Tyr Asp Lys Glu Ser Gly Lys Thr Ile Leu
            675                 680                 685

Gly Tyr Leu Ile Lys Asp Asp Gly Val Ser Lys His Tyr Asn Arg Asn
        690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val
                725                 730                 735

Asn Glu Leu Ala Gly Ser Pro Ala Ile Lys Lys Gly Ile Tyr Gln Ser
                740                 745                 750

Leu Lys Ile Val Asp Glu Leu Val Ala Ile Met Gly Tyr Ala Pro Lys
            755                 760                 765

Arg Ile Val Val Glu Met Ala Arg Glu Asn Gln Thr Thr Ser Thr Gly
770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
                805                 810                 815

Leu Arg Asp Thr Arg Leu Phe Leu Tyr Tyr Met Gln Asn Gly Lys Asp
            820                 825                 830

Met Tyr Thr Gly Asp Glu Leu Ser Leu His Arg Leu Ser His Tyr Asp
        835                 840                 845

Ile Asp His Ile Ile Pro Gln Ser Phe Met Lys Asp Asp Ser Leu Asp
850                 855                 860

Asn Leu Val Leu Val Gly Ser Thr Glu Asn Arg Gly Lys Ser Asp Asp
865                 870                 875                 880

Val Pro Ser Lys Glu Val Val Lys Asp Met Lys Ala Tyr Trp Glu Lys
                885                 890                 895

Leu Tyr Ala Ala Gly Leu Ile Ser Gln Arg Lys Phe Gln Arg Leu Thr
            900                 905                 910

Lys Gly Glu Gln Gly Gly Leu Thr Leu Glu Asp Lys Ala His Phe Ile
        915                 920                 925

Gln Arg Gln Leu Val Glu Thr Arg
    930                 935
```

<210> SEQ ID NO 29
<211> LENGTH: 1011
<212> TYPE: PRT
<213> ORGANISM: uncultured delta proteobacterium HF0070_07E19
<220> FEATURE:
<221> NAME/KEY: MISC_FEATURE
<223> OTHER INFORMATION: E0XXB7_9DELT

<400> SEQUENCE: 29

```
Met Ser Ser Lys Ala Ile Asp Ser Leu Glu Gln Leu Asp Leu Phe Lys
1               5                   10                  15

Pro Gln Glu Tyr Thr Leu Gly Leu Asp Leu Gly Ile Lys Ser Ile Gly
            20                  25                  30

Trp Ala Ile Leu Ser Gly Glu Arg Ile Ala Asn Ala Gly Val Tyr Leu
        35                  40                  45

Phe Glu Thr Ala Glu Glu Leu Asn Ser Thr Gly Asn Lys Leu Ile Ser
    50                  55                  60

Lys Ala Ala Glu Arg Gly Arg Lys Arg Arg Ile Arg Arg Met Leu Asp
65                  70                  75                  80

Arg Lys Ala Arg Arg Gly Arg His Ile Arg Tyr Leu Leu Arg Glu
                85                  90                  95

Gly Leu Pro Thr Asp Glu Leu Glu Glu Val Val His Gln Ser Asn
            100                 105                 110

Arg Thr Leu Trp Asp Val Arg Ala Glu Ala Val Glu Arg Lys Leu Thr
        115                 120                 125

Lys Gln Glu Leu Ala Ala Val Leu Phe His Leu Val Arg His Arg Gly
    130                 135                 140

Tyr Phe Pro Asn Thr Lys Lys Leu Pro Pro Asp Asp Glu Ser Asp Ser
145                 150                 155                 160

Ala Asp Glu Glu Gln Gly Lys Ile Asn Arg Ala Thr Ser Arg Leu Arg
                165                 170                 175

Glu Glu Leu Lys Ala Ser Asp Cys Lys Thr Ile Gly Gln Phe Leu Ala
            180                 185                 190

Gln Asn Arg Asp Arg Gln Arg Asn Arg Glu Gly Asp Tyr Ser Asn Leu
        195                 200                 205

Met Ala Arg Lys Leu Val Phe Glu Glu Ala Leu Gln Ile Leu Ala Phe
    210                 215                 220

Gln Arg Lys Gln Gly His Glu Leu Ser Lys Asp Phe Glu Lys Thr Tyr
225                 230                 235                 240

Leu Asp Val Leu Met Gly Gln Arg Ser Gly Arg Ser Pro Lys Leu Gly
                245                 250                 255

Asn Cys Ser Leu Ile Pro Ser Glu Leu Arg Ala Pro Ser Ser Ala Pro
            260                 265                 270

Ser Thr Glu Trp Phe Lys Phe Leu Gln Asn Leu Gly Asn Leu Gln Ile
        275                 280                 285

Ser Asn Ala Tyr Arg Glu Glu Trp Ser Ile Asp Ala Pro Arg Arg Ala
    290                 295                 300

Gln Ile Ile Asp Ala Cys Ser Gln Arg Ser Thr Ser Ser Tyr Trp Gln
305                 310                 315                 320

Ile Arg Arg Asp Phe Gln Ile Pro Asp Glu Tyr Arg Phe Asn Leu Val
                325                 330                 335

Asn Tyr Glu Arg Arg Asp Pro Asp Val Asp Leu Gln Glu Tyr Leu Gln
            340                 345                 350

Gln Gln Glu Arg Lys Thr Leu Ala Asn Phe Arg Asn Trp Lys Gln Leu
        355                 360                 365
```

```
Glu Lys Ile Ile Gly Thr Gly His Pro Ile Gln Thr Leu Asp Glu Ala
    370                 375                 380

Ala Arg Leu Ile Thr Leu Ile Lys Asp Asp Glu Lys Leu Ser Asp Gln
385                 390                 395                 400

Leu Ala Asp Leu Leu Pro Glu Ala Ser Asp Lys Ala Ile Thr Gln Leu
                405                 410                 415

Cys Glu Leu Asp Phe Thr Thr Ala Ala Lys Ile Ser Leu Glu Ala Met
                420                 425                 430

Tyr Arg Ile Leu Pro His Met Asn Gln Gly Met Gly Phe Phe Asp Ala
            435                 440                 445

Cys Gln Gln Glu Ser Leu Pro Glu Ile Gly Val Pro Ala Gly Asp
    450                 455                 460

Arg Val Pro Pro Phe Asp Glu Met Tyr Asn Pro Val Val Asn Arg Val
465                 470                 475                 480

Leu Ser Gln Ser Arg Lys Leu Ile Asn Ala Val Ile Asp Glu Tyr Gly
                485                 490                 495

Met Pro Ala Lys Ile Arg Val Glu Leu Ala Arg Asp Leu Gly Lys Gly
                500                 505                 510

Arg Glu Leu Arg Glu Arg Ile Lys Leu Asp Gln Leu Asp Lys Ser Lys
    515                 520                 525

Gln Asn Asp Gln Arg Ala Glu Asp Phe Arg Ala Glu Phe Gln Gln Ala
    530                 535                 540

Pro Arg Gly Asp Gln Ser Leu Arg Tyr Arg Leu Trp Lys Glu Gln Asn
545                 550                 555                 560

Cys Thr Cys Pro Tyr Ser Gly Arg Met Ile Pro Val Asn Ser Val Leu
                565                 570                 575

Ser Glu Asp Thr Gln Ile Asp His Ile Leu Pro Ile Ser Gln Ser Phe
                580                 585                 590

Asp Asn Ser Leu Ser Asn Lys Val Leu Cys Phe Thr Glu Glu Asn Ala
                595                 600                 605

Gln Lys Ser Asn Arg Thr Pro Phe Glu Tyr Leu Asp Ala Ala Asp Phe
    610                 615                 620

Gln Arg Leu Glu Ala Ile Ser Gly Asn Trp Pro Glu Ala Lys Arg Asn
625                 630                 635                 640

Lys Leu Leu His Lys Ser Phe Gly Lys Val Ala Glu Glu Trp Lys Ser
                645                 650                 655

Arg Ala Leu Asn Asp Thr Arg Tyr Leu Thr Ser Ala Leu Ala Asp His
                660                 665                 670

Leu Arg His His Leu Pro Asp Ser Lys Ile Gln Thr Val Asn Gly Arg
            675                 680                 685

Ile Thr Gly Tyr Leu Arg Lys Gln Trp Gly Leu Glu Lys Asp Arg Asp
            690                 695                 700

Lys His Thr His His Ala Val Asp Ala Ile Val Val Ala Cys Thr Thr
705                 710                 715                 720

Pro Ala Ile Val Gln Gln Val Thr Leu Tyr His Gln Asp Ile Arg Arg
                725                 730                 735

Tyr Lys Lys Leu Gly Glu Lys Arg Pro Thr Pro Trp Pro Glu Thr Phe
                740                 745                 750

Arg Gln Asp Val Leu Asp Val Glu Glu Glu Ile Phe Ile Thr Arg Gln
    755                 760                 765

Pro Lys Lys Val Ser Gly Gly Ile Gln Thr Lys Asp Thr Leu Arg Lys
770                 775                 780
```

His Arg Ser Lys Pro Asp Arg Gln Arg Val Ala Leu Thr Lys Val Lys
785                 790                 795                 800

Leu Ala Asp Leu Glu Arg Leu Val Glu Lys Asp Ala Ser Asn Arg Asn
                805                 810                 815

Leu Tyr Glu His Leu Lys Gln Cys Leu Glu Glu Ser Gly Asp Gln Pro
            820                 825                 830

Thr Lys Ala Phe Lys Ala Pro Phe Tyr Met Pro Ser Gly Pro Glu Ala
        835                 840                 845

Lys Gln Arg Pro Ile Leu Ser Lys Val Thr Leu Leu Arg Glu Lys Pro
    850                 855                 860

Glu Pro Pro Lys Gln Leu Thr Glu Leu Ser Gly Gly Arg Arg Tyr Asp
865                 870                 875                 880

Ser Met Ala Gln Gly Arg Leu Asp Ile Tyr Arg Tyr Lys Pro Gly Gly
                885                 890                 895

Lys Arg Lys Asp Glu Tyr Arg Val Val Leu Gln Arg Met Ile Asp Leu
            900                 905                 910

Met Arg Gly Glu Glu Asn Val His Val Phe Gln Lys Gly Val Pro Tyr
        915                 920                 925

Asp Gln Gly Pro Glu Ile Glu Gln Asn Tyr Thr Phe Leu Phe Ser Leu
    930                 935                 940

Tyr Phe Asp Asp Leu Val Glu Phe Gln Arg Ser Ala Asp Ser Glu Val
945                 950                 955                 960

Ile Arg Gly Tyr Tyr Arg Thr Phe Asn Ile Ala Asn Gly Gln Leu Lys
                965                 970                 975

Ile Ser Thr Tyr Leu Glu Gly Arg Gln Asp Phe Asp Phe Phe Gly Ala
            980                 985                 990

Asn Arg Leu Ala His Phe Ala Lys  Val Gln Val Asn Leu  Leu Gly Lys
        995                 1000                1005

Val Ile  Lys
    1010

<210> SEQ ID NO 30
<211> LENGTH: 957
<212> TYPE: PRT
<213> ORGANISM: artificial sequence
<220> FEATURE:
<223> OTHER INFORMATION: Cas9_Delta 956

<400> SEQUENCE: 30

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

```
His Glu Lys Tyr Pro Thr Ile Tyr His Leu Arg Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
```

```
           545                 550                 555                 560
    Val Lys Gln Leu Lys Glu Asp Tyr Phe Lys Ile Glu Cys Phe Asp
                        565                 570                 575

Ser Val Glu Ile Ser Gly Val Glu Asp Arg Phe Asn Ala Ser Leu Gly
                    580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Arg Leu Lys Thr Tyr Ala
    625                 630                 635                 640

His Leu Phe Asp Asp Lys Val Met Lys Gln Leu Lys Arg Arg Arg Tyr
                        645                 650                 655

Thr Gly Trp Gly Arg Leu Ser Arg Lys Leu Ile Asn Gly Ile Arg Asp
                    660                 665                 670

Lys Gln Ser Gly Lys Thr Ile Leu Asp Phe Leu Lys Ser Asp Gly Phe
                    675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
    705                 710                 715                 720

His Glu His Ile Ala Asn Leu Ala Gly Ser Pro Ala Ile Lys Lys Gly
                        725                 730                 735

Ile Leu Gln Thr Val Lys Val Val Asp Glu Leu Val Lys Val Met Gly
                    740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
    785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                    820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
    865                 870                 875                 880

Asn Tyr Trp Arg Gln Leu Leu Asn Ala Lys Leu Ile Thr Gln Arg Lys
                        885                 890                 895

Phe Asp Asn Leu Thr Lys Ala Glu Arg Gly Gly Leu Ser Glu Leu Asp
                    900                 905                 910

Lys Ala Gly Phe Ile Lys Arg Gln Leu Val Glu Thr Arg Gln Ile Thr
                    915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr
    945                 950                 955

<210> SEQ ID NO 31
```

<211> LENGTH: 943
<212> TYPE: PRT
<213> ORGANISM: artificial sequence
<220> FEATURE:
<223> OTHER INFORMATION: Cas9_Delta 943

<400> SEQUENCE: 31

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380
```

```
Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800
```

Val Glu Asn Thr Gln Leu Gln Asn Glu Lys Leu Tyr Leu Tyr Tyr Leu
              805                 810                 815

Gln Asn Gly Arg Asp Met Tyr Val Asp Gln Glu Leu Asp Ile Asn Arg
          820                 825                 830

Leu Ser Asp Tyr Asp Val Asp His Ile Val Pro Gln Ser Phe Leu Lys
      835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
              885                 890                 895

Phe Asp Asn Leu Thr Lys Ala Glu Arg Gly Gly Leu Ser Glu Leu Asp
          900                 905                 910

Lys Ala Gly Phe Ile Lys Arg Gln Leu Val Glu Thr Arg Gln Ile Thr
      915                 920                 925

Lys His Val Ala Gln Ile Leu Asp Ser Arg Met Asn Thr Lys Tyr
930                 935                 940

<210> SEQ ID NO 32
<211> LENGTH: 981
<212> TYPE: PRT
<213> ORGANISM: artificial sequence
<220> FEATURE:
<223> OTHER INFORMATION: Cas9_Delta 980

<400> SEQUENCE: 32

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

```
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
```

```
                    645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
        740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr
        980

<210> SEQ ID NO 33
<211> LENGTH: 1055
<212> TYPE: PRT
<213> ORGANISM: artificial sequence
<220> FEATURE:
<223> OTHER INFORMATION: Cas9_Delta 1055

<400> SEQUENCE: 33

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
```

```
                 20                  25                  30
Lys Val Leu Gly Asn Thr Asp Arg His Ser Ile Lys Lys Asn Leu Ile
             35                  40                  45
Gly Ala Leu Leu Phe Asp Ser Gly Glu Thr Ala Glu Ala Thr Arg Leu
         50                  55                  60
Lys Arg Thr Ala Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
             100                 105                 110
His Glu Arg His Pro Ile Phe Gly Asn Ile Val Asp Glu Val Ala Tyr
             115                 120                 125
His Glu Lys Tyr Pro Thr Ile Tyr His Leu Arg Lys Lys Leu Val Asp
             130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                 165                 170                 175
Asp Asn Ser Asp Val Asp Lys Leu Phe Ile Gln Leu Val Gln Thr Tyr
             180                 185                 190
Asn Gln Leu Phe Glu Glu Asn Pro Ile Asn Ala Ser Gly Val Asp Ala
             195                 200                 205
Lys Ala Ile Leu Ser Ala Arg Leu Ser Lys Ser Arg Arg Leu Glu Asn
             210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                 245                 250                 255
Asp Leu Ala Glu Asp Ala Lys Leu Gln Leu Ser Lys Asp Thr Tyr Asp
             260                 265                 270
Asp Asp Leu Asp Asn Leu Leu Ala Gln Ile Gly Asp Gln Tyr Ala Asp
             275                 280                 285
Leu Phe Leu Ala Ala Lys Asn Leu Ser Asp Ala Ile Leu Leu Ser Asp
         290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                 325                 330                 335
Ala Leu Val Arg Gln Gln Leu Pro Glu Lys Tyr Lys Glu Ile Phe Phe
             340                 345                 350
Asp Gln Ser Lys Asn Gly Tyr Ala Gly Tyr Ile Asp Gly Gly Ala Ser
             355                 360                 365
Gln Glu Glu Phe Tyr Lys Phe Ile Lys Pro Ile Leu Glu Lys Met Asp
             370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
             405                 410                 415
Gly Glu Leu His Ala Ile Leu Arg Arg Gln Glu Asp Phe Tyr Pro Phe
             420                 425                 430
Leu Lys Asp Asn Arg Glu Lys Ile Glu Lys Ile Leu Thr Phe Arg Ile
             435                 440                 445
```

-continued

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

```
Gly Lys Ser Asp Asn Val Pro Ser Glu Glu Val Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly
    1055

<210> SEQ ID NO 34
<211> LENGTH: 6
<212> TYPE: PRT
<213> ORGANISM: artificial sequence
<220> FEATURE:
<223> OTHER INFORMATION: DNA/RNA binding region 1

<400> SEQUENCE: 34

Ser Val Gly Trp Ala Val
1               5

<210> SEQ ID NO 35
<211> LENGTH: 5
<212> TYPE: PRT
<213> ORGANISM: artificial sequence
<220> FEATURE:
<223> OTHER INFORMATION: DNA/RNA binding region 2

<400> SEQUENCE: 35

Ser Lys Lys Phe Lys
1               5

<210> SEQ ID NO 36
<211> LENGTH: 17
<212> TYPE: PRT
<213> ORGANISM: artificial sequence
<220> FEATURE:
<223> OTHER INFORMATION: DNA/RNA binding region 3

<400> SEQUENCE: 36

Thr Arg Leu Lys Arg Thr Ala Arg Arg Tyr Thr Arg Arg Lys Asn
1               5                   10                  15

Arg
```

```
<210> SEQ ID NO 37
<211> LENGTH: 9
<212> TYPE: PRT
<213> ORGANISM: artificial sequence
<220> FEATURE:
<223> OTHER INFORMATION: DNA/RNA binding region 4

<400> SEQUENCE: 37

Ser Ala Arg Leu Ser Lys Ser Arg Arg
1               5

<210> SEQ ID NO 38
<211> LENGTH: 12
<212> TYPE: PRT
<213> ORGANISM: artificial sequence
<220> FEATURE:
<223> OTHER INFORMATION: DNA/RNA binding region 5

<400> SEQUENCE: 38

Lys Ala Pro Leu Ser Ala Ser Met Ile Lys Arg Tyr
1               5                   10

<210> SEQ ID NO 39
<211> LENGTH: 22
<212> TYPE: PRT
<213> ORGANISM: artificial sequence
<220> FEATURE:
<223> OTHER INFORMATION: DNA/RNA binding region 6

<400> SEQUENCE: 39

Phe Arg Ile Pro Tyr Tyr Val Gly Pro Leu Ala Arg Gly Asn Ser Arg
1               5                   10                  15

Phe Ala Trp Met Thr Arg
            20

<210> SEQ ID NO 40
<211> LENGTH: 11
<212> TYPE: PRT
<213> ORGANISM: artificial sequence
<220> FEATURE:
<223> OTHER INFORMATION: DNA/RNA binding region 7

<400> SEQUENCE: 40

Thr Lys Val Lys Tyr Val Thr Glu Gly Met Arg
1               5                   10

<210> SEQ ID NO 41
<211> LENGTH: 9
<212> TYPE: PRT
<213> ORGANISM: artificial sequence
<220> FEATURE:
<223> OTHER INFORMATION: DNA/RNA binding region 8

<400> SEQUENCE: 41

Arg Lys Val Thr Val Lys Gln Leu Lys
1               5

<210> SEQ ID NO 42
<211> LENGTH: 14
<212> TYPE: PRT
<213> ORGANISM: artificial sequence
<220> FEATURE:
<223> OTHER INFORMATION: DNA/RNA binding region 9

<400> SEQUENCE: 42
```

```
Lys Arg Arg Arg Tyr Thr Gly Trp Gly Arg Leu Ser Arg Lys
1               5                   10
```

<210> SEQ ID NO 43
<211> LENGTH: 13
<212> TYPE: PRT
<213> ORGANISM: artificial sequence
<220> FEATURE:
<223> OTHER INFORMATION: DNA/RNA binding region 10

<400> SEQUENCE: 43

```
Gln Thr Thr Gln Lys Gly Gln Lys Asn Ser Arg Glu Arg
1               5                   10
```

<210> SEQ ID NO 44
<211> LENGTH: 9
<212> TYPE: PRT
<213> ORGANISM: artificial sequence
<220> FEATURE:
<223> OTHER INFORMATION: DNA/RNA binding region 11

<400> SEQUENCE: 44

```
Arg Ser Asp Lys Asn Arg Gly Lys Ser
1               5
```

<210> SEQ ID NO 45
<211> LENGTH: 13
<212> TYPE: PRT
<213> ORGANISM: artificial sequence
<220> FEATURE:
<223> OTHER INFORMATION: DNA/RNA binding region 12

<400> SEQUENCE: 45

```
Lys Lys Met Lys Asn Tyr Trp Arg Gln Leu Leu Asn Ala
1               5                   10
```

<210> SEQ ID NO 46
<211> LENGTH: 10
<212> TYPE: PRT
<213> ORGANISM: artificial sequence
<220> FEATURE:
<223> OTHER INFORMATION: DNA/RNA binding region 13

<400> SEQUENCE: 46

```
Asn Asn Tyr His His Ala His Asp Ala Tyr
1               5                   10
```

<210> SEQ ID NO 47
<211> LENGTH: 10
<212> TYPE: PRT
<213> ORGANISM: artificial sequence
<220> FEATURE:
<223> OTHER INFORMATION: DNA/RNA binding region 14

<400> SEQUENCE: 47

```
Glu Lys Gly Lys Ser Lys Lys Leu Lys Ser
1               5                   10
```

<210> SEQ ID NO 48
<211> LENGTH: 9
<212> TYPE: PRT
<213> ORGANISM: artificial sequence
<220> FEATURE:
<223> OTHER INFORMATION: DNA/RNA binding region 15

<400> SEQUENCE: 48

```
Arg Lys Arg Tyr Thr Ser Thr Lys Glu
1               5
```

<210> SEQ ID NO 49
<211> LENGTH: 329
<212> TYPE: PRT
<213> ORGANISM: Fusobacterium necrophorum subsp. funduliforme 1_1_36S
<220> FEATURE:
<221> NAME/KEY: MISC_FEATURE
<223> OTHER INFORMATION: H1D478_9FUSO

<400> SEQUENCE: 49

Met Glu Asn Gly Lys Leu Asn Glu Val Glu Asn Ile Leu Lys Asp Arg
1               5                   10                  15

Asn Leu Ala Lys Ser Glu Lys Glu Lys Leu Tyr Gly Leu Ile Glu
            20                  25                  30

Leu Glu Gly Lys Ile Asp Asn Gln Arg Lys Ala Met Ile Gly Met Met
        35                  40                  45

Cys Gly Cys Lys Lys Lys Phe Ser Asp Leu Phe Gln Asn Glu Asn Tyr
50                  55                  60

Arg Glu Leu Glu Ile Ser Ser Phe Ser Phe Ala Asp Ser Ser Tyr Glu
65                  70                  75                  80

Glu Lys Arg Asp Glu Leu Glu Gly Ile Leu Ala Glu Asn Ile Leu Cys
                85                  90                  95

Leu Asp Tyr Leu Lys Thr Ile Tyr Asp Trp Gly Lys Leu Ser Asp Ile
            100                 105                 110

Leu Gln Gly Glu Glu Ser Ile Ser Val Ala Lys Val Lys Ser Tyr Glu
        115                 120                 125

Glu His Gln Leu Asp Leu Lys Tyr Leu Lys Asn Ile Leu Lys Leu Tyr
130                 135                 140

Ser His Lys Glu Lys Glu Asn Val Phe Arg Lys Lys Glu Gly Lys Tyr
145                 150                 155                 160

Pro Lys Tyr Ile Ser Gly Lys Leu Ser Gln Glu Glu Phe Asn Lys Ser
                165                 170                 175

Ile Lys Lys Ile Leu Glu Glu Ile Lys Ser Val Lys Gln Glu Asp Arg
            180                 185                 190

Lys Val Phe Asp Thr Leu Leu Lys Arg Ala Ser Asn Asn Leu Leu Cys
        195                 200                 205

Pro Lys Gln Val Ile Lys Glu Asn Gly Val Ile Pro Tyr Gln Ile His
210                 215                 220

Lys Phe Glu Leu Glu Lys Ile Leu Arg Asn Met Ala Asp Phe Phe Pro
225                 230                 235                 240

Met Leu Asn Glu Lys Lys Asp Gly Lys Thr Leu Ser Glu Lys Ile Ile
                245                 250                 255

Ser Val Phe Thr Phe Arg Ile Pro Tyr Tyr Val Gly Pro Leu Asn Gln
            260                 265                 270

Asn Ser Asp Arg Ala Trp Leu Val Lys Asn Lys Asp Glu Lys Ile Tyr
        275                 280                 285

Pro Trp Asn Phe Glu Glu Ile Val Asn Leu Glu Glu Ser Ala Glu Lys
290                 295                 300

Phe Ile Gln Asn Leu Thr Asn Lys Cys Thr Tyr Leu Val Leu Glu Asp
305                 310                 315                 320

Val Leu Pro Lys Ile Phe Tyr Thr Ile
                325

<210> SEQ ID NO 50
<211> LENGTH: 563

```
<212> TYPE: PRT
<213> ORGANISM: Lactobacillus crispatus FB077-07
<220> FEATURE:
<221> NAME/KEY: MISC_FEATURE
<223> OTHER INFORMATION: K1NA00_9LACO

<400> SEQUENCE: 50

Met Tyr Lys Asn Tyr Ile Thr Gly Gln Thr Ala Leu Thr Leu Asn Leu
1               5                   10                  15

Asp Phe Ala Ile Pro Ala Asn His Leu Ala Asn Val Ile Ser Trp Phe
            20                  25                  30

Val Asp Ser Ile Pro Glu Asp Val Leu Val Gly Lys Thr Ala Lys Thr
        35                  40                  45

Gly Arg Pro Ala Tyr His Pro Ala Met Met Leu Lys Ile Leu Leu Phe
    50                  55                  60

Ala Tyr Ser Arg Arg Val Phe Ser Gly Arg Lys Ile Glu Leu Met Leu
65                  70                  75                  80

Glu Glu Asn Leu Pro Met Met Ile Leu Ala Asp Gln Gln Lys Ile Ser
                85                  90                  95

Tyr His Thr Ile Asn Asn Phe Arg Ser Ser His Ala Asn Glu Leu
            100                 105                 110

Ile Lys Lys Ser Phe Ile Tyr Phe Thr Asn Leu Leu Glu Asp Glu Gly
        115                 120                 125

Leu Ile Asn Glu Gly Ala Ala Phe Ile Asp Gly Thr Lys Ile Glu Ala
    130                 135                 140

Asp Ala Asn Arg Tyr Thr Phe Val Trp Arg Lys Ala Val Glu Lys Tyr
145                 150                 155                 160

His Glu Lys Leu Lys Gly Gln Ala Val Glu Leu Tyr Asp Glu Leu Ile
                165                 170                 175

Thr Lys Glu Val Val Lys Glu Met Glu Lys Glu Lys Val Gln Thr Ser
            180                 185                 190

Gln Gly Leu Lys Glu Leu Ala Gln Glu Thr Glu Ala Glu Ile Asn Lys
    195                 200                 205

Leu Thr Lys Glu Ile Glu Gln Glu Asn Lys Ala Ile Pro Gly Gly Ser
210                 215                 220

Pro Arg Lys Ala Lys Arg Arg Gly Leu Lys Lys Ile Leu His Arg Leu
225                 230                 235                 240

Arg Lys Asp Tyr Val Pro Arg Met Gln Lys Tyr Glu Glu Ala Glu Glu
                245                 250                 255

Ile Phe Ala Gly Arg Asn Ser Tyr Ser Lys Thr Asp His Asp Ala Thr
            260                 265                 270

Phe Met His Met Lys Glu Asp His Met Lys Asn Gly Gln Leu Lys Pro
    275                 280                 285

Gly Tyr Asn Ile Gln Ala Val Thr Thr Asp Gln Tyr Val Val Asp Tyr
    290                 295                 300

Ala Ile Phe Pro Asn Pro Thr Asp Phe Lys Thr Leu Glu Pro Val Leu
305                 310                 315                 320

Asp Gln Met Thr Val Leu Asp Lys Phe Asp Lys Ile Val Ala Asp Ala
                325                 330                 335

Gly Tyr Gly Ser Glu Tyr Asn Tyr Ser Met Leu Glu Glu Lys Tyr Pro
            340                 345                 350

Asp Lys Lys Tyr Phe Ile Pro Tyr Thr Met Tyr Glu Lys Glu Gln Thr
    355                 360                 365

Lys Lys Tyr Lys Asn Asp Pro Thr Lys Leu Ile Asn Trp Tyr Tyr Asn
370                 375                 380
```

```
Glu Lys Asp Asp Tyr Tyr Ile Asp His His Gly Val Arg Phe Asn Phe
385                 390                 395                 400

Lys Tyr Tyr Ser Gln Arg Lys Asp Arg Ser Thr Gly Gln Val Arg Asp
            405                 410                 415

Phe Lys Val Tyr Glu Ala Asp Glu Phe Gln Leu Thr Pro Glu Leu Glu
        420                 425                 430

Gln Leu Ala Lys Thr Ala Ser Gly Arg Gln Arg Gln Val Arg Tyr Asn
            435                 440                 445

Pro Asn Trp Gln Tyr Leu Lys Glu Lys Ala Lys Glu Val Leu Gln Ser
        450                 455                 460

Glu Glu Gly Arg His Ile Tyr Gly Met Arg Lys Tyr Asp Val Glu Pro
465                 470                 475                 480

Val Phe Gly His Leu Lys Asn Val Phe Gly Met Arg Arg Thr His Leu
                485                 490                 495

Arg Gly Lys Glu Lys Val Glu Thr Asp Ile Gly Ile Ala Phe Met Met
            500                 505                 510

Met Asn Leu Asn Lys Tyr Cys Gln Arg Arg Trp Leu Lys Gly Arg Phe
            515                 520                 525

Leu Leu Leu Lys Ile Leu Lys Arg Thr Lys Lys Arg Ser Arg Phe Leu
            530                 535                 540

Lys Lys Glu Ile Leu Ile Val Phe Ile His Leu Glu Ala Ile Phe Phe
545                 550                 555                 560

Pro Asp Thr

<210> SEQ ID NO 51
<211> LENGTH: 357
<212> TYPE: PRT
<213> ORGANISM: Treponema denticola
<220> FEATURE:
<221> NAME/KEY: MISC_FEATURE
<223> OTHER INFORMATION: E9SOG6

<400> SEQUENCE: 51

Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
            20                  25                  30

Ala Asn Arg Lys Asp Leu Trp Gly Met Arg Cys Phe Glu Thr Ala Glu
        35                  40                  45

Thr Ala Glu Val Arg Arg Leu His Arg Gly Ala Arg Arg Arg Ile Glu
    50                  55                  60

Arg Arg Lys Lys Arg Ile Lys Leu Leu Gln Glu Leu Phe Ser Gln Glu
65                  70                  75                  80

Ile Ala Lys Thr Asp Glu Gly Phe Phe Gln Arg Met Lys Glu Ser Pro
                85                  90                  95

Phe Tyr Ala Glu Asp Lys Thr Ile Leu Gln Glu Asn Ala Leu Phe Asn
            100                 105                 110

Asp Arg Asp Phe Thr Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175
```

Ile Gln Ala Phe Phe Glu Tyr Leu Arg Glu Asp Met Glu Val Asp Ile
                180                 185                 190

Asp Ala Asp Ser Gln Lys Ile Lys Glu Ile Leu Lys Asp Ser Ser Leu
            195                 200                 205

Lys Asn Ser Glu Lys Gln Ser Arg Leu Asn Lys Ile Leu Gly Leu Lys
        210                 215                 220

Ser Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Ile Thr Thr
            340                 345                 350

Ile Thr Pro Asp Met
            355

<210> SEQ ID NO 52
<211> LENGTH: 247
<212> TYPE: PRT
<213> ORGANISM: artificial sequence
<220> FEATURE:
<223> OTHER INFORMATION: Synthetic polypeptides: Split Cas9 RuvC

<400> SEQUENCE: 52

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Asn Gly Leu Phe Gly Asn
225                 230                 235                 240

Leu Ile Ala Leu Ser Leu Gly
                245

<210> SEQ ID NO 53
<211> LENGTH: 1121
<212> TYPE: PRT
<213> ORGANISM: artificial sequence
<220> FEATURE:
<223> OTHER INFORMATION: Synthetic polypeptides: Split Cas9 HNH

<400> SEQUENCE: 53

Leu Thr Pro Asn Phe Lys Ser Asn Phe Asp Leu Ala Glu Asp Ala Lys
1               5                   10                  15

Leu Gln Leu Ser Lys Asp Thr Tyr Asp Asp Leu Asp Asn Leu Leu
            20                  25                  30

Ala Gln Ile Gly Asp Gln Tyr Ala Asp Leu Phe Leu Ala Ala Lys Asn
            35                  40                  45

Leu Ser Asp Ala Ile Leu Leu Ser Asp Ile Leu Arg Val Asn Thr Glu
    50                  55                  60

Ile Thr Lys Ala Pro Leu Ser Ala Ser Met Ile Lys Arg Tyr Asp Glu
65                  70                  75                  80

His His Gln Asp Leu Thr Leu Leu Lys Ala Leu Val Arg Gln Gln Leu
                85                  90                  95

Pro Glu Lys Tyr Lys Glu Ile Phe Phe Asp Gln Ser Lys Asn Gly Tyr
            100                 105                 110

Ala Gly Tyr Ile Asp Gly Gly Ala Ser Gln Glu Glu Phe Tyr Lys Phe
        115                 120                 125

Ile Lys Pro Ile Leu Glu Lys Met Asp Gly Thr Glu Glu Leu Leu Val
    130                 135                 140

Lys Leu Asn Arg Glu Asp Leu Leu Arg Lys Gln Arg Thr Phe Asp Asn
145                 150                 155                 160

Gly Ser Ile Pro His Gln Ile His Leu Gly Glu Leu His Ala Ile Leu
                165                 170                 175

Arg Arg Gln Glu Asp Phe Tyr Pro Phe Leu Lys Asp Asn Arg Glu Lys
            180                 185                 190

Ile Glu Lys Ile Leu Thr Phe Arg Ile Pro Tyr Tyr Val Gly Pro Leu
        195                 200                 205

Ala Arg Gly Asn Ser Arg Phe Ala Trp Met Thr Arg Lys Ser Glu Glu
    210                 215                 220

Thr Ile Thr Pro Trp Asn Phe Glu Glu Val Val Asp Lys Gly Ala Ser
225                 230                 235                 240

Ala Gln Ser Phe Ile Glu Arg Met Thr Asn Phe Asp Lys Asn Leu Pro
                245                 250                 255

Asn Glu Lys Val Leu Pro Lys His Ser Leu Leu Tyr Glu Tyr Phe Thr
            260                 265                 270

Val Tyr Asn Glu Leu Thr Lys Val Lys Tyr Val Thr Glu Gly Met Arg
        275                 280                 285
```

```
Lys Pro Ala Phe Leu Ser Gly Glu Gln Lys Lys Ala Ile Val Asp Leu
    290                 295                 300

Leu Phe Lys Thr Asn Arg Lys Val Thr Val Lys Gln Leu Lys Glu Asp
305                 310                 315                 320

Tyr Phe Lys Lys Ile Glu Cys Phe Asp Ser Val Glu Ile Ser Gly Val
                325                 330                 335

Glu Asp Arg Phe Asn Ala Ser Leu Gly Thr Tyr His Asp Leu Leu Lys
                340                 345                 350

Ile Ile Lys Asp Lys Asp Phe Leu Asp Asn Glu Glu Asn Glu Asp Ile
            355                 360                 365

Leu Glu Asp Ile Val Leu Thr Leu Thr Leu Phe Glu Asp Arg Glu Met
370                 375                 380

Ile Glu Glu Arg Leu Lys Thr Tyr Ala His Leu Phe Asp Asp Lys Val
385                 390                 395                 400

Met Lys Gln Leu Lys Arg Arg Arg Tyr Thr Gly Trp Gly Arg Leu Ser
                405                 410                 415

Arg Lys Leu Ile Asn Gly Ile Arg Asp Lys Gln Ser Gly Lys Thr Ile
                420                 425                 430

Leu Asp Phe Leu Lys Ser Asp Gly Phe Ala Asn Arg Asn Phe Met Gln
        435                 440                 445

Leu Ile His Asp Asp Ser Leu Thr Phe Lys Glu Asp Ile Gln Lys Ala
450                 455                 460

Gln Val Ser Gly Gln Gly Asp Ser Leu His Glu His Ile Ala Asn Leu
465                 470                 475                 480

Ala Gly Ser Pro Ala Ile Lys Lys Gly Ile Leu Gln Thr Val Lys Val
                485                 490                 495

Val Asp Glu Leu Val Lys Val Met Gly Arg His Lys Pro Glu Asn Ile
            500                 505                 510

Val Ile Glu Met Ala Arg Glu Asn Gln Thr Thr Gln Lys Gly Gln Lys
        515                 520                 525

Asn Ser Arg Glu Arg Met Lys Arg Ile Glu Glu Gly Ile Lys Glu Leu
530                 535                 540

Gly Ser Gln Ile Leu Lys Glu His Pro Val Glu Asn Thr Gln Leu Gln
545                 550                 555                 560

Asn Glu Lys Leu Tyr Leu Tyr Tyr Leu Gln Asn Gly Arg Asp Met Tyr
                565                 570                 575

Val Asp Gln Glu Leu Asp Ile Asn Arg Leu Ser Asp Tyr Asp Val Asp
            580                 585                 590

His Ile Val Pro Gln Ser Phe Leu Lys Asp Asp Ser Ile Asp Asn Lys
        595                 600                 605

Val Leu Thr Arg Ser Asp Lys Asn Arg Gly Lys Ser Asp Asn Val Pro
610                 615                 620

Ser Glu Glu Val Val Lys Lys Met Lys Asn Tyr Trp Arg Gln Leu Leu
625                 630                 635                 640

Asn Ala Lys Leu Ile Thr Gln Arg Lys Phe Asp Asn Leu Thr Lys Ala
                645                 650                 655

Glu Arg Gly Gly Leu Ser Glu Leu Asp Lys Ala Gly Phe Ile Lys Arg
            660                 665                 670

Gln Leu Val Glu Thr Arg Gln Ile Thr Lys His Val Ala Gln Ile Leu
        675                 680                 685

Asp Ser Arg Met Asn Thr Lys Tyr Asp Glu Asn Asp Lys Leu Ile Arg
690                 695                 700
```

```
Glu Val Lys Val Ile Thr Leu Lys Ser Lys Leu Val Ser Asp Phe Arg
705                 710                 715                 720

Lys Asp Phe Gln Phe Tyr Lys Val Arg Glu Ile Asn Asn Tyr His His
                725                 730                 735

Ala His Asp Ala Tyr Leu Asn Ala Val Val Gly Thr Ala Leu Ile Lys
                740                 745                 750

Lys Tyr Pro Lys Leu Glu Ser Glu Phe Val Tyr Gly Asp Tyr Lys Val
                755                 760                 765

Tyr Asp Val Arg Lys Met Ile Ala Lys Ser Glu Gln Glu Ile Gly Lys
770                 775                 780

Ala Thr Ala Lys Tyr Phe Phe Tyr Ser Asn Ile Met Asn Phe Phe Lys
785                 790                 795                 800

Thr Glu Ile Thr Leu Ala Asn Gly Glu Ile Arg Lys Arg Pro Leu Ile
                805                 810                 815

Glu Thr Asn Gly Glu Thr Gly Glu Ile Val Trp Asp Lys Gly Arg Asp
                820                 825                 830

Phe Ala Thr Val Arg Lys Val Leu Ser Met Pro Gln Val Asn Ile Val
                835                 840                 845

Lys Lys Thr Glu Val Gln Thr Gly Gly Phe Ser Lys Glu Ser Ile Leu
850                 855                 860

Pro Lys Arg Asn Ser Asp Lys Leu Ile Ala Arg Lys Lys Asp Trp Asp
865                 870                 875                 880

Pro Lys Lys Tyr Gly Gly Phe Asp Ser Pro Thr Val Ala Tyr Ser Val
                885                 890                 895

Leu Val Val Ala Lys Val Glu Lys Gly Lys Ser Lys Lys Leu Lys Ser
                900                 905                 910

Val Lys Glu Leu Leu Gly Ile Thr Ile Met Glu Arg Ser Ser Phe Glu
                915                 920                 925

Lys Asn Pro Ile Asp Phe Leu Glu Ala Lys Gly Tyr Lys Glu Val Lys
                930                 935                 940

Lys Asp Leu Ile Ile Lys Leu Pro Lys Tyr Ser Leu Phe Glu Leu Glu
945                 950                 955                 960

Asn Gly Arg Lys Arg Met Leu Ala Ser Ala Gly Glu Leu Gln Lys Gly
                965                 970                 975

Asn Glu Leu Ala Leu Pro Ser Lys Tyr Val Asn Phe Leu Tyr Leu Ala
                980                 985                 990

Ser His Tyr Glu Lys Leu Lys Gly Ser Pro Glu Asp Asn Glu Gln Lys
                995                 1000                1005

Gln Leu Phe Val Glu Gln His Lys His Tyr Leu Asp Glu Ile Ile
    1010                1015                1020

Glu Gln Ile Ser Glu Phe Ser Lys Arg Val Ile Leu Ala Asp Ala
    1025                1030                1035

Asn Leu Asp Lys Val Leu Ser Ala Tyr Asn Lys His Arg Asp Lys
    1040                1045                1050

Pro Ile Arg Glu Gln Ala Glu Asn Ile Ile His Leu Phe Thr Leu
    1055                1060                1065

Thr Asn Leu Gly Ala Pro Ala Ala Phe Lys Tyr Phe Asp Thr Thr
    1070                1075                1080

Ile Asp Arg Lys Arg Tyr Thr Ser Thr Lys Glu Val Leu Asp Ala
    1085                1090                1095

Thr Leu Ile His Gln Ser Ile Thr Gly Leu Tyr Glu Thr Arg Ile
    1100                1105                1110

Asp Leu Ser Gln Leu Gly Gly Asp
```

```
                        1115                    1120

<210> SEQ ID NO 54
<211> LENGTH: 828
<212> TYPE: DNA
<213> ORGANISM: artificial sequence
<220> FEATURE:
<223> OTHER INFORMATION: synthetic polynucleotide: pCLS24814

<400> SEQUENCE: 54
atgaaggaga ccgccgctgc caagttcgag agacagcaca tggacagcgg ttctggcgat      60
cctaaaaaga aacgtaaggt cggctcggac aagaagtaca gcatcggcct ggacatcggc     120
accaactctg tgggctgggc cgtgatcacc gacgagtaca aggtgcccag caagaaattc     180
aaggtgctgg gcaacaccga ccggcacagc atcaagaaga acctgatcgg cgccctgctg     240
ttcgacagcg agaaacagc cgaggccacc cggctgaaga gaaccgccag aagaagatac     300
accagacgga agaaccggat ctgctatctg aagagatct tcagcaacga gatggccaag     360
gtggacgaca gcttcttcca cagactggaa gagtccttcc tggtggaaga ggataagaag     420
cacgagcggc accccatctt cggcaacatc gtggacgagg tggcctacca cgagaagtac     480
cccaccatct accacctgag aaagaaactg gtggacagca ccgacaaggc cgacctgcgg     540
ctgatctatc tggccctggc ccacatgatc aagttccggg gccacttcct gatcgagggc     600
gacctgaacc ccgacaacag cgacgtggac aagctgttca tccagctggt gcagacctac     660
aaccagctgt tcgaggaaaa ccccatcaac gccagcggcg tggacgccaa ggccatcctg     720
tctgccagac tgagcaagag cagacggctg gaaaatctga tcgcccagct gcccggcgag     780
aagaagaatg gcctgttcgg caacctgatt gccctgagcc tgggctaa                 828

<210> SEQ ID NO 55
<211> LENGTH: 4164
<212> TYPE: DNA
<213> ORGANISM: artificial sequence
<220> FEATURE:
<223> OTHER INFORMATION: synthetic polynucleotide: pCLS24813

<400> SEQUENCE: 55
atggtgaccc ccaacttcaa gagcaacttc gacctggccg aggatgccaa actgcagctg      60
agcaaggaca cctacgacga cgacctggac aacctgctgg cccagatcgg cgaccagtac     120
gccgacctgt ttctggccgc caagaacctg tccgacgcca tcctgctgag cgacatcctg     180
agagtgaaca ccgagatcac caaggccccc ctgagcgcct ctatgatcaa agatacgac     240 gagcaccacc aggacctgac cctgctgaaa gctctcgtgc ggcagcagct gcctgagaag     300
tacaaagaga tttttcttcga ccagagcaag aacggctacg ccggctacat cgatggcgga     360
gccagccagg aagagttcta caagttcatc aagcccatcc tggaaaagat ggacggcacc     420
gaggaactgc tcgtgaagct gaacagagag gacctgctgc ggaagcagcg gaccttcgac     480
aacggcagca tcccccacca gatccacctg ggagagctgc acgccattct gcggcggcag     540
gaagattttt acccattcct gaaggacaac cgggaaaaga tcgagaagat cctgaccttc     600
cgcatcccct actacgtggg ccctctggcc aggggaaaca gcagattcgc ctggatgacc     660
agaaagagcg aggaaaccat caccccctgg aacttcgagg aagtggtgga caagggcgcc     720
agcgcccaga gcttcatcga gcggatgacc aacttcgata agaacctgcc caacgagaag     780
gtgctgccca gcacagcct gctgtacgag tacttcaccg tgtacaacga gctgaccaaa     840
gtgaaatacg tgaccgaggg aatgagaaag cccgccttcc tgagcggcga gcagaaaaaa     900
```

-continued

```
gccatcgtgg acctgctgtt caagaccaac cggaaagtga ccgtgaagca gctgaaagag    960
gactacttca agaaaatcga gtgcttcgac tccgtggaaa tctccggcgt ggaagatcgg   1020
ttcaacgcct ccctgggcac ataccacgat ctgctgaaaa ttatcaagga caaggacttc   1080
ctggacaatg aggaaaacga ggacattctg gaagatatcg tgctgaccct gacactgttt   1140
gaggacagag agatgatcga ggaacggctg aaaacctatg cccacctgtt cgacgacaaa   1200
gtgatgaagc agctgaagcg gcggagatac accggctggg caggctgag ccggaagctg    1260 atcaacggca tccgggacaa gcagtccggc aagacaatcc tggatttcct gaagtccgac   1320
ggcttcgcca acagaaactt catgcagctg atccacgacg acagcctgac ctttaaagag   1380
gacatccaga agcccaggt gtccggccag ggcgatagcc tgcacgagca cattgccaat    1440
ctggccggca gccccgccat taagaagggc atcctgcaga cagtgaaggt ggtggacgag   1500
ctcgtgaaag tgatgggccg gcacaagccc gagaacatcg tgatcgaaat ggccagagag   1560
aaccagacca cccagaaggg acagaagaac agccgcgaga aatgaagcg gatcgaagag    1620 ggcatcaaag agctgggcag ccagatcctg aaagaacacc ccgtggaaaa cacccagctg   1680
cagaacgaga agctgtacct gtactacctg cagaatgggc gggatatgta cgtggaccag   1740
gaactggaca tcaaccggct gtccgactac gatgtggacc atatcgtgcc tcagagcttt   1800
ctgaaggacg actccatcga taacaaagtg ctgactcgga gcgacaagaa ccggggcaag   1860
agcgacaacg tgccctccga gaggtcgtg aagaagatga gaactactg cgccagctg     1920 ctgaatgcca gctgattac ccagaggaag ttcgacaatc tgaccaaggc cgagagaggc    1980
ggcctgagcg aactggataa ggccggcttc atcaagagac agctggtgga aacccggcag   2040
atcacaaagc acgtggcaca gatcctggac tccggatga acactaagta cgacgagaac    2100
gacaaactga tccgggaagt gaaagtgatc accctgaagt ccaagctggt gtccgatttc   2160
cggaaggatt tccagttta caaagtgcgc gagatcaaca actaccacca cgcccacgac   2220
gcctacctga acgccgtcgt gggaaccgcc ctgatcaaaa agtaccctaa gctggaaagc   2280
gagttcgtgt acggcgacta caaggtgtac gacgtgcgga agatgatcgc caagagcgag   2340
caggaaatcg gcaaggctac cgccaagtac ttcttctaca gcaacatcat gaacttttc    2400 aagaccgaga ttaccctggc caacggcgag atccggaagc ggcctctgat cgagacaaac   2460
ggcgaaacag cgagatcgt gtgggataag gccgggact tgccaccgt gcggaaagtg     2520 ctgtctatgc cccaagtgaa tatcgtgaaa aagaccgagg tgcagacagg cggcttcagc   2580 aaaagagtcta tcctgcccaa gaggaacagc gacaagctga tcgccagaaa gaaggactgg   2640
gaccctaaga gtacggcgg cttcgacagc cccaccgtgg cctattctgt gctggtggtg    2700
gccaaagtga aaagggcaa gtccaagaaa ctgaagagtg tgaaagagct gctgggatc    2760 accatcatgg aaagaagcag cttcgagaag aatcccatcg actttctgga agccaagggc   2820
tacaaagaag tgaaaaagga cctgatcatc aagctgccta agtactccct gttcgagctg   2880
gaaaacggcc ggaagagaat gctggcctct gccggcgaac tgcagaaggg aaacgaactg   2940 gccctgcct ccaaatatgt gaacttcctg tacctggcca gccactatga aagctgaag    3000 ggctccccg aggataatga gcagaaacag ctgtttgtgg aacagcacaa acactacctg   3060
gacgagatca tcgagcagat cagcgagttc tccaagagag tgatcctggc cgacgctaat   3120
ctggacaagg tgctgagcgc ctacaacaag cacagagaca gcctatcag agagcaggcc    3180 gagaatatca tccacctgtt taccctgacc aatctgggag cccctgccgc cttcaagtac   3240
```

| | |
|---|---|
| tttgacacca ccatcgaccg gaagaggtac accagcacca agaggtgct ggacgccacc | 3300 |
| ctgatccacc agagcatcac cggcctgtac gagacacgga tcgacctgtc tcagctggga | 3360 |
| ggcgacggat ccccgaagaa aaagcggaag gtcgagagtc caagaagaa gcgcaaagtg | 3420 |
| gaggggaatt ctggttctag cgagctgatt aaggagaaca tgcacatgaa gctgtacatg | 3480 |
| gagggcaccg tggacaacca tcacttcaag tgcacatccg agggcgaagg caagccctac | 3540 |
| gagggcaccc agaccatgag aatcaaggtg tcgagggcg ccctctccc cttcgccttc | 3600 |
| gacatcctgg ctactagctt cctctacggc agcaagacct tcatcaacca cacccagggc | 3660 |
| atccccgact tcttcaagca gtccttccct gagggcttca catgggagag agtcaccaca | 3720 |
| tacgaagacg ggggcgtgct gaccgctacc caggacacca gcctccagga cggctgcctc | 3780 |
| atctacaacg tcaagatcag aggggtgaac ttcacatcca acggcccgt gatgcagaag | 3840 |
| aaaacactcg gctgggaggc cttcaccgag acgctgtacc ccgctgacgg cggcctggaa | 3900 |
| ggcagaaacg acatggccct gaagctcgtg ggcgggagcc atctgatcgc aaacatcaag | 3960 |
| accacatata gatccaagaa acccgctaag aacctcaaga tgcctggcgt ctactatgtg | 4020 |
| gactacagac tggaaagaat caaggaggcc aacaacgaga cctacgtcga gcagcacgag | 4080 |
| gtggcagtgg ccagatactg cgacctccct agcaaactgg ggcacaagct taattatcca | 4140 |
| tacgacgttc ctgattacgc gtaa | 4164 |

<210> SEQ ID NO 56
<211> LENGTH: 20
<212> TYPE: DNA
<213> ORGANISM: artificial sequence
<220> FEATURE:
<223> OTHER INFORMATION: Synthetic oligonucleotide: target sequence: GFP_C9_T01

<400> SEQUENCE: 56
gtgaaccgca tcgagctgaa                                            20

<210> SEQ ID NO 57
<211> LENGTH: 4236
<212> TYPE: DNA
<213> ORGANISM: artificial sequence
<220> FEATURE:
<223> OTHER INFORMATION: synthetic polynucleotide: pCLS22972

<400> SEQUENCE: 57

| | |
|---|---|
| atggataaga aatactcaat aggactggat atcggcacaa atagcgtcgg atgggcggtg | 60 |
| atcactgatg aatataaggt tccgtctaaa aagttcaagg ttctgggaaa tacagacagg | 120 |
| cacagtatca aaaaaatct tatagggct cttttatttg acagtggaga cacagcggaa | 180 |
| gcgactcgtc tgaaaaggac agctcgtaga aggtatacac gtaggaagaa tcgtatttgt | 240 |
| tatttgcagg agatttttc aaatgagatg gcgaaagtag atgatagttt ctttcataga | 300 |
| cttgaagagt cttttttggt ggaagaggac aagaagcatg aacgtcatcc tattttttgga | 360 |
| aatatagtag atgaagttgc ttatcatgag aaatatccaa ctatctatca tctgagaaaa | 420 |
| aaattggtag attctactga taaagcggat ttgaggctga tctatttggc cttagcgcat | 480 |
| atgattaagt ttcgtggtca tttttttgatt gagggagacc tgaatcctga taatagtgat | 540 |
| gtggacaaac tgtttatcca gttggtacaa acctacaatc aattatttga agaaaaccct | 600 |
| attaacgcaa gtgagtagaa tgctaaagcg attctttctg caagattgag taaatcaaga | 660 |
| cgcctggaaa atctgattgc tcagctgccc ggtgagaaga aaaatggctt atttgggaat | 720 |

```
ctgattgctt tgtcattggg tttgacccct aattttaaat caaattttga tttggcagaa    780
gatgctaaac tgcaacttte aaaagatact tacgatgatg atttagataa tctgttggcg    840
caaattggag atcaatatgc tgatttgttt ttggcagcta agaatttatc agatgctatt    900
ctgctttcag atatcttgag agtaaatact gaaataacta aggctcccct gtcagcttca    960
atgattaaaa ggtacgatga acatcatcaa gacttgactc ttttaaaggc tctggttaga   1020
caacaacttc cagaaaagta taagaaaatc ttttttgatc aatcaaaaaa cggatatgca   1080
ggttatattg atgggggagc tagccaagaa gaattttata aatttatcaa accaatttta   1140
gaaaaaatgg atggtactga ggaactgttg gtgaaattga atcgtgaaga tttgctgagg   1200
aagcaaagga cctttgacaa cggctctatt ccccatcaaa ttcacttggg tgagctgcat   1260
gctattttgc gccgtcaaga ggacttttat ccatttttaa aagacaatcg tgagaagatt   1320
gaaaaaatct tgacttttcg tattccttat tatgttggtc cattggcgcg tggcaatagt   1380
cgttttgcat ggatgactag gaagtctgaa gaaacaatta ccccttggaa ttttgaagaa   1440
gttgtcgata aaggtgcttc agctcaatca tttattgaaa ggatgacaaa ctttgataaa   1500
aatcttccaa atgaaaaagt actgccaaaa catagtttgc tttatgagta ttttacggtt   1560
tataacgaat tgacaaggt caaatatgtt actgaaggaa tgagaaaacc agcatttctt   1620
tcaggtgaac agaagaaagc cattgttgat ctgctgttca aaacaaatag aaaagtaacc   1680
gttaagcaat taaagaaga ttatttcaaa aaaatagaat gttttgatag tgttgaaatt   1740
tcaggagttg aagatagatt taatgcttca ctgggtacct accatgatt gttgaaaatt   1800
attaaagata aagattttt ggataatgaa gaaaatgaag atatcttaga ggatattgtt   1860
ctgacattga ccttatttga agataggag atgattgagg aaagacttaa aacatatgct   1920
cacctgtttg atgataaggt gatgaaacag cttaaacgta ggcgttatac tggttgggga   1980
cgtttgtcta gaaaattgat taatggtatt agggataagc aatctggcaa aacaatactg   2040
gattttttga aatcagatgg ttttgccaat aggaatttta tgcagctgat ccatgatgat   2100
agtttgacat ttaaagaaga tattcaaaaa gcacaagtgt ctggacaagg cgatagttta   2160
catgaacata ttgcaaatct ggctggtagc cctgctatta aaaaaggtat tttacagact   2220
gtaaaagttg ttgatgaatt ggtcaaagta atggggaggc ataagccaga aaatatcgtt   2280
attgaaatgg cacgtgaaaa tcagacaact caaaagggcc agaaaaattc cagagagcgt   2340
atgaaaagaa tcgaagaagg tatcaaagaa ctgggaagtc agattcttaa agagcatcct   2400
gttgaaaata ctcaattgca aaatgaaaag ctgtatctgt attatctgca aaatggaaga   2460
gacatgtatg tggaccaaga attagatatt aatcgtctga gtgattatga tgtcgatcac   2520
attgttccac aaagtttcct taagacgat tcaatagaca ataaggtctt aacgcgttct   2580
gataaaaatc gtggtaaatc cgataacgtt ccaagtgaag aagtagtcaa aaagatgaaa   2640
aactattgga gacaactttt gaacgccaag ctgatcactc aacgtaagtt tgataattta   2700
acgaaagctg aacgtggagg tttgagtgaa cttgataaag ctggttttat caaaaggcaa   2760
ttggttgaaa ctaggcaaat cactaagcat gtggcacaaa ttttggatag taggatgaat   2820
actaaatacg atgaaaatga taacttatt agagaggtta aagtgattac cctgaaatct   2880
aaattagttt ctgacttcag aaaagatttc caattctata agtacgtga gattaacaat   2940
taccatcatg cccatgatgc gtatttgaat gccgtcgttg gaactgcttt gattaagaaa   3000
tatccaaaac ttgaatccga gtttgtctat ggtgattata agtttatga tgttcgtaaa   3060
atgattgcta agtctgagca agaaatagge aaagcaaccg caaaatattt cttttactct   3120
```

```
aatatcatga acttcttcaa aacagaaatt acacttgcaa atggagagat taggaaacgc    3180
cctctgatcg aaactaatgg ggaaactgga gaaattgtct gggataaagg gagagatttt    3240
gccacagtga ggaaagtatt gtccatgccc caagtcaata ttgtcaagaa aacagaagta    3300
cagacaggcg gattctccaa ggagtcaatt ctgccaaaaa gaaattccga caagttgatt    3360
gctcgtaaaa aagactggga cccaaaaaaa tatggtggtt ttgatagtcc aacggtagct    3420
tattcagtcc tggtggttgc taaggtggaa aaagggaaat ccaagaagtt aaaatccgtt    3480
aaagagctgt tggggatcac aattatggaa agaagttcct ttgaaaaaaa tccgattgac    3540
tttttagaag ctaaaggata taaggaagtt aaaaaagacc tgatcattaa actgcctaaa    3600
tatagtcttt ttgagttaga aaacggtcgt aaaaggatgc tggctagtgc cggagaactg    3660
caaaaaggaa atgagctggc tctgccaagc aaatatgtga atttttata tctggctagt    3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attctggcag atgccaattt agataaagtt cttagtgcat ataacaaaca tagagacaaa    3900
ccaatacgtg aacaagcaga aaatattatt catctgttta cgttgacgaa tcttggagca    3960
cccgctgctt ttaaatattt tgatacaaca attgatcgta aaagatatac gtctacaaaa    4020 gaagtttttag atgccactct tatccatcaa tccatcactg gtctttatga aacaaggatt    4080
gatttgagtc agttgggagg tgacggggcc cctaaaaaga aacgtaaggt tgaatctccg    4140
aagaaaaagc ggaaggtcga gagtcccaag aagaagcgca agtggagggg gaattcttat    4200
ccatacgacg ttcctgatta cgcggccgac tgataa                              4236

<210> SEQ ID NO 58
<211> LENGTH: 496
<212> TYPE: DNA
<213> ORGANISM: artificial sequence
<220> FEATURE:
<223> OTHER INFORMATION: synthetic polynucleotide: pCLS23328

<400> SEQUENCE: 58
cgcgcggccg cgcgtggccg gacgggccgg tacctgtaca aaaaagcagg ctttaaagga      60
accaattcag tcgactggat ccggtaccaa ggtcgggcag gaagagggcc tatttcccat     120
gattccttca tatttgcata tacgatacaa ggctgttaga gagataatta gaattaatttt    180 gactgtaaac acaaagatat tagtacaaaa tacgtgacgt agaaagtaat aatttcttgg     240
gtagtttgca gttttaaaat tatgttttaa aatggactat catatgctta ccgtaacttg     300
aaagtatttc gatttcttgg ctttatatat cttgtggaaa ggacgaaaca ccgtgaaccg     360
catcgagctg aagttttaga gctagaaata gcaagttaaa ataaggctag tccgttatca     420
acttgaaaaa gtggcaccga gtcggtgctt ttttttctaga cccagcaggt ggccactggg     480
gcccgcgaat tcgcgt                                                     496

<210> SEQ ID NO 59
<211> LENGTH: 21
<212> TYPE: DNA
<213> ORGANISM: artificial sequence
<220> FEATURE:
<223> OTHER INFORMATION: synthetic oligonucleotide: primer 1

<400> SEQUENCE: 59
ctgcaccacc ggcaagctgc c                                                21
```

```
<210> SEQ ID NO 60
<211> LENGTH: 17
<212> TYPE: DNA
<213> ORGANISM: artificial sequence
<220> FEATURE:
<223> OTHER INFORMATION: synthetic oligonucleotide: primer 2

<400> SEQUENCE: 60
ccgccacaac atcgagg                                                  17

<210> SEQ ID NO 61
<211> LENGTH: 166
<212> TYPE: PRT
<213> ORGANISM: Thermus thermophilus HB8
<220> FEATURE:
<221> NAME/KEY: MISC_FEATURE
<223> OTHER INFORMATION: Ruvc Structure

<400> SEQUENCE: 61
```

Met Val Val Ala Gly Ile Asp Pro Gly Ile Thr His Leu Gly Leu Gly
1               5                   10                  15

Val Val Ala Val Glu Gly Lys Gly Ala Leu Lys Ala Arg Leu Leu His
            20                  25                  30

Gly Glu Val Val Lys Thr Ser Pro Gln Glu Pro Ala Lys Glu Arg Val
        35                  40                  45

Gly Arg Ile His Ala Arg Val Leu Glu Val Leu His Arg Phe Arg Pro
    50                  55                  60

Glu Ala Val Ala Val Glu Glu Gln Phe Phe Tyr Arg Gln Asn Glu Leu
65                  70                  75                  80

Ala Tyr Lys Val Gly Trp Ala Leu Gly Ala Val Leu Val Ala Ala Phe
                85                  90                  95

Glu Ala Gly Val Pro Val Tyr Ala Tyr Gly Pro Met Gln Val Lys Gln
            100                 105                 110

Ala Leu Ala Gly His Gly His Ala Ala Lys Glu Glu Val Ala Leu Met
        115                 120                 125

Val Arg Gly Ile Leu Gly Leu Lys Glu Ala Pro Arg Pro Ser His Leu
    130                 135                 140

Ala Asn Ala Leu Ala Ile Ala Leu Thr His Ala Phe Tyr Ala Arg Met
145                 150                 155                 160

Gly Thr Ala Lys Pro Leu
                165

```
<210> SEQ ID NO 62
<211> LENGTH: 279
<212> TYPE: PRT
<213> ORGANISM: Streptococcus pyogenes serotype M1
<220> FEATURE:
<221> NAME/KEY: MISC_FEATURE
<223> OTHER INFORMATION: RuvC Cas9 SP

<400> SEQUENCE: 62
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

```
Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu
            275

<210> SEQ ID NO 63
<211> LENGTH: 173
<212> TYPE: PRT
<213> ORGANISM: Escherichia coli
<220> FEATURE:
<221> NAME/KEY: MISC_FEATURE
<223> OTHER INFORMATION: RuvC domain

<400> SEQUENCE: 63

Met Ala Ile Ile Leu Gly Ile Asp Pro Gly Ser Arg Val Thr Gly Tyr
  1               5                  10                  15

Gly Val Ile Arg Gln Val Gly Arg Gln Leu Ser Tyr Leu Gly Ser Gly
                 20                  25                  30

Cys Ile Arg Thr Lys Val Asp Asp Leu Pro Ser Arg Leu Lys Leu Ile
             35                  40                  45

Tyr Ala Gly Val Thr Glu Ile Ile Thr Gln Phe Gln Pro Asp Tyr Phe
         50                  55                  60

Ala Ile Glu Gln Val Phe Met Ala Lys Asn Ala Asp Ser Ala Leu Lys
 65                  70                  75                  80

Leu Gly Gln Ala Arg Gly Val Ala Ile Val Ala Ala Val Asn Gln Glu
                 85                  90                  95

Leu Pro Val Phe Glu Tyr Ala Ala Arg Gln Val Lys Gln Thr Val Val
            100                 105                 110

Gly Ile Gly Ser Ala Glu Lys Ser Gln Val Gln His Met Val Arg Thr
            115                 120                 125

Leu Leu Lys Leu Pro Ala Asn Pro Gln Ala Asp Ala Ala Asp Ala Leu
            130                 135                 140
```

Ala Ile Ala Ile Thr His Cys His Val Ser Gln Asn Ala Met Gln Met
145                 150                 155                 160

Ser Glu Ser Arg Leu Asn Leu Ala Arg Gly Arg Leu Arg
            165                 170

<210> SEQ ID NO 64
<211> LENGTH: 300
<212> TYPE: PRT
<213> ORGANISM: Streptococcus thermophilus
<220> FEATURE:
<221> NAME/KEY: MISC_FEATURE
<223> OTHER INFORMATION: RuvC domain

<400> SEQUENCE: 64

Met Leu Phe Asn Lys Cys Ile Ile Ser Ile Asn Leu Asp Phe Ser
1               5                   10                  15

Asn Lys Glu Lys Cys Met Thr Lys Pro Tyr Ser Ile Gly Leu Asp Ile
                20                  25                  30

Gly Thr Asn Ser Val Gly Trp Ala Val Ile Thr Asp Asn Tyr Lys Val
            35                  40                  45

Pro Ser Lys Lys Met Lys Val Leu Gly Asn Thr Ser Lys Lys Tyr Ile
50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Tyr Thr Arg Arg
                85                  90                  95

Arg Asn Arg Ile Leu Tyr Leu Gln Glu Ile Phe Ser Thr Glu Met Ala
                100                 105                 110

Thr Leu Asp Asp Ala Phe Phe Gln Arg Leu Asp Asp Ser Phe Leu Val
            115                 120                 125

Pro Asp Asp Lys Arg Asp Ser Lys Tyr Pro Ile Phe Gly Asn Leu Val
130                 135                 140

Glu Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                165                 170                 175

Leu Ala Leu Ala His Met Ile Lys Tyr Arg Gly His Phe Leu Ile Glu
            180                 185                 190

Gly Glu Phe Asn Ser Lys Asn Asn Asp Ile Gln Lys Asn Phe Gln Asp
                195                 200                 205

Phe Leu Asp Thr Tyr Asn Ala Ile Phe Glu Ser Asp Leu Ser Leu Glu
210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
            260                 265                 270

Phe Arg Lys Cys Phe Asn Leu Asp Glu Lys Ala Ser Leu His Phe Ser
                275                 280                 285

Lys Glu Ser Tyr Asp Glu Asp Leu Glu Thr Leu Leu
290                 295                 300